United States Patent
Braje et al.

(10) Patent No.: US 7,790,727 B2
(45) Date of Patent: Sep. 7, 2010

(54) BENZENESULFONANILIDE COMPOUNDS SUITABLE FOR TREATING DISORDERS THAT RESPOND TO MODULATION OF THE SEROTONIN 5-HT6 RECEPTOR

(75) Inventors: Wilfried Martin Braje, Rinteln (DE); Sean Colm Turner, Mannheim (DE); Andreas Haupt, Schwetzingen (DE); Udo Lange, Berlin (DE); Karla Drescher, Dossenheim (DE); Karsten Wicke, Altrip (DE); Liliane Unger, Ludwigshafen (DE); Mario Mezler, Forst a.d.W. (DE); Wolfgang Wernet, Neustadt a.d.W. (DE); Matthias Mayrer, Biblis (DE); Ana Jongen-Relo, Hochdorf-Assenheim (DE); Anton Bespalov, Schifferstadt (DE); Min Zhang, Gurnee, IL (US)

(73) Assignee: Abbott GmbH & Co. KG, Wiesbaden (DE)

( * ) Notice: Subject to any disclaimer, the term of this patent is extended or adjusted under 35 U.S.C. 154(b) by 0 days.

(21) Appl. No.: 12/262,455

(22) Filed: Oct. 31, 2008

(65) Prior Publication Data

US 2009/0131452 A1 May 21, 2009

Related U.S. Application Data

(60) Provisional application No. 61/001,656, filed on Nov. 2, 2007.

(51) Int. Cl.
*A61K 31/495* (2006.01)
*A61K 31/496* (2006.01)
*C07D 295/135* (2006.01)
*C07D 317/62* (2006.01)

(52) U.S. Cl. .................. 514/254.11; 514/255.03; 544/377; 544/395

(58) Field of Classification Search .................. None
See application file for complete search history.

(56) References Cited

U.S. PATENT DOCUMENTS 7,381,728 B2 * 6/2008 Dean et al. ............. 514/255.03
2003/0069233 A1 4/2003 Bromidge

FOREIGN PATENT DOCUMENTS

| WO | 98/27081 | * | 6/1998 |
| WO | 0012073 | A1 | 3/2000 |
| WO | 0012623 | A3 | 3/2000 |
| WO | 0208179 | A1 | 1/2002 |

OTHER PUBLICATIONS

Robichaud et al. Annual Reports in Medicinal Chemistry, vol. 36, p. 11-20 (2000).*
Rogers et al. Psychopharmacology, vol. 158, p. 114-119 (2001).*
Ballaz et al., Analysis of 5-HT6 and HT7 Receptor Gene Expression in Rats Showing Differences in Novelty-Seeking Behavior, Neuroscience, 2007, pp. 428-438, Elsevier Ltd. on behalf of IBRO.

* cited by examiner

*Primary Examiner*—Emily Bernhardt
(74) *Attorney, Agent, or Firm*—Lisa V. Mueller; Polsinelli Shughart PC

(57) ABSTRACT

The present invention relates to novel benzenesulfonanilide compounds of the formulae I and I' and physiologically tolerated acid addition salts and the N-oxides thereof. The compounds possess valuable therapeutic properties and are particularly suitable, for treating diseases that respond to modulation of the serotonin 5-$HT_6$ receptor.

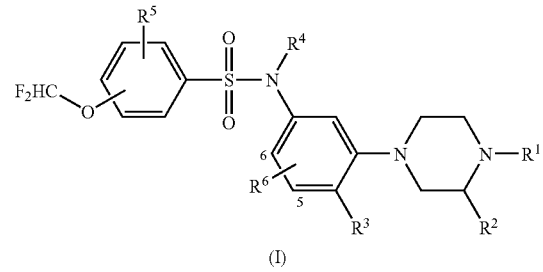

(I)

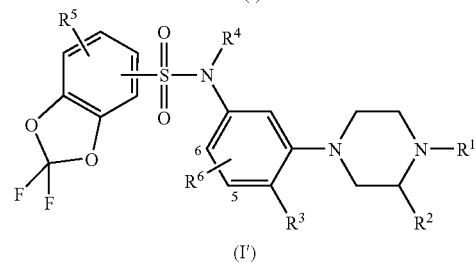

(I')

wherein
$R^1$ is hydrogen or methyl
$R^2$ is hydrogen or methyl
$R^3$ hydrogen, fluorine $C_1$-$C_2$ alkoxy or fluorinated $C_1$-$C_2$ alkoxy;
$R^4$ is hydrogen, $C_1$-$C_4$ alkyl or fluorinated $C_1$-$C_4$ alkyl;
$R^5$ is hydrogen, fluorine, $C_1$-$C_2$ alkyl, fluorinated $C_1$-$C_2$ alkyl, $C_1$-$C_2$ alkoxy or fluorinated $C_1$-$C_2$ alkoxy; and
$R^6$ is hydrogen, fluorine or chlorine.

31 Claims, No Drawings

BENZENESULFONANILIDE COMPOUNDS SUITABLE FOR TREATING DISORDERS THAT RESPOND TO MODULATION OF THE SEROTONIN 5-HT6 RECEPTOR

CROSS-REFERENCE TO RELATED APPLICATIONS

This application claims the benefit of U.S. Provisional Application Ser. No. 61/001,656 filed Nov. 2, 2007, the disclosure of which is hereby incorporated by reference in its entirety.

BACKGROUND OF THE INVENTION

The present invention relates to novel benzenesulfonanilide compounds. The compounds possess valuable therapeutic properties and are particularly suitable for treating diseases that respond to modulation of the serotonin 5-HT6 receptor.

Serotonin (5-hydroxytryptamine, 5-HT), a monoamine neurotransmitter and local hormone, is formed by the hydroxylation and decarboxylation of tryptophan. The greatest concentration is found in the enterochromaffin cells of the gastrointestinal tract, the remainder being predominantly present in platelets and in the Central Nervous System (CNS). 5-HT is implicated in a vast array of physiological and pathophysiological pathways. In the periphery, it contracts a number of smooth muscles and induces endothelium-dependent vasodilation. In the CNS, it is believed to be involved in a wide range of functions, including the control of appetite, mood, anxiety, hallucinations, sleep, vomiting and pain perception.

Neurons that secrete 5-HT are termed serotonergic. The function of 5-HT is exerted upon its interaction with specific (serotonergic) neurons. Until now, seven types of 5-HT receptors have been identified: $5\text{-}HT_1$ (with subtypes $5\text{-}HT_{1A}$, $5\text{-}HT_{1B}$, $5\text{-}HT_{1D}$, $5\text{-}HT_{1E}$ and $5\text{-}HT_{1F}$), $5\text{-}HT_2$ (with subtypes $5\text{-}HT_{2A}$, $5\text{-}HT_{2B}$ and $5\text{-}HT_{2C}$), $5\text{-}HT_3$, $5\text{-}HT_4$, $5\text{-}HT_5$ (with subtypes $5\text{-}HT_{5A}$ and $5\text{-}HT_{5B}$), $5\text{-}HT_6$ and $5\text{-}HT_7$. Most of these receptors are coupled to G-proteins that affect the activities of either adenylate cyclase or phospholipase Cγ.

The human $5\text{-}HT_6$ receptors are positively coupled to adenylyl cyclase. They are distributed throughout the limbic, striatal and cortical regions of the brain and show a high affinity to antipsychotics.

The modulation of the $5\text{-}HT_6$ receptor by suitable substances is expected to improve certain disorders including cognitive dysfunctions, such as a deficit in memory, cognition and learning, in particular associated with Alzheimer's disease, age-related cognitive decline and mild cognitive impairment, attention deficit disorder/hyperactivity syndrome, personality disorders, such as schizophrenia, in particular cognitive deficits related with schizophrenia, affective disorders such as depression, anxiety and obsessive compulsive disorders, motion or motor disorders such as Parkinson's disease and epilepsy, migraine, sleep disorders (including disturbances of the Circadian rhythm), feeding disorders, such as anorexia and bulimia, certain gastrointestinal disorders such as Irritable Bowl Syndrome, diseases associated with neurodegeneration, such as stroke, spinal or head trauma and head injuries, such as hydrocephalus, addiction diseases and obesity.

WO 96/027081, WO 00/12623, WO 00/12073, US 2003/0069233, WO 02/08179 and WO 02/92585 disclose certain benzenesulfonanililde compounds having $5HT_6$ receptor antagonist activity and suggest the use of these compounds for the treatment of medical disorders which are susceptible to the treatment with $5HT_6$ receptor antagonists such as certain CNS disorders, drug abuse, ADHD, obesity and type II diabetes. WO 2008087123 suggests compounds having $5HT_6$ receptor antagonist activity for preventing relapse into addiction.

However, there is still an ongoing need for providing compounds having high affinity for the $5\text{-}HT_6$ receptor and which show high selectivity to this receptor. In particular the compounds should have low affinity to adrenergic receptors, such as $\alpha_1$-adrenergic receptor, histamine receptors, such as $H_1$-receptor, and dopaminergic receptors, such as $D_2$-receptor, in order to avoid or reduce considerable side effects associated with modulation of these receptors, such as postural hypotension, reflex tachycardia, potentiation of the antihypertensive effect of prazosin, terazosin, doxazosin and labetalol or dizziness associated to the blockade of the $\alpha_1$-adrenergic receptor, weight gain, sedation, drowsiness or potentiation of central depressant drugs associated to the blockade of the $H_1$-receptor, or extrapyramidal movement disorder, such as dystonia, parkinsonism, akathisia, tardive dyskinesia or rabbit syndrome, or endocrine effects, such as prolactin elevation (galactorrhea, gynecomastia, menstruyl changes, sexual dysfunction in males), associated to the blockade of the $D_2$-receptor.

It is an object of the present invention to provide compounds which have a high affinity and selectivity for the $5\text{-}HT_6$ receptor, thus allowing the treatment of disorders related to or affected by the $5\text{-}HT_6$ receptor.

The compounds should also have good pharmacological profile, e.g., a good bioavailability and/or a good metabolic stability.

SUMMARY OF THE INVENTION

It has now been found that the benzenesulfonamide compounds of the formulae (I) and (I') as defined herein, their physiologically tolerated acid addition salts and the N-oxides thereof exhibit to a surprising and unexpected degree, selective binding to the $5\text{-}HT_6$ receptor. Therefore, the present invention relates to the compounds of formulae (I) and (I')

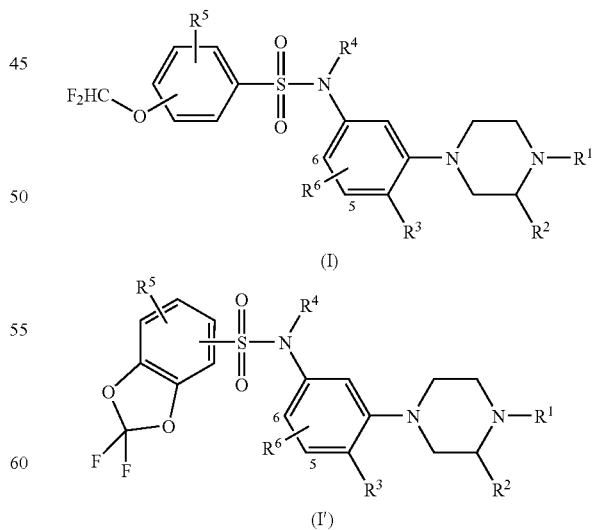

wherein
$R^1$ is hydrogen or methyl;
$R^2$ is hydrogen or methyl;

$R^3$ hydrogen, fluorine $C_1$-$C_2$ alkoxy or fluorinated $C_1$-$C_2$ alkoxy;

$R^4$ is hydrogen, $C_1$-$C_4$ alkyl or fluorinated $C_1$-$C_4$ alkyl;

$R^5$ is hydrogen, fluorine, $C_1$-$C_2$ alkyl, fluorinated $C_1$-$C_2$ alkyl, $C_1$-$C_2$ alkoxy or fluorinated $C_1$-$C_2$ alkoxy; and $R^6$ is hydrogen, fluorine or chlorine; and to the physiologically tolerated acid addition salts and the N-oxides thereof.

The present invention also relates to a pharmaceutical composition which comprises at least one benzenesulfonanilide compound of the formulae (I) or (I') and/or at least one physiologically tolerated acid addition salt of (I) or (I') and/or at least one N-oxide of (I) or (I'), where appropriate together with physiologically acceptable carriers and/or auxiliary substances.

The present invention further relates to the use of a benzenesulfonanilide compound of the formulae (I) or (I') and/or physiologically tolerated acid addition salts thereof and/or at least one N-oxide of (I) or (I'), for preparing a pharmaceutical composition, optionally together with at least one physiologically acceptable carrier or auxiliary substance.

The compounds are selective 5-HT$_6$ receptor ligands. Thus the compounds are particularly suitable for the treatment of disorders of the central nervous system, addiction diseases or obesity, as these disorders and diseases are likely to respond to influencing by 5-HT$_6$ receptor ligands. Therefore the present invention also provides a method for treating disorders in mammals, said method comprising administering an effective amount of at least one compound of the formula (I) or (I') and/or at least one physiologically tolerated acid addition salt of (I) or (I') and/or at least one N-oxide of (I) or (I') to a subject in need thereof.

DETAILED DESCRIPTION OF THE INVENTION

The diseases which are susceptible to treatment with a benzenesulfonanilide compound of the formulae (I) and (I') include, e.g., disorders and diseases of the central nervous system, in particular cognitive dysfunctions, such as a deficit in memory, cognition and learning, in particular associated with Alzheimer's disease, age-related cognitive decline and mild cognitive impairment, attention deficit disorder/hyperactivity syndrome (ADHD), personality disorders, such as schizophrenia, in particular cognitive deficits related with schizophrenia, affective disorders such as depression, anxiety and obsessive compulsive disorders, motion or motor disorders such as Parkinson's disease and epilepsy, migraine, sleep disorders (including disturbances of the Circadian rhythm), feeding disorders, such as anorexia and bulimia, certain gastrointestinal disorders such as Irritable Bowel Syndrome, diseases associated with neurodegeneration, such as stroke, spinal or head trauma and head injuries, including hydrocephalus, drug addiction and obesity.

According to the invention, at least one benzenesulfonanilide compound of the general formulae (I) or (I') having the meanings mentioned at the outset is used for treating the above mentioned diseases, disorders or medical indications. Provided the compounds of the formulae (I) or (I') of a given constitution may exist in different spatial arrangements, for example if they possess one or more centers of asymmetry, polysubstituted rings or double bonds, or as different tautomers, it is also possible to use enantiomeric mixtures, in particular racemates, diastereomeric mixtures and tautomeric mixtures, preferably, however, the respective essentially pure enantiomers, diastereomers and tautomers of the compounds of formulae (I) or (I') and/or of their salts and/or their N-oxides.

It is likewise possible to use physiologically tolerated salts of the compounds of the formulae (I) or (I'), especially acid addition salts with physiologically tolerated acids. Examples of suitable physiologically tolerated organic and inorganic acids are hydrochloric acid, hydrobromic acid, phosphoric acid, sulfuric acid, $C_1$-$C_4$-alkylsulfonic acids, such as methanesulfonic acid, aromatic sulfonic acids, such as benzenesulfonic acid and toluenesulfonic acid, oxalic acid, maleic acid, fumaric acid, lactic acid, tartaric acid, adipic acid and benzoic acid. Other utilizable acids are described in Fortschritte der Arzneimittelforschung [Advances in drug research], Volume 10, pages 224 ff., Birkhäuser Verlag, Basel and Stuttgart, 1966.

It is likewise possible to use N-oxides of the compounds of the formulae (I) or (I'), if those compounds contain a basic nitrogen atom, such as the nitrogen atom of the piperazine moiety.

The organic moieties mentioned in the above definitions of the variables are—like the term halogen—collective terms for individual listings of the individual group members. The prefix $C_n$-$C_m$ indicates in each case the possible number of carbon atoms in the group.

As used herein, $C_1$-$C_4$ alkyl is a straight-chain or branched alkyl group having 1, 2, 3 or 4 carbon atoms. Examples of such a group include methyl, ethyl, n-propyl, 1-methylethyl (isopropyl), n-butyl, 1-methylpropyl (=2-butyl), 2-methylpropyl (=isobutyl) and 1,1-dimethylethyl (=tert.-butyl).

As used herein, fluorinated $C_1$-$C_2$ alkyl is a straight-chain or branched alkyl group having 1 or 2 carbon atoms, wherein at least one hydrogen atom, e.g., 1, 2, 3, 4 or 5 hydrogen atoms, are replaced by fluorine. Examples of such a group include fluoromethyl, difluoromethyl, trifluoromethyl, 2-fluoroethyl, 2,2-difluoroethyl, 2,2,2-trifluoroethyl, 1,1,2,2-tetrafluoroethyl and 1,1,2,2,2-pentafluoroethyl.

As used herein, fluorinated $C_1$-$C_4$ alkyl is a straight-chain or branched alkyl group having 1, 2, 3 or 4 carbon atoms, wherein at least one hydrogen atom, e.g., 1, 2, 3, 4, 5, 6 or 7 hydrogen atoms, are replaced by fluorine. Examples of such a group include fluoromethyl, difluoromethyl, trifluoromethyl, 2-fluoroethyl, 2,2-difluoroethyl, 2,2,2-trifluoroethyl, 1,1,2,2-tetrafluoroethyl, 1,1,2,2,2-pentafluoroethyl, 3-fluoropropyl, 3,3-difluoropropyl, 3,3,3-trifluoropropyl, 2,2,3,3-tetrafluoropropyl, 2,2,3,3,3-pentafluoropropyl, 1,1,2,2,3,3,3-heptafluoropropyl, 2-fluoro-1-methylethyl, 2,2-difluoro-1-methylethyl, 2,2,2-trifluoro-1-methylethyl, 2,2,2-trifluoro-1-(trifluoromethyl)ethyl etc.

As used herein, $C_1$-$C_2$ alkoxy is a straight-chain alkyl group having 1 or 2 carbon atoms which is bound to the remainder of the molecule via an oxygen atom. Examples of such a group are methoxy and ethoxy.

As used herein, fluorinated $C_1$-$C_2$ alkoxy is an alkoxy group as defined above, wherein at least one, e.g., 1, 2, 3, 4 or 5 hydrogen atoms are replaced by fluorine atoms. Examples of such a group are fluoromethoxy, difluoromethoxy, trifluoromethoxy, 2-fluoroethoxy, 2,2-difluoroethoxy, 2,2,2-trifluoroethoxy and 1,1,2,2-tetrafluoroethoxy.

In the formulae I and I', the integers "5" and "6" denominate positions of the benzene ring.

A first preferred embodiment of the invention relates to compounds of the formulae I and I', to their pharmacologically tolerated salts and to the N-oxides thereof, wherein $R^1$ is hydrogen.

Another preferred embodiment of the invention relates to compounds of the formulae I and I', to their pharmacologically tolerated salts and to the N-oxides thereof, wherein $R^1$ is methyl.

A preferred embodiment of the invention relates to compounds of the formulae I and I', to their pharmacologically tolerated salts and to the N-oxides thereof, wherein $R^2$ is hydrogen.

Another embodiment of the invention relates to compounds of the formulae I and I', wherein $R^2$ is methyl. In the compounds, wherein $R^2$ is methyl, the carbon atom that carries $R^2$ creates a center of chirality. Thus, a specific embodiment of the invention relates to compounds of the formula I, to their pharmacologically tolerated salts and to the N-oxides thereof, wherein $R^2$ is methyl and wherein the carbon atom that carries $R^2$ has S-configuration. Another specific embodiment of the invention relates to compounds of the formulae I and I', to their pharmacologically tolerated salts and to the N-oxides thereof, wherein $R^2$ is methyl and wherein the carbon atom that carries $R^2$ has R-configuration.

Likewise preferred are mixtures of compounds of the present invention, wherein the carbon atom that carries $R^2$ has S-configuration or R-configuration, respectively. These mixtures may contain equal amounts or non-equal amounts of the compound I, or equal amounts or non-equal amounts of the compound I', respectively, that have R-configuration with regard to the moiety CH—$R^2$ and of the compound I or I' that have S-configuration with regard to CH—$R^2$.

The term "enantiomerically pure" means that the mixture contains the respective compound in an entaniomeric excess of at least 80%, in particular at least 90% (ee).

Preference is given to compounds of the formulae I and I', to their pharmacologically tolerated salts and to the N-oxides thereof, wherein $R^3$ is methoxy, difluoromethoxy or trifluoromethoxy, in particular methoxy. Likewise preference is given to compounds of the formulae I and I', to their pharmacologically tolerated salts and to the N-oxides thereof, wherein $R^3$ is hydrogen or fluorine, in particular hydrogen.

Preference is given to compounds of the formulae I and I', to their pharmacologically tolerated salts and to the N-oxides thereof, wherein $R^4$ is hydrogen, methyl, ethyl, n-propyl, 2-fluoroethyl or 3-fluoropropyl. More preference is given to compounds of the present invention, wherein $R^4$ is hydrogen.

$R^5$ is preferably selected from the group consisting of hydrogen, fluorine, methyl, trifluoromethyl, methoxy, difluoromethoxy and trifluoromethoxy and more preferably from hydrogen, methoxy and difluoromethoxy. In a particular preferred embodiment of the invention, $R^5$ is hydrogen. In another particular preferred embodiment of the invention, $R^5$ is selected from fluorine, methyl, trifluoromethyl, methoxy, difluoromethoxy and trifluoromethoxy and more preferably from methoxy and difluoromethoxy.

$R^6$ is preferably selected from the group consisting of hydrogen and fluorine. In a particular preferred embodiment of the invention, $R^6$ is hydrogen. In another particular preferred embodiment of the invention $R^6$ is different from hydrogen, in particular fluorine. If $R^6$ is different from hydrogen it is preferably located in the 5- or 6-position of the benzene ring.

Preference is given to those compounds of the formulae I and I', to their pharmacologically tolerated salts and to the N-oxides thereof, wherein $R^3$ is methoxy and $R^6$ is hydrogen, or $R^3$ is methoxy and $R^6$ is fluorine being located in the 5- or 6-position of the benzene ring, or both $R^3$ and $R^6$ are hydrogen or $R^3$ is hydrogen and $R^6$ is fluorine being located in the 5- or 6-position of the benzene ring.

A particular preferred embodiment of the invention relates to compounds of the formulae I and I', to their pharmacologically tolerated salts and to the N-oxides thereof, wherein $R^1$ is hydrogen or methyl;
$R^2$ is hydrogen or methyl, in particular hydrogen;
$R^3$ hydrogen, fluorine, $C_1$-$C_2$ alkoxy or fluorinated $C_1$-$C_2$ alkoxy, preferably hydrogen, methoxy, difluoromethoxy or trifluoromethoxy, in particular hydrogen, methoxy;
$R^4$ is hydrogen, methyl, ethyl, n-propyl or 3-fluoropropyl;
$R^5$ is selected from the group consisting of hydrogen, fluorine, methyl, trifluoromethyl, methoxy, difluoromethoxy and trifluoromethoxy and more preferably from hydrogen, methoxy and difluoromethoxy; and
$R^6$ is hydrogen or fluorine, which is located in the 5- or 6-position of the benzene ring.

Amongst the compounds of this particular preferred embodiment, preference is given to those compounds of the formulae I and I', to their pharmacologically tolerated salts and to the N-oxides thereof, wherein $R^3$ is methoxy and $R^6$ is hydrogen, or $R^3$ is methoxy and $R^6$ is fluorine being located in the 5- or 6-position of the benzene ring, or both $R^3$ and $R^6$ are hydrogen or $R^3$ is hydrogen and $R^6$ is fluorine being located in the 5- or 6-position of the benzene ring.

A particular embodiment (1) of the invention relates to compounds of the formulae I and I', to their pharmacologically tolerated salts and to the N-oxides thereof, wherein $R^1$ is hydrogen or methyl;
$R^2$ is hydrogen or methyl, in particular hydrogen;
$R^3$ $C_1$-$C_2$ alkoxy or fluorinated $C_1$-$C_2$ alkoxy, preferably methoxy, difluoromethoxy or trifluoromethoxy, in particular methoxy;
$R^4$ is hydrogen or $C_1$-$C_2$ alkyl;
$R^5$ is hydrogen; and
$R^6$ is hydrogen.

Another particular embodiment (2a) of the invention relates to compounds of the formulae I and I', to their pharmacologically tolerated salts and to the N-oxides thereof, wherein $R^3$ is hydrogen. In this particular embodiment, $R^6$ is preferably hydrogen or fluorine, which is located in the 5- or 6-position of the benzene ring.

Another particular embodiment (2b) of the invention relates to compounds of the formulae I and I', to their pharmacologically tolerated salts and to the N-oxides thereof, wherein $R^3$ is fluorine. In this particular embodiment, $R^6$ is preferably hydrogen.

Another particular embodiment (3) of the invention relates to compounds of the formulae I and I', to their pharmacologically tolerated salts and to the N-oxides thereof, wherein $R^4$ is $C_3$-$C_4$ alkyl or fluorinated $C_1$-$C_4$ alkyl.

Another particular embodiment (4) of the invention relates to compounds of the formulae I and I', to their pharmacologically tolerated salts and to the N-oxides thereof, wherein $R^5$ is selected from the group consisting of fluorine, $C_1$-$C_2$ alkyl, fluorinated $C_1$-$C_2$ alkyl, $C_1$-$C_2$ alkoxy or fluorinated $C_1$-$C_2$ alkoxy, in particular selected from the group consisting of fluorine, methyl, trifluoromethyl, methoxy, difluoromethoxy and trifluoromethoxy and more preferably from methoxy and difluoromethoxy.

Another particular embodiment (5a) of the invention relates to compounds of the formulae I and I', to their pharmacologically tolerated salts and to the N-oxides thereof, wherein $R^6$ is fluorine or chlorine, in particular fluorine, wherein $R^6$ is located in the 5-position of the benzene ring. In this embodiment, $R^3$ is preferably hydrogen, methoxy, difluoromethoxy or trifluoromethoxy, in particular hydrogen or methoxy.

Another particular embodiment (5b) of the invention relates to compounds of the formulae I and I', to their pharmacologically tolerated salts and to the N-oxides thereof, wherein $R^6$ is fluorine or chlorine, in particular fluorine, wherein $R^6$ is located in the 6-position of the benzene ring. In this embodiment, $R^3$ is preferably hydrogen, methoxy, difluoromethoxy or trifluoromethoxy, in particular hydrogen or methoxy.

A particular preferred embodiment Ia of the invention relates to compounds of the formula I, to their pharmacologically tolerated salts and to the N-oxides thereof, wherein
$R^1$ is hydrogen;
$R^2$ is hydrogen;
$R^3$ is methoxy, difluoromethoxy or trifluoromethoxy, in particular methoxy; and
$R^4$ is hydrogen.

A further particular preferred embodiment Ib of the invention relates to compounds of the formula I, to their pharmacologically tolerated salts and to the N-oxides thereof, wherein
$R^1$ is hydrogen;
$R^2$ is hydrogen;
$R^3$ is methoxy, difluoromethoxy or trifluoromethoxy, in particular methoxy; and
$R^4$ is methyl.

A further particular preferred embodiment Ic of the invention relates to compounds of the formula I, to their pharmacologically tolerated salts and to the N-oxides thereof, wherein
$R^1$ is methyl;
$R^2$ is hydrogen;
$R^3$ is methoxy, difluoromethoxy or trifluoromethoxy, in particular methoxy; and
$R^4$ is hydrogen.

A further particular preferred embodiment Id of the invention relates to compounds of the formula I, to their pharmacologically tolerated salts and to the N-oxides thereof, wherein
$R^1$ is methyl;
$R^2$ is hydrogen;
$R^3$ is methoxy, difluoromethoxy or trifluoromethoxy, in particular methoxy; and
$R^4$ is methyl.

A particular preferred embodiment Ie of the invention relates to compounds of the formula I, to their pharmacologically tolerated salts and to the N-oxides thereof, wherein
$R^1$ is hydrogen;
$R^2$ is hydrogen;
$R^3$ is hydrogen or fluorine, in particular hydrogen; and
$R^4$ is hydrogen.

A further particular preferred embodiment If of the invention relates to compounds of the formula I, to their pharmacologically tolerated salts and to the N-oxides thereof, wherein
$R^1$ is hydrogen;
$R^2$ is hydrogen;
$R^3$ is hydrogen or fluorine, in particular hydrogen; and
$R^4$ is methyl.

A further particular preferred embodiment Ig of the invention relates to compounds of the formula I, to their pharmacologically tolerated salts and to the N-oxides thereof, wherein
$R^1$ is methyl;
$R^2$ is hydrogen;
$R^3$ is hydrogen or fluorine, in particular hydrogen; and
$R^4$ is hydrogen.

A further particular preferred embodiment Ih of the invention relates to compounds of the formula I, to their pharmacologically tolerated salts and to the N-oxides thereof, wherein
$R^1$ is methyl;
$R^2$ is hydrogen;
$R^3$ is hydrogen or fluorine, in particular hydrogen; and
$R^4$ is methyl.

Amongst the compounds of embodiments Ia, Ib, Ic, Id, Ie, If, Ig and Ih, preference is given to those, where the radicals $R^5$ and $R^6$ in formula I are both hydrogen.

Amongst the compounds of embodiments Ia, Ib, Ic, Id, Ie, If, Ig and Ih, likewise preference is given to those, where the radical $R^5$ in formula I is hydrogen and where the radical $R^6$ in formula I is fluorine, which is located in the 5-position or in the 6-position of the benzene ring.

Amongst the compounds of embodiments Ia, Ib, Ic, Id, Ie, If, Ig and Ih, likewise preference is given to those, where the radical $R^5$ in formula I is methoxy and where the radical $R^6$ in formula I is hydrogen.

Amongst the compounds of embodiments Ia, Ib, Ic, Id, Ie, If, Ig and Ih, likewise preference is given to those, where the radical $R^5$ in formula I is methoxy and where the radical $R^6$ in formula I is fluorine, which is located in the 5-position or in the 6-position of the benzene ring.

Amongst the compounds of embodiments Ia, Ib, Ic, Id, Ie, If, Ig and Ih, likewise preference is given to those, where the radical $R^5$ in formula I is difluoromethoxy and where the radical $R^6$ in formula I is hydrogen.

Amongst the compounds of embodiments Ia, Ib, Ic, Id, Ie, If, Ig and Ih, likewise preference is given to those, where the radical $R^5$ in formula I is difluoromethoxy and where the radical $R^6$ in formula I is fluorine, which is located in the 5-position or in the 6-position of the benzene ring.

A particular preferred embodiment I'a of the invention relates to compounds of the formula I', to their pharmacologically tolerated salts and to the N-oxides thereof, wherein
$R^1$ is hydrogen;
$R^2$ is hydrogen;
$R^3$ is methoxy, difluoromethoxy or trifluoromethoxy, in particular methoxy; and
$R^4$ is hydrogen.

A further particular preferred embodiment I'b of the invention relates to compounds of the formula I', to their pharmacologically tolerated salts and to the N-oxides thereof, wherein
$R^1$ is hydrogen;
$R^2$ is methyl;
$R^3$ is methoxy, difluoromethoxy or trifluoromethoxy, in particular methoxy; and
$R^4$ is hydrogen.

A further particular preferred embodiment I'c of the invention relates to compounds of the formula I', to their pharmacologically tolerated salts and to the N-oxides thereof, wherein
$R^1$ is hydrogen;
$R^2$ is hydrogen;
$R^3$ is methoxy, difluoromethoxy or trifluoromethoxy, in particular methoxy; and
$R^4$ is methyl.

A further particular preferred embodiment I'd of the invention relates to compounds of the formula I', to their pharmacologically tolerated salts and to the N-oxides thereof, wherein
$R^1$ is hydrogen;
$R^2$ is methyl;
$R^3$ is methoxy, difluoromethoxy or trifluoromethoxy, in particular methoxy; and
$R^4$ is methyl.

A particular preferred embodiment I'e of the invention relates to compounds of the formula I', to their pharmacologically tolerated salts and to the N-oxides thereof, wherein
$R^1$ is hydrogen;
$R^2$ is hydrogen;
$R^3$ is hydrogen or fluorine, in particular hydrogen; and
$R^4$ is hydrogen.

A further particular preferred embodiment I'f of the invention relates to compounds of the formula I', to their pharmacologically tolerated salts and to the N-oxides thereof, wherein
$R^1$ is hydrogen;
$R^2$ is methyl;
$R^3$ is hydrogen or fluorine, in particular hydrogen; and
$R^4$ is hydrogen.

A further particular preferred embodiment I'g of the invention relates to compounds of the formula I', to their pharmacologically tolerated salts and to the N-oxides thereof, wherein
$R^1$ is hydrogen;
$R^2$ is hydrogen;
$R^3$ is hydrogen or fluorine, in particular hydrogen; and
$R^4$ is methyl.

A further particular preferred embodiment I'h of the invention relates to compounds of the formula I', to their pharmacologically tolerated salts and to the N-oxides thereof, wherein
$R^1$ is hydrogen;
$R^2$ is methyl;
$R^3$ is hydrogen or fluorine, in particular hydrogen; and
$R^4$ is methyl.

Amongst the compounds of embodiments I'a, I'b, I'c, I'd, I'e, I'f, I'g and I'h, preference is given to those, where the radicals $R^5$ and $R^6$ in formula I are both hydrogen.

Amongst the compounds of embodiments I'a, I'b, I'c, I'd, I'e, I'f, I'g and I'h, likewise preference is given to those, where the radical $R^5$ in formula I is hydrogen and where the radical $R^6$ in formula I is fluorine, which is located in the 5-position or in the 6-position of the benzene ring.

Amongst the compounds of the formula I, in particular amongst the compounds of embodiments Ia, Ib, Ic, Id, Ie, If, Ig and Ih, particular preference is given to those, wherein the $OCHF_2$-radical is located on the benzene ring in the meta-position with respect to the sulfonyl group. Amongst these compounds, particular preference is given to those compounds of the formula I, wherein $R^5$ is hydrogen. Amongst these compounds, likewise preference is given to those compounds of the formula I, wherein $R^5$ is different from hydrogen and in particular selected from fluorine, methyl, trifluoromethyl, methoxy, difluoromethoxy and trifluoromethoxy and more preferably from methoxy and difluoromethoxy, and located in the para-position, with respect to the sulfonyl group, or in the para-position, with respect to the $OCHF_2$-radical.

Amongst the compounds of the formula I, in particular amongst the compounds of embodiments Ia, Ib, Ic, Id, Ie, If, Ig and Ih, likewise preference is given to those, wherein the $OCHF_2$-radical is located on the benzene ring in the ortho-position with respect to the sulfonyl group. Amongst these compounds, particular preference is given to those compounds of the formula I, wherein $R^5$ is hydrogen. Amongst these compounds, likewise preference is given to those compounds of the formula I, wherein $R^5$ is different from hydrogen and in particular selected from fluorine, methyl, trifluoromethyl, methoxy, difluoromethoxy and trifluoromethoxy and more preferably from methoxy and difluoromethoxy, and located in the para-position, with respect to the sulfonyl group, or in the para-position, with respect to the $OCHF_2$-radical.

Amongst the compounds of the formula I, in particular amongst the compounds of embodiments Ia, Ib, Ic, Id, Ie, If, Ig and Ih, likewise preference is given to those, wherein the $OCHF_2$-radical is located on the benzene ring in the para-position with respect to the sulfonyl group. Amongst these compounds, particular preference is given to those compounds of the formula I, wherein $R^5$ is hydrogen. Amongst these compounds, likewise preference is given to those compounds of the formula I, wherein $R^5$ is different from hydrogen and in particular selected from fluorine, methyl, trifluoromethyl, methoxy, difluoromethoxy and trifluoromethoxy and more preferably from methoxy and difluoromethoxy, and located in the meta-position, with respect to the sulfonyl group.

Amongst the compounds of the formula I', in particular amongst the compounds of embodiments I'a, I'b, I'c, I'd, I'e, I'f and I'g, particular preference is given to those, wherein the sulfonyl group is attached to the benzene ring in the α-position with respect to the 1,3-dioxole ring. Amongst these compounds, particular preference is given to those compounds of the formula I, wherein $R^5$ is hydrogen.

Amongst the compounds of the formula I', in particular amongst the compounds of embodiments I'a, I'b, I'c, I'd, I'e, I'f and I'g, particular preference is given to those, wherein the sulfonyl group is attached to the benzene ring in the β-position with respect to the 1,3-dioxole ring. Amongst these compounds, particular preference is given to those compounds of the formula I, wherein $R^5$ is hydrogen.

Examples of compounds according to the present invention are the compounds of the formula I, their pharmacologically tolerated salts and the N-oxides thereof, wherein $R^1$, $R^2$, $R^3$, $R^4$, $R^5$, $R^6$ and the position of the moiety $OCHF_2$ on the benzene ring with respect to the sulfonyl group is given in the following table A:

TABLE A

| No. | $R^1$ | $R^2$ | $R^3$ | $R^4$ | $R^{5*}$ | $R^{6**}$ | position of $OCHF_2$*** |
|---|---|---|---|---|---|---|---|
| 1. | H | H | $OCH_3$ | H | H | H | ortho |
| 2. | H | H | $OCH_3$ | $CH_3$ | H | H | ortho |
| 3. | $CH_3$ | H | $OCH_3$ | H | H | H | ortho |
| 4. | $CH_3$ | H | $OCH_3$ | $CH_3$ | H | H | ortho |
| 5. | H | H | $OCH_3$ | H | H | H | meta |
| 6. | H | H | $OCH_3$ | $CH_3$ | H | H | meta |
| 7. | $CH_3$ | H | $OCH_3$ | H | H | H | meta |
| 8. | $CH_3$ | H | $OCH_3$ | $CH_3$ | H | H | meta |
| 9. | H | H | $OCH_3$ | H | H | H | para |
| 10. | H | H | $OCH_3$ | $CH_3$ | H | H | para |
| 11. | $CH_3$ | H | $OCH_3$ | H | H | H | para |

TABLE A-continued

| No. | $R^1$ | $R^2$ | $R^3$ | $R^4$ | $R^{5*}$ | $R^{6**}$ | position of $OCHF_2$*** |
|---|---|---|---|---|---|---|---|
| 12. | CH₃ | H | OCH₃ | CH₃ | H | H | para |
| 13. | H | H | OCHF₂ | H | H | H | ortho |
| 14. | H | H | OCHF₂ | CH₃ | H | H | ortho |
| 15. | CH₃ | H | OCHF₂ | H | H | H | ortho |
| 16. | CH₃ | H | OCHF₂ | CH₃ | H | H | ortho |
| 17. | H | H | OCHF₂ | H | H | H | meta |
| 18. | H | H | OCHF₂ | CH₃ | H | H | meta |
| 19. | CH₃ | H | OCHF₂ | H | H | H | meta |
| 20. | CH₃ | H | OCHF₂ | CH₃ | H | H | meta |
| 21. | H | H | OCHF₂ | H | H | H | para |
| 22. | H | H | OCHF₂ | CH₃ | H | H | para |
| 23. | CH₃ | H | OCHF₂ | H | H | H | para |
| 24. | CH₃ | H | OCHF₂ | CH₃ | H | H | para |
| 25. | H | H | OCF₃ | H | H | H | ortho |
| 26. | H | H | OCF₃ | CH₃ | H | H | ortho |
| 27. | CH₃ | H | OCF₃ | H | H | H | ortho |
| 28. | CH₃ | H | OCF₃ | CH₃ | H | H | ortho |
| 29. | H | H | OCF₃ | H | H | H | meta |
| 30. | H | H | OCF₃ | CH₃ | H | H | meta |
| 31. | CH₃ | H | OCF₃ | H | H | H | meta |
| 32. | CH₃ | H | OCF₃ | CH₃ | H | H | meta |
| 33. | H | H | OCF₃ | H | H | H | para |
| 34. | H | H | OCF₃ | CH₃ | H | H | para |
| 35. | CH₃ | H | OCF₃ | H | H | H | para |
| 36. | CH₃ | H | OCF₃ | CH₃ | H | H | para |
| 37. | H | H | OCH₂CH₂F | H | H | H | ortho |
| 38. | H | H | OCH₂CH₂F | CH₃ | H | H | ortho |
| 39. | CH₃ | H | OCH₂CH₂F | H | H | H | ortho |
| 40. | CH₃ | H | OCH₂CH₂F | CH₃ | H | H | ortho |
| 41. | H | H | OCH₂CH₂F | H | H | H | meta |
| 42. | H | H | OCH₂CH₂F | CH₃ | H | H | meta |
| 43. | CH₃ | H | OCH₂CH₂F | H | H | H | meta |
| 44. | CH₃ | H | OCH₂CH₂F | CH₃ | H | H | meta |
| 45. | H | H | OCH₂CH₂F | H | H | H | para |
| 46. | H | H | OCH₂CH₂F | CH₃ | H | H | para |
| 47. | CH₃ | H | OCH₂CH₂F | H | H | H | para |
| 48. | CH₃ | H | OCH₂CH₂F | CH₃ | H | H | para |
| 49. | H | H | OCH₃ | CH₂CH₃ | H | H | ortho |
| 50. | CH₃ | H | OCH₃ | CH₂CH₃ | H | H | ortho |
| 51. | H | H | OCH₃ | CH₂CH₃ | H | H | meta |
| 52. | CH₃ | H | OCH₃ | CH₂CH₃ | H | H | meta |
| 53. | H | H | OCH₃ | CH₂CH₃ | H | H | para |
| 54. | CH₃ | H | OCH₃ | CH₂CH₃ | H | H | para |
| 55. | H | H | OCHF₂ | CH₂CH₃ | H | H | ortho |
| 56. | CH₃ | H | OCHF₂ | CH₂CH₃ | H | H | ortho |
| 57. | H | H | OCHF₂ | CH₂CH₃ | H | H | meta |
| 58. | CH₃ | H | OCHF₂ | CH₂CH₃ | H | H | meta |
| 59. | H | H | OCHF₂ | CH₂CH₃ | H | H | para |
| 60. | CH₃ | H | OCHF₂ | CH₂CH₃ | H | H | para |
| 61. | H | H | OCH₂CH₂F | CH₂CH₃ | H | H | ortho |
| 62. | CH₃ | H | OCH₂CH₂F | CH₂CH₃ | H | H | ortho |
| 63. | H | H | OCH₂CH₂F | CH₂CH₃ | H | H | meta |
| 64. | CH₃ | H | OCH₂CH₂F | CH₂CH₃ | H | H | meta |
| 65. | H | H | OCH₂CH₂F | CH₂CH₃ | H | H | para |
| 66. | CH₃ | H | OCH₂CH₂F | CH₂CH₃ | H | H | para |
| 67. | H | H | OCH₃ | CH₂CH₂CH₃ | H | H | ortho |
| 68. | CH₃ | H | OCH₃ | CH₂CH₂CH₃ | H | H | ortho |
| 69. | H | H | OCH₃ | CH₂CH₂CH₃ | H | H | meta |
| 70. | CH₃ | H | OCH₃ | CH₂CH₂CH₃ | H | H | meta |
| 71. | H | H | OCH₃ | CH₂CH₂CH₃ | H | H | para |
| 72. | CH₃ | H | OCH₃ | CH₂CH₂CH₃ | H | H | para |
| 73. | H | H | OCHF₂ | CH₂CH₂CH₃ | H | H | ortho |
| 74. | CH₃ | H | OCHF₂ | CH₂CH₂CH₃ | H | H | ortho |
| 75. | H | H | OCHF₂ | CH₂CH₂CH₃ | H | H | meta |
| 76. | CH₃ | H | OCHF₂ | CH₂CH₂CH₃ | H | H | meta |
| 77. | H | H | OCHF₂ | CH₂CH₂CH₃ | H | H | para |
| 78. | CH₃ | H | OCHF₂ | CH₂CH₂CH₃ | H | H | para |
| 79. | H | H | OCH₂CH₂F | CH₂CH₂CH₃ | H | H | ortho |
| 80. | CH₃ | H | OCH₂CH₂F | CH₂CH₂CH₃ | H | H | ortho |
| 81. | H | H | OCH₂CH₂F | CH₂CH₂CH₃ | H | H | meta |
| 82. | CH₃ | H | OCH₂CH₂F | CH₂CH₂CH₃ | H | H | meta |
| 83. | H | H | OCH₂CH₂F | CH₂CH₂CH₃ | H | H | para |
| 84. | CH₃ | H | OCH₂CH₂F | CH₂CH₂CH₃ | H | H | para |
| 85. | H | H | OCH₃ | H | 6-OCH₃ | H | meta |
| 86. | H | H | OCH₃ | CH₃ | 6-OCH₃ | H | meta |
| 87. | CH₃ | H | OCH₃ | H | 6-OCH₃ | H | meta |
| 88. | CH₃ | H | OCH₃ | CH₃ | 6-OCH₃ | H | meta |

TABLE A-continued

| No. | $R^1$ | $R^2$ | $R^3$ | $R^4$ | $R^{5*}$ | $R^{6**}$ | position of $OCHF_2$*** |
|---|---|---|---|---|---|---|---|
| 89. | H | H | $OCHF_2$ | H | 6-$OCH_3$ | H | meta |
| 90. | H | H | $OCHF_2$ | $CH_3$ | 6-$OCH_3$ | H | meta |
| 91. | $CH_3$ | H | $OCHF_2$ | H | 6-$OCH_3$ | H | meta |
| 92. | $CH_3$ | H | $OCHF_2$ | $CH_3$ | 6-$OCH_3$ | H | meta |
| 93. | H | H | $OCF_3$ | H | 6-$OCH_3$ | H | meta |
| 94. | H | H | $OCF_3$ | $CH_3$ | 6-$OCH_3$ | H | meta |
| 95. | $CH_3$ | H | $OCF_3$ | H | 6-$OCH_3$ | H | meta |
| 96. | $CH_3$ | H | $OCF_3$ | $CH_3$ | 6-$OCH_3$ | H | meta |
| 97. | H | H | $OCH_2CH_2F$ | H | 6-$OCH_3$ | H | meta |
| 98. | H | H | $OCH_2CH_2F$ | $CH_3$ | 6-$OCH_3$ | H | meta |
| 99. | $CH_3$ | H | $OCH_2CH_2F$ | H | 6-$OCH_3$ | H | meta |
| 100. | $CH_3$ | H | $OCH_2CH_2F$ | $CH_3$ | 6-$OCH_3$ | H | meta |
| 101. | H | H | $OCH_3$ | $CH_2CH_3$ | 6-$OCH_3$ | H | meta |
| 102. | $CH_3$ | H | $OCH_3$ | $CH_2CH_3$ | 6-$OCH_3$ | H | meta |
| 103. | H | H | $OCHF_2$ | $CH_2CH_3$ | 6-$OCH_3$ | H | meta |
| 104. | $CH_3$ | H | $OCHF_2$ | $CH_2CH_3$ | 6-$OCH_3$ | H | meta |
| 105. | H | H | $OCH_2CH_2F$ | $CH_2CH_3$ | 6-$OCH_3$ | H | meta |
| 106. | $CH_3$ | H | $OCH_2CH_2F$ | $CH_2CH_3$ | 6-$OCH_3$ | H | meta |
| 107. | H | H | $OCH_3$ | $CH_2CH_2CH_3$ | 6-$OCH_3$ | H | meta |
| 108. | $CH_3$ | H | $OCH_3$ | $CH_2CH_2CH_3$ | 6-$OCH_3$ | H | meta |
| 109. | H | H | $OCHF_2$ | $CH_2CH_2CH_3$ | 6-$OCH_3$ | H | meta |
| 110. | $CH_3$ | H | $OCHF_2$ | $CH_2CH_2CH_3$ | 6-$OCH_3$ | H | meta |
| 111. | H | H | $OCH_2CH_2F$ | $CH_2CH_2CH_3$ | 6-$OCH_3$ | H | meta |
| 112. | $CH_3$ | H | $OCH_2CH_2F$ | $CH_2CH_2CH_3$ | 6-$OCH_3$ | H | meta |
| 113. | H | H | $OCH_3$ | H | 6-$OCHF_2$ | H | meta |
| 114. | H | H | $OCH_3$ | $CH_3$ | 6-$OCHF_2$ | H | meta |
| 115. | $CH_3$ | H | $OCH_3$ | H | 6-$OCHF_2$ | H | meta |
| 116. | $CH_3$ | H | $OCH_3$ | $CH_3$ | 6-$OCHF_2$ | H | meta |
| 117. | H | H | $OCHF_2$ | H | 6-$OCHF_2$ | H | meta |
| 118. | H | H | $OCHF_2$ | $CH_3$ | 6-$OCHF_2$ | H | meta |
| 119. | $CH_3$ | H | $OCHF_2$ | H | 6-$OCHF_2$ | H | meta |
| 120. | $CH_3$ | H | $OCHF_2$ | $CH_3$ | 6-$OCHF_2$ | H | meta |
| 121. | H | H | $OCF_3$ | H | 6-$OCHF_2$ | H | meta |
| 122. | H | H | $OCF_3$ | $CH_3$ | 6-$OCHF_2$ | H | meta |
| 123. | $CH_3$ | H | $OCF_3$ | H | 6-$OCHF_2$ | H | meta |
| 124. | $CH_3$ | H | $OCF_3$ | $CH_3$ | 6-$OCHF_2$ | H | meta |
| 125. | H | H | $OCH_2CH_2F$ | H | 6-$OCHF_2$ | H | meta |
| 126. | H | H | $OCH_2CH_2F$ | $CH_3$ | 6-$OCHF_2$ | H | meta |
| 127. | $CH_3$ | H | $OCH_2CH_2F$ | H | 6-$OCHF_2$ | H | meta |
| 128. | $CH_3$ | H | $OCH_2CH_2F$ | $CH_3$ | 6-$OCHF_2$ | H | meta |
| 129. | H | H | $OCH_3$ | $CH_2CH_3$ | 6-$OCHF_2$ | H | meta |
| 130. | $CH_3$ | H | $OCH_3$ | $CH_2CH_3$ | 6-$OCHF_2$ | H | meta |
| 131. | H | H | $OCHF_2$ | $CH_2CH_3$ | 6-$OCHF_2$ | H | meta |
| 132. | $CH_3$ | H | $OCHF_2$ | $CH_2CH_3$ | 6-$OCHF_2$ | H | meta |
| 133. | H | H | $OCH_2CH_2F$ | $CH_2CH_3$ | 6-$OCHF_2$ | H | meta |
| 134. | $CH_3$ | H | $OCH_2CH_2F$ | $CH_2CH_3$ | 6-$OCHF_2$ | H | meta |
| 135. | H | H | $OCH_3$ | $CH_2CH_2CH_3$ | 6-$OCHF_2$ | H | meta |
| 136. | $CH_3$ | H | $OCH_3$ | $CH_2CH_2CH_3$ | 6-$OCHF_2$ | H | meta |
| 137. | H | H | $OCHF_2$ | $CH_2CH_2CH_3$ | 6-$OCHF_2$ | H | meta |
| 138. | $CH_3$ | H | $OCHF_2$ | $CH_2CH_2CH_3$ | 6-$OCHF_2$ | H | meta |
| 139. | H | H | $OCH_2CH_2F$ | $CH_2CH_2CH_3$ | 6-$OCHF_2$ | H | meta |
| 140. | $CH_3$ | H | $OCH_2CH_2F$ | $CH_2CH_2CH_3$ | 6-$OCHF_2$ | H | meta |
| 141. | H | H | $OCH_3$ | H | 4-$OCH_3$ | H | meta |
| 142. | H | H | $OCH_3$ | $CH_3$ | 4-$OCH_3$ | H | meta |
| 143. | $CH_3$ | H | $OCH_3$ | H | 4-$OCH_3$ | H | meta |
| 144. | $CH_3$ | H | $OCH_3$ | $CH_3$ | 4-$OCH_3$ | H | meta |
| 145. | H | H | $OCHF_2$ | H | 4-$OCH_3$ | H | meta |
| 146. | H | H | $OCHF_2$ | $CH_3$ | 4-$OCH_3$ | H | meta |
| 147. | $CH_3$ | H | $OCHF_2$ | H | 4-$OCH_3$ | H | meta |
| 148. | $CH_3$ | H | $OCHF_2$ | $CH_3$ | 4-$OCH_3$ | H | meta |
| 149. | H | H | $OCF_3$ | H | 4-$OCH_3$ | H | meta |
| 150. | H | H | $OCF_3$ | $CH_3$ | 4-$OCH_3$ | H | meta |
| 151. | $CH_3$ | H | $OCF_3$ | H | 4-$OCH_3$ | H | meta |
| 152. | $CH_3$ | H | $OCF_3$ | $CH_3$ | 4-$OCH_3$ | H | meta |
| 153. | H | H | $OCH_2CH_2F$ | H | 4-$OCH_3$ | H | meta |
| 154. | H | H | $OCH_2CH_2F$ | $CH_3$ | 4-$OCH_3$ | H | meta |
| 155. | $CH_3$ | H | $OCH_2CH_2F$ | H | 4-$OCH_3$ | H | meta |
| 156. | $CH_3$ | H | $OCH_2CH_2F$ | $CH_3$ | 4-$OCH_3$ | H | meta |
| 157. | H | H | $OCH_3$ | $CH_2CH_3$ | 4-$OCH_3$ | H | meta |
| 158. | $CH_3$ | H | $OCH_3$ | $CH_2CH_3$ | 4-$OCH_3$ | H | meta |
| 159. | H | H | $OCHF_2$ | $CH_2CH_3$ | 4-$OCH_3$ | H | meta |
| 160. | $CH_3$ | H | $OCHF_2$ | $CH_2CH_3$ | 4-$OCH_3$ | H | meta |
| 161. | H | H | $OCH_2CH_2F$ | $CH_2CH_3$ | 4-$OCH_3$ | H | meta |
| 162. | $CH_3$ | H | $OCH_2CH_2F$ | $CH_2CH_3$ | 4-$OCH_3$ | H | meta |
| 163. | H | H | $OCH_3$ | $CH_2CH_2CH_3$ | 4-$OCH_3$ | H | meta |
| 164. | $CH_3$ | H | $OCH_3$ | $CH_2CH_2CH_3$ | 4-$OCH_3$ | H | meta |
| 165. | H | H | $OCHF_2$ | $CH_2CH_2CH_3$ | 4-$OCH_3$ | H | meta |

TABLE A-continued

| No. | R¹ | R² | R³ | R⁴ | R⁵* | R⁶** | position of OCHF₂*** |
|---|---|---|---|---|---|---|---|
| 166. | CH₃ | H | OCHF₂ | CH₂CH₂CH₃ | 4-OCH₃ | H | meta |
| 167. | H | H | OCH₂CH₂F | CH₂CH₂CH₃ | 4-OCH₃ | H | meta |
| 168. | CH₃ | H | OCH₂CH₂F | CH₂CH₂CH₃ | 4-OCH₃ | H | meta |
| 169. | H | H | OCH₃ | H | 3-OCH₃ | H | para |
| 170. | H | H | OCH₃ | CH₃ | 3-OCH₃ | H | para |
| 171. | CH₃ | H | OCH₃ | H | 3-OCH₃ | H | para |
| 172. | CH₃ | H | OCH₃ | CH₃ | 3-OCH₃ | H | para |
| 173. | H | H | OCHF₂ | H | 3-OCH₃ | H | para |
| 174. | H | H | OCHF₂ | CH₃ | 3-OCH₃ | H | para |
| 175. | CH₃ | H | OCHF₂ | H | 3-OCH₃ | H | para |
| 176. | CH₃ | H | OCHF₂ | CH₃ | 3-OCH₃ | H | para |
| 177. | H | H | OCF₃ | H | 3-OCH₃ | H | para |
| 178. | H | H | OCF₃ | CH₃ | 3-OCH₃ | H | para |
| 179. | CH₃ | H | OCF₃ | H | 3-OCH₃ | H | para |
| 180. | CH₃ | H | OCF₃ | CH₃ | 3-OCH₃ | H | para |
| 181. | H | H | OCH₂CH₂F | H | 3-OCH₃ | H | para |
| 182. | H | H | OCH₂CH₂F | CH₃ | 3-OCH₃ | H | para |
| 183. | CH₃ | H | OCH₂CH₂F | H | 3-OCH₃ | H | para |
| 184. | CH₃ | H | OCH₂CH₂F | CH₃ | 3-OCH₃ | H | para |
| 185. | H | H | OCH₂CH₂F | CH₂CH₃ | 3-OCH₃ | H | para |
| 186. | CH₃ | H | OCH₂CH₂F | CH₂CH₃ | 3-OCH₃ | H | para |
| 187. | H | H | OCHF₂ | CH₂CH₃ | 3-OCH₃ | H | para |
| 188. | CH₃ | H | OCHF₂ | CH₂CH₃ | 3-OCH₃ | H | para |
| 189. | H | H | OCH₃ | CH₂CH₃ | 3-OCH₃ | H | para |
| 190. | CH₃ | H | OCH₃ | CH₂CH₃ | 3-OCH₃ | H | para |
| 191. | H | H | OCH₂CH₂F | CH₂CH₂CH₃ | 3-OCH₃ | H | para |
| 192. | CH₃ | H | OCH₂CH₂F | CH₂CH₂CH₃ | 3-OCH₃ | H | para |
| 193. | H | H | OCHF₂ | CH₂CH₂CH₃ | 3-OCH₃ | H | para |
| 194. | CH₃ | H | OCHF₂ | CH₂CH₂CH₃ | 3-OCH₃ | H | para |
| 195. | H | H | OCH₃ | CH₂CH₂CH₃ | 3-OCH₃ | H | para |
| 196. | CH₃ | H | OCH₃ | CH₂CH₂CH₃ | 3-OCH₃ | H | para |
| 197. | H | H | OCH₃ | H | H | 6-F | ortho |
| 198. | H | H | OCH₃ | CH₃ | H | 6-F | ortho |
| 199. | CH₃ | H | OCH₃ | H | H | 6-F | ortho |
| 200. | CH₃ | H | OCH₃ | CH₃ | H | 6-F | ortho |
| 201. | H | H | OCH₃ | H | H | 6-F | meta |
| 202. | H | H | OCH₃ | CH₃ | H | 6-F | meta |
| 203. | CH₃ | H | OCH₃ | H | H | 6-F | meta |
| 204. | CH₃ | H | OCH₃ | CH₃ | H | 6-F | meta |
| 205. | H | H | OCH₃ | H | H | 6-F | para |
| 206. | H | H | OCH₃ | CH₃ | H | 6-F | para |
| 207. | CH₃ | H | OCH₃ | H | H | 6-F | para |
| 208. | CH₃ | H | OCH₃ | CH₃ | H | 6-F | para |
| 209. | H | H | OCH₃ | CH₂CH₃ | H | 6-F | ortho |
| 210. | CH₃ | H | OCH₃ | CH₂CH₃ | H | 6-F | ortho |
| 211. | H | H | OCH₃ | CH₂CH₃ | H | 6-F | meta |
| 212. | CH₃ | H | OCH₃ | CH₂CH₃ | H | 6-F | meta |
| 213. | H | H | OCH₃ | CH₂CH₃ | H | 6-F | para |
| 214. | CH₃ | H | OCH₃ | CH₂CH₃ | H | 6-F | para |
| 215. | H | H | OCH₃ | CH₂CH₂CH₃ | H | 6-F | ortho |
| 216. | CH₃ | H | OCH₃ | CH₂CH₂CH₃ | H | 6-F | ortho |
| 217. | H | H | OCH₃ | CH₂CH₂CH₃ | H | 6-F | meta |
| 218. | CH₃ | H | OCH₃ | CH₂CH₂CH₃ | H | 6-F | meta |
| 219. | H | H | OCH₃ | CH₂CH₂CH₃ | H | 6-F | para |
| 220. | CH₃ | H | OCH₃ | CH₂CH₂CH₃ | H | 6-F | para |
| 221. | H | H | OCH₃ | H | 6-OCH₃ | 6-F | meta |
| 222. | CH₃ | H | OCH₃ | H | 6-OCH₃ | 6-F | meta |
| 223. | H | H | OCH₃ | CH₃ | 6-OCH₃ | 6-F | meta |
| 224. | CH₃ | H | OCH₃ | CH₃ | 6-OCH₃ | 6-F | meta |
| 225. | H | H | OCH₃ | CH₂CH₃ | 6-OCH₃ | 6-F | meta |
| 226. | CH₃ | H | OCH₃ | CH₂CH₃ | 6-OCH₃ | 6-F | meta |
| 227. | H | H | OCH₃ | CH₂CH₂CH₃ | 6-OCH₃ | 6-F | meta |
| 228. | CH₃ | H | OCH₃ | CH₂CH₂CH₃ | 6-OCH₃ | 6-F | meta |
| 229. | H | H | OCH₃ | H | 6-OCHF₂ | 6-F | meta |
| 230. | CH₃ | H | OCH₃ | H | 6-OCHF₂ | 6-F | meta |
| 231. | H | H | OCH₃ | CH₃ | 6-OCHF₂ | 6-F | meta |
| 232. | CH₃ | H | OCH₃ | CH₃ | 6-OCHF₂ | 6-F | meta |
| 233. | H | H | OCH₃ | CH₂CH₃ | 6-OCHF₂ | 6-F | meta |
| 234. | CH₃ | H | OCH₃ | CH₂CH₃ | 6-OCHF₂ | 6-F | meta |
| 235. | H | H | OCH₃ | CH₂CH₂CH₃ | 6-OCHF₂ | 6-F | meta |
| 236. | CH₃ | H | OCH₃ | CH₂CH₂CH₃ | 6-OCHF₂ | 6-F | meta |
| 237. | H | H | OCH₃ | H | 4-OCH₃ | 6-F | meta |
| 238. | CH₃ | H | OCH₃ | H | 4-OCH₃ | 6-F | meta |
| 239. | H | H | OCH₃ | CH₃ | 4-OCH₃ | 6-F | meta |
| 240. | CH₃ | H | OCH₃ | CH₃ | 4-OCH₃ | 6-F | meta |
| 241. | H | H | OCH₃ | CH₂CH₃ | 4-OCH₃ | 6-F | meta |
| 242. | CH₃ | H | OCH₃ | CH₂CH₃ | 4-OCH₃ | 6-F | meta |

TABLE A-continued

| No. | R¹ | R² | R³ | R⁴ | R⁵* | R⁶** | position of OCHF₂*** |
|---|---|---|---|---|---|---|---|
| 243. | H | H | OCH₃ | CH₂CH₂CH₃ | 4-OCH₃ | 6-F | meta |
| 244. | CH₃ | H | OCH₃ | CH₂CH₂CH₃ | 4-OCH₃ | 6-F | meta |
| 245. | H | H | OCH₃ | H | 3-OCH₃ | 6-F | para |
| 246. | CH₃ | H | OCH₃ | H | 3-OCH₃ | 6-F | para |
| 247. | H | H | OCH₃ | CH₃ | 3-OCH₃ | 6-F | para |
| 248. | CH₃ | H | OCH₃ | CH₃ | 3-OCH₃ | 6-F | para |
| 249. | H | H | OCH₃ | CH₂CH₃ | 3-OCH₃ | 6-F | para |
| 250. | CH₃ | H | OCH₃ | CH₂CH₃ | 3-OCH₃ | 6-F | para |
| 251. | H | H | OCH₃ | CH₂CH₂CH₃ | 3-OCH₃ | 6-F | para |
| 252. | CH₃ | H | OCH₃ | CH₂CH₂CH₃ | 3-OCH₃ | 6-F | para |
| 253. | H | H | OCH₃ | H | H | 5-F | ortho |
| 254. | H | H | OCH₃ | CH₃ | H | 5-F | ortho |
| 255. | CH₃ | H | OCH₃ | H | H | 5-F | ortho |
| 256. | CH₃ | H | OCH₃ | CH₃ | H | 5-F | ortho |
| 257. | H | H | OCH₃ | H | H | 5-F | meta |
| 258. | H | H | OCH₃ | CH₃ | H | 5-F | meta |
| 259. | CH₃ | H | OCH₃ | H | H | 5-F | meta |
| 260. | CH₃ | H | OCH₃ | CH₃ | H | 5-F | meta |
| 261. | H | H | OCH₃ | H | H | 5-F | para |
| 262. | H | H | OCH₃ | CH₃ | H | 5-F | para |
| 263. | CH₃ | H | OCH₃ | H | H | 5-F | para |
| 264. | CH₃ | H | OCH₃ | CH₃ | H | 5-F | para |
| 265. | H | H | OCH₃ | CH₂CH₃ | H | 5-F | ortho |
| 266. | CH₃ | H | OCH₃ | CH₂CH₃ | H | 5-F | ortho |
| 267. | H | H | OCH₃ | CH₂CH₃ | H | 5-F | meta |
| 268. | CH₃ | H | OCH₃ | CH₂CH₃ | H | 5-F | meta |
| 269. | H | H | OCH₃ | CH₂CH₃ | H | 5-F | para |
| 270. | CH₃ | H | OCH₃ | CH₂CH₃ | H | 5-F | para |
| 271. | H | H | OCH₃ | CH₂CH₂CH₃ | H | 5-F | ortho |
| 272. | CH₃ | H | OCH₃ | CH₂CH₂CH₃ | H | 5-F | ortho |
| 273. | H | H | OCH₃ | CH₂CH₂CH₃ | H | 5-F | meta |
| 274. | CH₃ | H | OCH₃ | CH₂CH₂CH₃ | H | 5-F | meta |
| 275. | H | H | OCH₃ | CH₂CH₂CH₃ | H | 5-F | para |
| 276. | CH₃ | H | OCH₃ | CH₂CH₂CH₃ | H | 5-F | para |
| 277. | H | H | OCH₃ | H | 6-OCH₃ | 5-F | meta |
| 278. | H | H | OCH₃ | CH₃ | 6-OCH₃ | 5-F | meta |
| 279. | CH₃ | H | OCH₃ | H | 6-OCH₃ | 5-F | meta |
| 280. | CH₃ | H | OCH₃ | CH₃ | 6-OCH₃ | 5-F | meta |
| 281. | H | H | OCH₃ | CH₂CH₃ | 6-OCH₃ | 5-F | meta |
| 282. | CH₃ | H | OCH₃ | CH₂CH₃ | 6-OCH₃ | 5-F | meta |
| 283. | H | H | OCH₃ | CH₂CH₂CH₃ | 6-OCH₃ | 5-F | meta |
| 284. | CH₃ | H | OCH₃ | CH₂CH₂CH₃ | 6-OCH₃ | 5-F | meta |
| 285. | H | H | OCH₃ | H | 6-OCHF₂ | 5-F | meta |
| 286. | H | H | OCH₃ | CH₃ | 6-OCHF₂ | 5-F | meta |
| 287. | CH₃ | H | OCH₃ | H | 6-OCHF₂ | 5-F | meta |
| 288. | CH₃ | H | OCH₃ | CH₃ | 6-OCHF₂ | 5-F | meta |
| 289. | H | H | OCH₃ | CH₂CH₃ | 6-OCHF₂ | 5-F | meta |
| 290. | CH₃ | H | OCH₃ | CH₂CH₃ | 6-OCHF₂ | 5-F | meta |
| 291. | H | H | OCH₃ | CH₂CH₂CH₃ | 6-OCHF₂ | 5-F | meta |
| 292. | CH₃ | H | OCH₃ | CH₂CH₂CH₃ | 6-OCHF₂ | 5-F | meta |
| 293. | H | H | OCH₃ | H | 4-OCH₃ | 5-F | meta |
| 294. | H | H | OCH₃ | CH₃ | 4-OCH₃ | 5-F | meta |
| 295. | CH₃ | H | OCH₃ | H | 4-OCH₃ | 5-F | meta |
| 296. | CH₃ | H | OCH₃ | CH₃ | 4-OCH₃ | 5-F | meta |
| 297. | H | H | OCH₃ | CH₂CH₃ | 4-OCH₃ | 5-F | meta |
| 298. | CH₃ | H | OCH₃ | CH₂CH₃ | 4-OCH₃ | 5-F | meta |
| 299. | H | H | OCH₃ | CH₂CH₂CH₃ | 4-OCH₃ | 5-F | meta |
| 300. | CH₃ | H | OCH₃ | CH₂CH₂CH₃ | 4-OCH₃ | 5-F | meta |
| 301. | H | H | OCH₃ | CH₂CH₃ | 3-OCH₃ | 5-F | para |
| 302. | CH₃ | H | OCH₃ | CH₂CH₃ | 3-OCH₃ | 5-F | para |
| 303. | H | H | OCH₃ | CH₂CH₂CH₃ | 3-OCH₃ | 5-F | para |
| 304. | CH₃ | H | OCH₃ | CH₂CH₂CH₃ | 3-OCH₃ | 5-F | para |
| 305. | H | H | OCH₃ | H | 3-OCH₃ | 5-F | para |
| 306. | H | H | OCH₃ | CH₃ | 3-OCH₃ | 5-F | para |
| 307. | CH₃ | H | OCH₃ | H | 3-OCH₃ | 5-F | para |
| 308. | CH₃ | H | OCH₃ | CH₃ | 3-OCH₃ | 5-F | para |
| 309. | H | H | H | H | H | 6-F | ortho |
| 310. | H | H | H | CH₃ | H | 6-F | ortho |
| 311. | CH₃ | H | H | H | H | 6-F | ortho |
| 312. | CH₃ | H | H | CH₃ | H | 6-F | ortho |
| 313. | H | H | H | H | H | 6-F | meta |
| 314. | H | H | H | CH₃ | H | 6-F | meta |
| 315. | CH₃ | H | H | H | H | 6-F | meta |
| 316. | CH₃ | H | H | CH₃ | H | 6-F | meta |
| 317. | H | H | H | H | H | 6-F | para |
| 318. | H | H | H | CH₃ | H | 6-F | para |
| 319. | CH₃ | H | H | H | H | 6-F | para |

TABLE A-continued

| No. | R¹ | R² | R³ | R⁴ | R⁵* | R⁶** | position of OCHF₂*** |
|---|---|---|---|---|---|---|---|
| 320. | CH₃ | H | H | CH₃ | H | 6-F | para |
| 321. | H | H | H | CH₂CH₃ | H | 6-F | ortho |
| 322. | CH₃ | H | H | CH₂CH₃ | H | 6-F | ortho |
| 323. | H | H | H | CH₂CH₃ | H | 6-F | meta |
| 324. | CH₃ | H | H | CH₂CH₃ | H | 6-F | meta |
| 325. | H | H | H | CH₂CH₃ | H | 6-F | para |
| 326. | CH₃ | H | H | CH₂CH₃ | H | 6-F | para |
| 327. | H | H | H | CH₂CH₂CH₃ | H | 6-F | ortho |
| 328. | CH₃ | H | H | CH₂CH₂CH₃ | H | 6-F | ortho |
| 329. | H | H | H | CH₂CH₂CH₃ | H | 6-F | meta |
| 330. | CH₃ | H | H | CH₂CH₂CH₃ | H | 6-F | meta |
| 331. | H | H | H | CH₂CH₂CH₃ | H | 6-F | para |
| 332. | CH₃ | H | H | CH₂CH₂CH₃ | H | 6-F | para |
| 333. | H | H | H | H | 6-OCH₃ | 6-F | meta |
| 334. | H | H | H | CH₃ | 6-OCH₃ | 6-F | meta |
| 335. | CH₃ | H | H | H | 6-OCH₃ | 6-F | meta |
| 336. | CH₃ | H | H | CH₃ | 6-OCH₃ | 6-F | meta |
| 337. | H | H | H | CH₂CH₃ | 6-OCH₃ | 6-F | meta |
| 338. | CH₃ | H | H | CH₂CH₃ | 6-OCH₃ | 6-F | meta |
| 339. | H | H | H | CH₂CH₂CH₃ | 6-OCH₃ | 6-F | meta |
| 340. | CH₃ | H | H | CH₂CH₂CH₃ | 6-OCH₃ | 6-F | meta |
| 341. | H | H | H | H | 6-OCHF₂ | 6-F | meta |
| 342. | H | H | H | CH₃ | 6-OCHF₂ | 6-F | meta |
| 343. | CH₃ | H | H | H | 6-OCHF₂ | 6-F | meta |
| 344. | CH₃ | H | H | CH₃ | 6-OCHF₂ | 6-F | meta |
| 345. | H | H | H | CH₂CH₃ | 6-OCHF₂ | 6-F | meta |
| 346. | CH₃ | H | H | CH₂CH₃ | 6-OCHF₂ | 6-F | meta |
| 347. | H | H | H | CH₂CH₂CH₃ | 6-OCHF₂ | 6-F | meta |
| 348. | CH₃ | H | H | CH₂CH₂CH₃ | 6-OCHF₂ | 6-F | meta |
| 349. | H | H | H | H | 4-OCH₃ | 6-F | meta |
| 350. | H | H | H | CH₃ | 4-OCH₃ | 6-F | meta |
| 351. | CH₃ | H | H | H | 4-OCH₃ | 6-F | meta |
| 352. | CH₃ | H | H | CH₃ | 4-OCH₃ | 6-F | meta |
| 353. | H | H | H | CH₂CH₃ | 4-OCH₃ | 6-F | meta |
| 354. | CH₃ | H | H | CH₂CH₃ | 4-OCH₃ | 6-F | meta |
| 355. | H | H | H | CH₂CH₃ | 3-OCH₃ | 6-F | para |
| 356. | CH₃ | H | H | CH₂CH₃ | 3-OCH₃ | 6-F | para |
| 357. | H | H | H | CH₂CH₂CH₃ | 4-OCH₃ | 6-F | meta |
| 358. | CH₃ | H | H | CH₂CH₂CH₃ | 4-OCH₃ | 6-F | meta |
| 359. | H | H | H | CH₂CH₂CH₃ | 3-OCH₃ | 6-F | para |
| 360. | CH₃ | H | H | CH₂CH₂CH₃ | 3-OCH₃ | 6-F | para |
| 361. | H | H | H | H | 3-OCH₃ | 6-F | para |
| 362. | H | H | H | CH₃ | 3-OCH₃ | 6-F | para |
| 363. | CH₃ | H | H | H | 3-OCH₃ | 6-F | para |
| 364. | CH₃ | H | H | CH₃ | 3-OCH₃ | 6-F | para |
| 365. | H | H | H | H | H | 5-F | ortho |
| 366. | H | H | H | CH₃ | H | 5-F | ortho |
| 367. | CH₃ | H | H | H | H | 5-F | ortho |
| 368. | CH₃ | H | H | CH₃ | H | 5-F | ortho |
| 369. | H | H | H | H | H | 5-F | meta |
| 370. | H | H | H | CH₃ | H | 5-F | meta |
| 371. | CH₃ | H | H | H | H | 5-F | meta |
| 372. | CH₃ | H | H | CH₃ | H | 5-F | meta |
| 373. | H | H | H | H | H | 5-F | para |
| 374. | H | H | H | CH₃ | H | 5-F | para |
| 375. | CH₃ | H | H | H | H | 5-F | para |
| 376. | CH₃ | H | H | CH₃ | H | 5-F | para |
| 377. | H | H | H | CH₂CH₃ | H | 5-F | ortho |
| 378. | CH₃ | H | H | CH₂CH₃ | H | 5-F | ortho |
| 379. | H | H | H | CH₂CH₃ | H | 5-F | meta |
| 380. | CH₃ | H | H | CH₂CH₃ | H | 5-F | meta |
| 381. | H | H | H | CH₂CH₃ | H | 5-F | para |
| 382. | CH₃ | H | H | CH₂CH₃ | H | 5-F | para |
| 383. | H | H | H | CH₂CH₂CH₃ | H | 5-F | ortho |
| 384. | CH₃ | H | H | CH₂CH₂CH₃ | H | 5-F | ortho |
| 385. | H | H | H | CH₂CH₂CH₃ | H | 5-F | meta |
| 386. | CH₃ | H | H | CH₂CH₂CH₃ | H | 5-F | meta |
| 387. | H | H | H | CH₂CH₂CH₃ | H | 5-F | para |
| 388. | CH₃ | H | H | CH₂CH₂CH₃ | H | 5-F | para |
| 389. | H | H | H | H | 6-OCH₃ | 5-F | meta |
| 390. | H | H | H | CH₃ | 6-OCH₃ | 5-F | meta |
| 391. | CH₃ | H | H | H | 6-OCH₃ | 5-F | meta |
| 392. | CH₃ | H | H | CH₃ | 6-OCH₃ | 5-F | meta |
| 393. | H | H | H | CH₂CH₃ | 6-OCH₃ | 5-F | meta |
| 394. | CH₃ | H | H | CH₂CH₃ | 6-OCH₃ | 5-F | meta |

TABLE A-continued

| No. | R$^1$ | R$^2$ | R$^3$ | R$^4$ | R$^5$* | R$^6$** | position of OCHF$_2$*** |
|---|---|---|---|---|---|---|---|
| 395. | H | H | H | CH$_2$CH$_2$CH$_3$ | 6-OCH$_3$ | 5-F | meta |
| 396. | CH$_3$ | H | H | CH$_2$CH$_2$CH$_3$ | 6-OCH$_3$ | 5-F | meta |
| 397. | H | H | H | H | 6-OCHF$_2$ | 5-F | meta |
| 398. | H | H | H | CH$_3$ | 6-OCHF$_2$ | 5-F | meta |
| 399. | CH$_3$ | H | H | H | 6-OCHF$_2$ | 5-F | meta |
| 400. | CH$_3$ | H | H | CH$_3$ | 6-OCHF$_2$ | 5-F | meta |
| 401. | H | H | H | CH$_2$CH$_3$ | 6-OCHF$_2$ | 5-F | meta |
| 402. | CH$_3$ | H | H | CH$_2$CH$_3$ | 6-OCHF$_2$ | 5-F | meta |
| 403. | H | H | H | CH$_2$CH$_2$CH$_3$ | 6-OCHF$_2$ | 5-F | meta |
| 404. | CH$_3$ | H | H | CH$_2$CH$_2$CH$_3$ | 6-OCHF$_2$ | 5-F | meta |
| 405. | H | H | H | H | 4-OCH$_3$ | 5-F | meta |
| 406. | H | H | H | CH$_3$ | 4-OCH$_3$ | 5-F | meta |
| 407. | CH$_3$ | H | H | H | 4-OCH$_3$ | 5-F | meta |
| 408. | CH$_3$ | H | H | CH$_3$ | 4-OCH$_3$ | 5-F | meta |
| 409. | H | H | H | CH$_2$CH$_3$ | 4-OCH$_3$ | 5-F | meta |
| 410. | CH$_3$ | H | H | CH$_2$CH$_3$ | 4-OCH$_3$ | 5-F | meta |
| 411. | H | H | H | CH$_2$CH$_3$ | 3-OCH$_3$ | 5-F | para |
| 412. | CH$_3$ | H | H | CH$_2$CH$_3$ | 3-OCH$_3$ | 5-F | para |
| 413. | H | H | H | CH$_2$CH$_2$CH$_3$ | 4-OCH$_3$ | 5-F | meta |
| 414. | CH$_3$ | H | H | CH$_2$CH$_2$CH$_3$ | 4-OCH$_3$ | 5-F | meta |
| 415. | H | H | H | CH$_2$CH$_2$CH$_3$ | 3-OCH$_3$ | 5-F | para |
| 416. | CH$_3$ | H | H | CH$_2$CH$_2$CH$_3$ | 3-OCH$_3$ | 5-F | para |
| 417. | H | H | H | H | 3-OCH$_3$ | 5-F | para |
| 418. | H | H | H | CH$_3$ | 3-OCH$_3$ | 5-F | para |
| 419. | CH$_3$ | H | H | H | 3-OCH$_3$ | 5-F | para |
| 420. | CH$_3$ | H | H | CH$_3$ | 3-OCH$_3$ | 5-F | para |
| 421. | H | H | H | H | H | H | ortho |
| 422. | H | H | H | CH$_3$ | H | H | ortho |
| 423. | CH$_3$ | H | H | H | H | H | ortho |
| 424. | CH$_3$ | H | H | CH$_3$ | H | H | ortho |
| 425. | H | H | H | H | H | H | meta |
| 426. | H | H | H | CH$_3$ | H | H | meta |
| 427. | CH$_3$ | H | H | H | H | H | meta |
| 428. | CH$_3$ | H | H | CH$_3$ | H | H | meta |
| 429. | H | H | H | H | H | H | para |
| 430. | H | H | H | CH$_3$ | H | H | para |
| 431. | CH$_3$ | H | H | H | H | H | para |
| 432. | CH$_3$ | H | H | CH$_3$ | H | H | para |
| 433. | H | H | H | CH$_2$CH$_3$ | H | H | ortho |
| 434. | CH$_3$ | H | H | CH$_2$CH$_3$ | H | H | ortho |
| 435. | H | H | H | CH$_2$CH$_3$ | H | H | meta |
| 436. | CH$_3$ | H | H | CH$_2$CH$_3$ | H | H | meta |
| 437. | H | H | H | CH$_2$CH$_3$ | H | H | para |
| 438. | CH$_3$ | H | H | CH$_2$CH$_3$ | H | H | para |
| 439. | H | H | H | CH$_2$CH$_2$CH$_3$ | H | H | ortho |
| 440. | CH$_3$ | H | H | CH$_2$CH$_2$CH$_3$ | H | H | ortho |
| 441. | H | H | H | CH$_2$CH$_2$CH$_3$ | H | H | meta |
| 442. | CH$_3$ | H | H | CH$_2$CH$_2$CH$_3$ | H | H | meta |
| 443. | H | H | H | CH$_2$CH$_2$CH$_3$ | H | H | para |
| 444. | CH$_3$ | H | H | CH$_2$CH$_2$CH$_3$ | H | H | para |
| 445. | H | H | H | H | 6-OCH$_3$ | H | meta |
| 446. | H | H | H | CH$_3$ | 6-OCH$_3$ | H | meta |
| 447. | CH$_3$ | H | H | H | 6-OCH$_3$ | H | meta |
| 448. | CH$_3$ | H | H | CH$_3$ | 6-OCH$_3$ | H | meta |
| 449. | H | H | H | CH$_2$CH$_3$ | 6-OCH$_3$ | H | meta |
| 450. | CH$_3$ | H | H | CH$_2$CH$_3$ | 6-OCH$_3$ | H | meta |
| 451. | H | H | H | CH$_2$CH$_2$CH$_3$ | 6-OCH$_3$ | H | meta |
| 452. | CH$_3$ | H | H | CH$_2$CH$_2$CH$_3$ | 6-OCH$_3$ | H | meta |
| 453. | H | H | H | H | 6-OCHF$_2$ | H | meta |
| 454. | H | H | H | CH$_3$ | 6-OCHF$_2$ | H | meta |
| 455. | CH$_3$ | H | H | H | 6-OCHF$_2$ | H | meta |
| 456. | CH$_3$ | H | H | CH$_3$ | 6-OCHF$_2$ | H | meta |
| 457. | H | H | H | CH$_2$CH$_3$ | 6-OCHF$_2$ | H | meta |
| 458. | CH$_3$ | H | H | CH$_2$CH$_3$ | 6-OCHF$_2$ | H | meta |
| 459. | H | H | H | CH$_2$CH$_2$CH$_3$ | 6-OCHF$_2$ | H | meta |
| 460. | CH$_3$ | H | H | CH$_2$CH$_2$CH$_3$ | 6-OCHF$_2$ | H | meta |
| 461. | H | H | H | H | 4-OCH$_3$ | H | meta |
| 462. | H | H | H | CH$_3$ | 4-OCH$_3$ | H | meta |
| 463. | CH$_3$ | H | H | H | 4-OCH$_3$ | H | meta |
| 464. | CH$_3$ | H | H | CH$_3$ | 4-OCH$_3$ | H | meta |
| 465. | H | H | H | CH$_2$CH$_3$ | 4-OCH$_3$ | H | meta |
| 466. | CH$_3$ | H | H | CH$_2$CH$_3$ | 4-OCH$_3$ | H | meta |
| 467. | H | H | H | CH$_2$CH$_2$CH$_3$ | 4-OCH$_3$ | H | meta |
| 468. | CH$_3$ | H | H | CH$_2$CH$_2$CH$_3$ | 4-OCH$_3$ | H | meta |
| 469. | H | H | H | H | 3-OCH$_3$ | H | para |

TABLE A-continued

| No. | $R^1$ | $R^2$ | $R^3$ | $R^4$ | $R^{5*}$ | $R^{6**}$ | position of $OCHF_2$*** |
|---|---|---|---|---|---|---|---|
| 470. | H | H | H | $CH_3$ | 3-$OCH_3$ | H | para |
| 471. | $CH_3$ | H | H | H | 3-$OCH_3$ | H | para |
| 472. | $CH_3$ | H | H | $CH_3$ | 3-$OCH_3$ | H | para |
| 473. | H | H | H | $CH_2CH_3$ | 3-$OCH_3$ | H | para |
| 474. | $CH_3$ | H | H | $CH_2CH_3$ | 3-$OCH_3$ | H | para |
| 475. | H | H | H | $CH_2CH_2CH_3$ | 3-$OCH_3$ | H | para |
| 476. | $CH_3$ | H | H | $CH_2CH_2CH_3$ | 3-$OCH_3$ | H | para |
| 477. | H | H | F | H | H | H | ortho |
| 478. | H | H | F | $CH_3$ | H | H | ortho |
| 479. | $CH_3$ | H | F | H | H | H | ortho |
| 480. | $CH_3$ | H | F | $CH_3$ | H | H | ortho |
| 481. | H | H | F | H | H | H | meta |
| 482. | H | H | F | $CH_3$ | H | H | meta |
| 483. | $CH_3$ | H | F | H | H | H | meta |
| 484. | $CH_3$ | H | F | $CH_3$ | H | H | meta |
| 485. | H | H | F | H | H | H | para |
| 486. | H | H | F | $CH_3$ | H | H | para |
| 487. | $CH_3$ | H | F | H | H | H | para |
| 488. | $CH_3$ | H | F | $CH_3$ | H | H | para |
| 489. | H | H | F | $CH_2CH_3$ | H | H | ortho |
| 490. | $CH_3$ | H | F | $CH_2CH_3$ | H | H | ortho |
| 491. | H | H | F | $CH_2CH_3$ | H | H | meta |
| 492. | $CH_3$ | H | F | $CH_2CH_3$ | H | H | meta |
| 493. | H | H | F | $CH_2CH_3$ | H | H | para |
| 494. | $CH_3$ | H | F | $CH_2CH_3$ | H | H | para |
| 495. | H | H | F | $CH_2CH_2CH_3$ | H | H | ortho |
| 496. | $CH_3$ | H | F | $CH_2CH_2CH_3$ | H | H | ortho |
| 497. | H | H | F | $CH_2CH_2CH_3$ | H | H | meta |
| 498. | $CH_3$ | H | F | $CH_2CH_2CH_3$ | H | H | meta |
| 499. | H | H | F | $CH_2CH_2CH_3$ | H | H | para |
| 500. | $CH_3$ | H | F | $CH_2CH_2CH_3$ | H | H | para |
| 501. | H | H | F | H | 6-$OCH_3$ | H | meta |
| 502. | H | H | F | $CH_3$ | 6-$OCH_3$ | H | meta |
| 503. | $CH_3$ | H | F | H | 6-$OCH_3$ | H | meta |
| 504. | $CH_3$ | H | F | $CH_3$ | 6-$OCH_3$ | H | meta |
| 505. | H | H | F | $CH_2CH_3$ | 6-$OCH_3$ | H | meta |
| 506. | $CH_3$ | H | F | $CH_2CH_3$ | 6-$OCH_3$ | H | meta |
| 507. | H | H | F | $CH_2CH_2CH_3$ | 6-$OCH_3$ | H | meta |
| 508. | $CH_3$ | H | F | $CH_2CH_2CH_3$ | 6-$OCH_3$ | H | meta |
| 509. | H | H | F | H | 6-$OCHF_2$ | H | meta |
| 510. | H | H | F | $CH_3$ | 6-$OCHF_2$ | H | meta |
| 511. | $CH_3$ | H | F | H | 6-$OCHF_2$ | H | meta |
| 512. | $CH_3$ | H | F | $CH_3$ | 6-$OCHF_2$ | H | meta |
| 513. | H | H | F | $CH_2CH_3$ | 6-$OCHF_2$ | H | meta |
| 514. | $CH_3$ | H | F | $CH_2CH_3$ | 6-$OCHF_2$ | H | meta |
| 515. | H | H | F | $CH_2CH_2CH_3$ | 6-$OCHF_2$ | H | meta |
| 516. | $CH_3$ | H | F | $CH_2CH_2CH_3$ | 6-$OCHF_2$ | H | meta |
| 517. | H | H | F | H | 4-$OCH_3$ | H | meta |
| 518. | H | H | F | $CH_3$ | 4-$OCH_3$ | H | meta |
| 519. | $CH_3$ | H | F | H | 4-$OCH_3$ | H | meta |
| 520. | $CH_3$ | H | F | $CH_3$ | 4-$OCH_3$ | H | meta |
| 521. | H | H | F | $CH_2CH_3$ | 4-$OCH_3$ | H | meta |
| 522. | $CH_3$ | H | F | $CH_2CH_3$ | 4-$OCH_3$ | H | meta |
| 523. | H | H | F | $CH_2CH_3$ | 3-$OCH_3$ | H | para |
| 524. | $CH_3$ | H | F | $CH_2CH_3$ | 3-$OCH_3$ | H | para |
| 525. | H | H | F | $CH_2CH_2CH_3$ | 4-$OCH_3$ | H | meta |
| 526. | $CH_3$ | H | F | $CH_2CH_2CH_3$ | 4-$OCH_3$ | H | meta |
| 527. | H | H | F | $CH_2CH_2CH_3$ | 3-$OCH_3$ | H | para |
| 528. | $CH_3$ | H | F | $CH_2CH_2CH_3$ | 3-$OCH_3$ | H | para |
| 529. | H | H | F | H | 3-$OCH_3$ | H | para |
| 530. | H | H | F | $CH_3$ | 3-$OCH_3$ | H | para |
| 531. | $CH_3$ | H | F | H | 3-$OCH_3$ | H | para |
| 532. | $CH_3$ | H | F | $CH_3$ | 3-$OCH_3$ | H | para |

*position with respect to the sulfonyl moiety
**position as indicated in formula I
***position with respect to the sulfonyl moiety (ortho = 2-position, meta = 3-position, para = 4-position)

Examples of compounds according to the present invention are the compounds of the formula I', their pharmacologically tolerated salts and the N-oxides thereof, wherein $R^5$ is hydrogen and wherein $R^1$, $R^2$, $R^3$, $R^4$ and $R^6$ is given in the following table B and wherein the sulfonyl group is attached to the benzene ring at the α-position with respect to the dioxole ring:

TABLE B (I')

|  | R¹ | R² | R³ | R⁴ | R⁶ ** |
|---|---|---|---|---|---|
| 533. | H | H | OCH₃ | H | H |
| 534. | H | H | OCH₃ | CH₃ | H |
| 535. | CH₃ | H | OCH₃ | H | H |
| 536. | CH₃ | H | OCH₃ | CH₃ | H |
| 537. | H | H | OCHF₂ | H | H |
| 538. | H | H | OCHF₂ | CH₃ | H |
| 539. | CH₃ | H | OCHF₂ | H | H |
| 540. | CH₃ | H | OCHF₂ | CH₃ | H |
| 541. | H | H | OCF₃ | H | H |
| 542. | H | H | OCF₃ | CH₃ | H |
| 543. | CH₃ | H | OCF₃ | H | H |
| 544. | CH₃ | H | OCF₃ | CH₃ | H |
| 545. | H | H | OCH₂CH₂F | H | H |
| 546. | H | H | OCH₂CH₂F | CH₃ | H |
| 547. | CH₃ | H | OCH₂CH₂F | H | H |
| 548. | CH₃ | H | OCH₂CH₂F | CH₃ | H |
| 549. | H | CH₃ (rac) | OCH₃ | H | H |
| 550. | H | CH₃ (rac) | OCH₃ | CH₃ | H |
| 551. | CH₃ | CH₃ (rac) | OCH₃ | H | H |
| 552. | CH₃ | CH₃ (rac) | OCH₃ | CH₃ | H |
| 553. | H | CH₃ (rac) | OCHF₂ | H | H |
| 554. | H | CH₃ (rac) | OCHF₂ | CH₃ | H |
| 555. | CH₃ | CH₃ (rac) | OCHF₂ | H | H |
| 556. | CH₃ | CH₃ (rac) | OCHF₂ | CH₃ | H |
| 557. | H | CH₃ (rac) | OCF₃ | H | H |
| 558. | H | CH₃ (rac) | OCF₃ | CH₃ | H |
| 559. | CH₃ | CH₃ (rac) | OCF₃ | H | H |
| 560. | CH₃ | CH₃ (rac) | OCF₃ | CH₃ | H |
| 561. | H | CH₃ (rac) | OCH₂CH₂F | H | H |
| 562. | H | CH₃ (rac) | OCH₂CH₂F | CH₃ | H |
| 563. | CH₃ | CH₃ (rac) | OCH₂CH₂F | H | H |
| 564. | CH₃ | CH₃ (rac) | OCH₂CH₂F | CH₃ | H |
| 565. | H | CH₃ (S) | OCH₃ | H | H |
| 566. | CH₃ | CH₃ (S) | OCH₃ | H | H |
| 567. | CH₃ | CH₃ (S) | OCH₃ | CH₃ | H |
| 568. | H | CH₃ (S) | OCHF₂ | CH₃ | H |
| 569. | H | CH₃ (S) | OCHF₂ | CH₃ | H |
| 570. | CH₃ | CH₃ (S) | OCHF₂ | H | H |
| 571. | CH₃ | CH₃ (S) | OCHF₂ | CH₃ | H |
| 572. | H | CH₃ (S) | OCF₃ | H | H |
| 573. | H | CH₃ (S) | OCF₃ | CH₃ | H |
| 574. | CH₃ | CH₃ (S) | OCF₃ | H | H |
| 575. | CH₃ | CH₃ (S) | OCF₃ | CH₃ | H |
| 576. | H | CH₃ (S) | OCH₂CH₂F | H | H |
| 577. | H | CH₃ (S) | OCH₂CH₂F | CH₃ | H |
| 578. | CH₃ | CH₃ (S) | OCH₂CH₂F | H | H |
| 579. | CH₃ | CH₃ (S) | OCH₂CH₂F | CH₃ | H |
| 580. | H | CH₃ (R) | OCH₃ | CH₃ | H |
| 581. | CH₃ | CH₃ (R) | OCH₃ | H | H |
| 582. | CH₃ | CH₃ (R) | OCH₃ | CH₃ | H |
| 583. | H | CH₃ (R) | OCHF₂ | H | H |
| 584. | H | CH₃ (R) | OCHF₂ | CH₃ | H |
| 585. | CH₃ | CH₃ (R) | OCHF₂ | H | H |
| 586. | CH₃ | CH₃ (R) | OCHF₂ | CH₃ | H |
| 587. | H | CH₃ (R) | OCF₃ | H | H |
| 588. | H | CH₃ (R) | OCF₃ | CH₃ | H |
| 589. | CH₃ | CH₃ (R) | OCF₃ | H | H |
| 590. | CH₃ | CH₃ (R) | OCF₃ | CH₃ | H |
| 591. | H | CH₃ (R) | OCH₂CH₂F | H | H |
| 592. | H | CH₃ (R) | OCH₂CH₂F | CH₃ | H |
| 593. | CH₃ | CH₃ (R) | OCH₂CH₂F | H | H |
| 594. | CH₃ | CH₃ (R) | OCH₂CH₂F | CH₃ | H |
| 595. | H | H | OCH₃ | C₂H₅ | H |
| 596. | CH₃ | H | OCH₃ | C₂H₅ | H |
| 597. | H | H | OCHF₂ | C₂H₅ | H |
| 598. | CH₃ | H | OCHF₂ | C₂H₅ | H |
| 599. | H | H | OCF₃ | C₂H₅ | H |
| 600. | CH₃ | H | OCF₃ | C₂H₅ | H |
| 601. | H | H | OCH₂CH₂F | C₂H₅ | H |
| 602. | CH₃ | H | OCH₂CH₂F | C₂H₅ | H |
| 603. | H | CH₃ (rac) | OCH₃ | C₂H₅ | H |
| 604. | CH₃ | CH₃ (rac) | OCH₃ | C₂H₅ | H |
| 605. | H | CH₃ (rac) | OCHF₂ | C₂H₅ | H |
| 606. | CH₃ | CH₃ (rac) | OCHF₂ | C₂H₅ | H |
| 607. | H | CH₃ (rac) | OCF₃ | C₂H₅ | H |
| 608. | CH₃ | CH₃ (rac) | OCF₃ | C₂H₅ | H |
| 609. | H | CH₃ (rac) | OCH₂CH₂F | C₂H₅ | H |
| 610. | CH₃ | CH₃ (rac) | OCH₂CH₂F | C₂H₅ | H |
| 611. | H | CH₃ (S) | OCH₃ | C₂H₅ | H |
| 612. | CH₃ | CH₃ (S) | OCH₃ | C₂H₅ | H |
| 613. | H | CH₃ (S) | OCHF₂ | C₂H₅ | H |
| 614. | CH₃ | CH₃ (S) | OCHF₂ | C₂H₅ | H |
| 615. | H | CH₃ (S) | OCF₃ | C₂H₅ | H |
| 616. | CH₃ | CH₃ (S) | OCF₃ | C₂H₅ | H |
| 617. | H | CH₃ (S) | OCH₂CH₂F | C₂H₅ | H |
| 618. | CH₃ | CH₃ (S) | OCH₂CH₂F | C₂H₅ | H |
| 619. | H | CH₃ (R) | OCH₃ | C₂H₅ | H |
| 620. | CH₃ | CH₃ (R) | OCH₃ | C₂H₅ | H |
| 621. | H | CH₃ (R) | OCHF₂ | C₂H₅ | H |
| 622. | CH₃ | CH₃ (R) | OCHF₂ | C₂H₅ | H |
| 623. | H | CH₃ (R) | OCF₃ | C₂H₅ | H |
| 624. | CH₃ | CH₃ (R) | OCF₃ | C₂H₅ | H |
| 625. | H | CH₃ (R) | OCH₂CH₂F | C₂H₅ | H |
| 626. | CH₃ | CH₃ (R) | OCH₂CH₂F | C₂H₅ | H |
| 627. | H | H | OCH₃ | CH₂CH₂CH₃ | H |
| 628. | CH₃ | H | OCH₃ | CH₂CH₂CH₃ | H |
| 629. | H | H | OCHF₂ | CH₂CH₂CH₃ | H |
| 630. | CH₃ | H | OCHF₂ | CH₂CH₂CH₃ | H |
| 631. | H | H | OCF₃ | CH₂CH₂CH₃ | H |
| 632. | CH₃ | H | OCF₃ | CH₂CH₂CH₃ | H |
| 633. | H | H | OCH₂CH₂F | CH₂CH₂CH₃ | H |
| 634. | CH₃ | H | OCH₂CH₂F | CH₂CH₂CH₃ | H |
| 635. | H | CH₃ (rac) | OCH₃ | CH₂CH₂CH₃ | H |
| 636. | CH₃ | CH₃ (rac) | OCH₃ | CH₂CH₂CH₃ | H |
| 637. | H | CH₃ (rac) | OCHF₂ | CH₂CH₂CH₃ | H |
| 638. | CH₃ | CH₃ (rac) | OCHF₂ | CH₂CH₂CH₃ | H |
| 639. | H | CH₃ (rac) | OCF₃ | CH₂CH₂CH₃ | H |
| 640. | CH₃ | CH₃ (rac) | OCF₃ | CH₂CH₂CH₃ | H |
| 641. | H | CH₃ (rac) | OCH₂CH₂F | CH₂CH₂CH₃ | H |
| 642. | CH₃ | CH₃ (rac) | OCH₂CH₂F | CH₂CH₂CH₃ | H |
| 643. | H | CH₃ (S) | OCH₃ | CH₂CH₂CH₃ | H |
| 644. | CH₃ | CH₃ (S) | OCH₃ | CH₂CH₂CH₃ | H |
| 645. | H | CH₃ (S) | OCHF₂ | CH₂CH₂CH₃ | H |
| 646. | CH₃ | CH₃ (S) | OCHF₂ | CH₂CH₂CH₃ | H |
| 647. | H | CH₃ (S) | OCF₃ | CH₂CH₂CH₃ | H |
| 648. | CH₃ | CH₃ (S) | OCF₃ | CH₂CH₂CH₃ | H |
| 649. | H | CH₃ (S) | OCH₂CH₂F | CH₂CH₂CH₃ | H |
| 650. | CH₃ | CH₃ (S) | OCH₂CH₂F | CH₂CH₂CH₃ | H |
| 651. | H | CH₃ (R) | OCH₃ | CH₂CH₂CH₃ | H |
| 652. | CH₃ | CH₃ (R) | OCH₃ | CH₂CH₂CH₃ | H |
| 653. | H | CH₃ (R) | OCHF₂ | CH₂CH₂CH₃ | H |
| 654. | CH₃ | CH₃ (R) | OCHF₂ | CH₂CH₂CH₃ | H |
| 655. | H | CH₃ (R) | OCF₃ | CH₂CH₂CH₃ | H |
| 656. | CH₃ | CH₃ (R) | OCF₃ | CH₂CH₂CH₃ | H |
| 657. | H | CH₃ (R) | OCH₂CH₂F | CH₂CH₂CH₃ | H |
| 658. | CH₃ | CH₃ (R) | OCH₂CH₂F | CH₂CH₂CH₃ | H |
| 659. | H | H | OCH₃ | H | 6-F |
| 660. | H | H | OCH₃ | CH₃ | 6-F |
| 661. | CH₃ | H | OCH₃ | H | 6-F |
| 662. | CH₃ | H | OCH₃ | CH₃ | 6-F |

TABLE B-continued (I')

|  | R¹ | R² | R³ | R⁴ | R⁶ ** |
|---|---|---|---|---|---|
| 663. | H | CH₃ (rac) | OCH₃ | H | 6-F |
| 664. | H | CH₃ (rac) | OCH₃ | CH₃ | 6-F |
| 665. | CH₃ | CH₃ (rac) | OCH₃ | H | 6-F |
| 666. | CH₃ | CH₃ (rac) | OCH₃ | CH₃ | 6-F |
| 667. | H | CH₃ (S) | OCH₃ | H | 6-F |
| 668. | H | CH₃ (S) | OCH₃ | CH₃ | 6-F |
| 669. | CH₃ | CH₃ (S) | OCH₃ | CH₃ | 6-F |
| 670. | H | CH₃ (R) | OCH₃ | CH₃ | 6-F |
| 671. | CH₃ | CH₃ (R) | OCH₃ | H | 6-F |
| 672. | CH₃ | CH₃ (R) | OCH₃ | CH₃ | 6-F |
| 673. | H | H | OCH₃ | C₂H₅ | 6-F |
| 674. | CH₃ | H | OCH₃ | C₂H₅ | 6-F |
| 675. | H | CH₃ (rac) | OCH₃ | C₂H₅ | 6-F |
| 676. | CH₃ | CH₃ (rac) | OCH₃ | C₂H₅ | 6-F |
| 677. | H | CH₃ (S) | OCH₃ | C₂H₅ | 6-F |
| 678. | CH₃ | CH₃ (S) | OCH₃ | C₂H₅ | 6-F |
| 679. | H | CH₃ (R) | OCH₃ | C₂H₅ | 6-F |
| 680. | CH₃ | CH₃ (R) | OCH₃ | C₂H₅ | 6-F |
| 681. | H | H | OCH₃ | CH₂CH₂CH₃ | 6-F |
| 682. | CH₃ | H | OCH₃ | CH₂CH₂CH₃ | 6-F |
| 683. | H | CH₃ (rac) | OCH₃ | CH₂CH₂CH₃ | 6-F |
| 684. | CH₃ | CH₃ (rac) | OCH₃ | CH₂CH₂CH₃ | 6-F |
| 685. | H | CH₃ (S) | OCH₃ | CH₂CH₂CH₃ | 6-F |
| 686. | CH₃ | CH₃ (S) | OCH₃ | CH₂CH₂CH₃ | 6-F |
| 687. | H | CH₃ (R) | OCH₃ | CH₂CH₂CH₃ | 6-F |
| 688. | CH₃ | CH₃ (R) | OCH₃ | CH₂CH₂CH₃ | 6-F |
| 689. | H | H | OCH₃ | H | 5-F |
| 690. | H | H | OCH₃ | CH₃ | 5-F |
| 691. | CH₃ | H | OCH₃ | H | 5-F |
| 692. | CH₃ | H | OCH₃ | CH₃ | 5-F |
| 693. | H | CH₃ (rac) | OCH₃ | H | 5-F |
| 694. | H | CH₃ (rac) | OCH₃ | CH₃ | 5-F |
| 695. | CH₃ | CH₃ (rac) | OCH₃ | H | 5-F |
| 696. | CH₃ | CH₃ (rac) | OCH₃ | CH₃ | 5-F |
| 697. | H | CH₃ (S) | OCH₃ | CH₃ | 5-F |
| 698. | CH₃ | CH₃ (S) | OCH₃ | H | 5-F |
| 699. | CH₃ | CH₃ (S) | OCH₃ | CH₃ | 5-F |
| 700. | H | CH₃ (R) | OCH₃ | CH₃ | 5-F |
| 701. | CH₃ | CH₃ (R) | OCH₃ | H | 5-F |
| 702. | CH₃ | CH₃ (R) | OCH₃ | CH₃ | 5-F |
| 703. | H | H | OCH₃ | C₂H₅ | 5-F |
| 704. | CH₃ | H | OCH₃ | C₂H₅ | 5-F |
| 705. | H | CH₃ (rac) | OCH₃ | C₂H₅ | 5-F |
| 706. | CH₃ | CH₃ (rac) | OCH₃ | C₂H₅ | 5-F |
| 707. | H | CH₃ (S) | OCH₃ | C₂H₅ | 5-F |
| 708. | CH₃ | CH₃ (S) | OCH₃ | C₂H₅ | 5-F |
| 709. | H | CH₃ (R) | OCH₃ | C₂H₅ | 5-F |
| 710. | CH₃ | CH₃ (R) | OCH₃ | C₂H₅ | 5-F |
| 711. | H | H | OCH₃ | CH₂CH₂CH₃ | 5-F |
| 712. | CH₃ | H | OCH₃ | CH₂CH₂CH₃ | 5-F |
| 713. | H | CH₃ (rac) | OCH₃ | CH₂CH₂CH₃ | 5-F |
| 714. | CH₃ | CH₃ (rac) | OCH₃ | CH₂CH₂CH₃ | 5-F |
| 715. | H | CH₃ (S) | OCH₃ | CH₂CH₂CH₃ | 5-F |
| 716. | CH₃ | CH₃ (S) | OCH₃ | CH₂CH₂CH₃ | 5-F |
| 717. | H | CH₃ (R) | OCH₃ | CH₂CH₂CH₃ | 5-F |
| 718. | CH₃ | CH₃ (R) | OCH₃ | CH₂CH₂CH₃ | 5-F |
| 719. | H | H | H | H | 6-F |
| 720. | H | H | H | CH₃ | 6-F |
| 721. | CH₃ | H | H | H | 6-F |
| 722. | CH₃ | H | H | CH₃ | 6-F |
| 723. | H | CH₃ (rac) | H | H | 6-F |
| 724. | H | CH₃ (rac) | H | CH₃ | 6-F |
| 725. | CH₃ | CH₃ (rac) | H | H | 6-F |
| 726. | CH₃ | CH₃ (rac) | H | CH₃ | 6-F |
| 727. | H | CH₃ (S) | H | CH₃ | 6-F |
| 728. | CH₃ | CH₃ (S) | H | H | 6-F |
| 729. | CH₃ | CH₃ (S) | H | CH₃ | 6-F |
| 730. | H | CH₃ (R) | H | CH₃ | 6-F |
| 731. | CH₃ | CH₃ (R) | H | H | 6-F |
| 732. | CH₃ | CH₃ (R) | H | CH₃ | 6-F |
| 733. | H | H | H | C₂H₅ | 6-F |
| 734. | CH₃ | H | H | C₂H₅ | 6-F |
| 735. | H | CH₃ (rac) | H | C₂H₅ | 6-F |
| 736. | CH₃ | CH₃ (rac) | H | C₂H₅ | 6-F |
| 737. | H | CH₃ (S) | H | C₂H₅ | 6-F |
| 738. | CH₃ | CH₃ (S) | H | C₂H₅ | 6-F |
| 739. | H | CH₃ (R) | H | C₂H₅ | 6-F |
| 740. | CH₃ | CH₃ (R) | H | C₂H₅ | 6-F |
| 741. | H | H | H | CH₂CH₂CH₃ | 6-F |
| 742. | CH₃ | H | H | CH₂CH₂CH₃ | 6-F |
| 743. | H | CH₃ (rac) | H | CH₂CH₂CH₃ | 6-F |
| 744. | CH₃ | CH₃ (rac) | H | CH₂CH₂CH₃ | 6-F |
| 745. | H | CH₃ (S) | H | CH₂CH₂CH₃ | 6-F |
| 746. | CH₃ | CH₃ (S) | H | CH₂CH₂CH₃ | 6-F |
| 747. | H | CH₃ (R) | H | CH₂CH₂CH₃ | 6-F |
| 748. | CH₃ | CH₃ (R) | H | CH₂CH₂CH₃ | 6-F |
| 749. | H | H | H | H | 5-F |
| 750. | H | H | H | CH₃ | 5-F |
| 751. | CH₃ | H | H | H | 5-F |
| 752. | CH₃ | H | H | CH₃ | 5-F |
| 753. | H | CH₃ (rac) | H | H | 5-F |
| 754. | H | CH₃ (rac) | H | CH₃ | 5-F |
| 755. | CH₃ | CH₃ (rac) | H | H | 5-F |
| 756. | CH₃ | CH₃ (rac) | H | CH₃ | 5-F |
| 757. | H | CH₃ (S) | H | CH₃ | 5-F |
| 758. | CH₃ | CH₃ (S) | H | H | 5-F |
| 759. | CH₃ | CH₃ (S) | H | CH₃ | 5-F |
| 760. | H | CH₃ (R) | H | CH₃ | 5-F |
| 761. | CH₃ | CH₃ (R) | H | H | 5-F |
| 762. | CH₃ | CH₃ (R) | H | CH₃ | 5-F |
| 763. | H | H | H | C₂H₅ | 5-F |
| 764. | CH₃ | H | H | C₂H₅ | 5-F |
| 765. | H | CH₃ (rac) | H | C₂H₅ | 5-F |
| 766. | CH₃ | CH₃ (rac) | H | C₂H₅ | 5-F |
| 767. | H | CH₃ (S) | H | C₂H₅ | 5-F |
| 768. | CH₃ | CH₃ (S) | H | C₂H₅ | 5-F |
| 769. | H | CH₃ (R) | H | C₂H₅ | 5-F |
| 770. | CH₃ | CH₃ (R) | H | C₂H₅ | 5-F |
| 771. | H | H | H | CH₂CH₂CH₃ | 5-F |
| 772. | CH₃ | H | H | CH₂CH₂CH₃ | 5-F |
| 773. | H | CH₃ (rac) | H | CH₂CH₂CH₃ | 5-F |
| 774. | CH₃ | CH₃ (rac) | H | CH₂CH₂CH₃ | 5-F |
| 775. | H | CH₃ (S) | H | CH₂CH₂CH₃ | 5-F |
| 776. | CH₃ | CH₃ (S) | H | CH₂CH₂CH₃ | 5-F |
| 777. | H | CH₃ (R) | H | CH₂CH₂CH₃ | 5-F |
| 778. | CH₃ | CH₃ (R) | H | CH₂CH₂CH₃ | 5-F |
| 779. | H | H | H | H | H |
| 780. | H | H | H | CH₃ | H |
| 781. | CH₃ | H | H | H | H |
| 782. | CH₃ | H | H | CH₃ | H |
| 783. | H | CH₃ (rac) | H | H | H |
| 784. | H | CH₃ (rac) | H | CH₃ | H |
| 785. | CH₃ | CH₃ (rac) | H | H | H |
| 786. | CH₃ | CH₃ (rac) | H | CH₃ | H |
| 787. | H | CH₃ (S) | H | CH₃ | H |
| 788. | CH₃ | CH₃ (S) | H | H | H |
| 789. | CH₃ | CH₃ (S) | H | CH₃ | H |
| 790. | H | CH₃ (R) | H | CH₃ | H |
| 791. | CH₃ | CH₃ (R) | H | H | H |
| 792. | CH₃ | CH₃ (R) | H | CH₃ | H |

TABLE B-continued (I')

|  | R¹ | R² | R³ | R⁴ | R⁶ ** |
|---|---|---|---|---|---|
| 793. | H | H | H | $C_2H_5$ | H |
| 794. | $CH_3$ | H | H | $C_2H_5$ | H |
| 795. | H | $CH_3$ (rac) | H | $C_2H_5$ | H |
| 796. | $CH_3$ | $CH_3$ (rac) | H | $C_2H_5$ | H |
| 797. | H | $CH_3$ (S) | H | $C_2H_5$ | H |
| 798. | $CH_3$ | $CH_3$ (S) | H | $C_2H_5$ | H |
| 799. | H | $CH_3$ (R) | H | $C_2H_5$ | H |
| 800. | $CH_3$ | $CH_3$ (R) | H | $C_2H_5$ | H |
| 801. | H | H | H | $CH_2CH_2CH_3$ | H |
| 802. | $CH_3$ | H | H | $CH_2CH_2CH_3$ | H |
| 803. | H | $CH_3$ (rac) | H | $CH_2CH_2CH_3$ | H |
| 804. | $CH_3$ | $CH_3$ (rac) | H | $CH_2CH_2CH_3$ | H |
| 805. | H | $CH_3$ (S) | H | $CH_2CH_2CH_3$ | H |
| 806. | $CH_3$ | $CH_3$ (S) | H | $CH_2CH_2CH_3$ | H |
| 807. | H | $CH_3$ (R) | H | $CH_2CH_2CH_3$ | H |
| 808. | $CH_3$ | $CH_3$ (R) | H | $CH_2CH_2CH_3$ | H |
| 809. | H | H | F | H | H |
| 810. | H | H | F | $CH_3$ | H |
| 811. | $CH_3$ | H | F | H | H |
| 812. | $CH_3$ | H | F | $CH_3$ | H |
| 813. | H | $CH_3$ (rac) | F | H | H |
| 814. | H | $CH_3$ (rac) | F | $CH_3$ | H |
| 815. | $CH_3$ | $CH_3$ (rac) | F | H | H |
| 816. | $CH_3$ | $CH_3$ (rac) | F | $CH_3$ | H |
| 817. | H | $CH_3$ (S) | F | $CH_3$ | H |
| 818. | $CH_3$ | $CH_3$ (S) | F | H | H |
| 819. | $CH_3$ | $CH_3$ (S) | F | $CH_3$ | H |
| 820. | H | $CH_3$ (R) | F | $CH_3$ | H |
| 821. | $CH_3$ | $CH_3$ (R) | F | H | H |
| 822. | $CH_3$ | $CH_3$ (R) | F | $CH_3$ | H |
| 823. | H | H | F | $C_2H_5$ | H |
| 824. | $CH_3$ | H | F | $C_2H_5$ | H |
| 825. | H | $CH_3$ (rac) | F | $C_2H_5$ | H |
| 826. | $CH_3$ | $CH_3$ (rac) | F | $C_2H_5$ | H |
| 827. | H | $CH_3$ (S) | F | $C_2H_5$ | H |
| 828. | $CH_3$ | $CH_3$ (S) | F | $C_2H_5$ | H |
| 829. | H | $CH_3$ (R) | F | $C_2H_5$ | H |
| 830. | $CH_3$ | $CH_3$ (R) | F | $C_2H_5$ | H |
| 831. | H | H | F | $CH_2CH_2CH_3$ | H |
| 832. | $CH_3$ | H | F | $CH_2CH_2CH_3$ | H |
| 833. | H | $CH_3$ (rac) | F | $CH_2CH_2CH_3$ | H |
| 834. | $CH_3$ | $CH_3$ (rac) | F | $CH_2CH_2CH_3$ | H |
| 835. | H | $CH_3$ (S) | F | $CH_2CH_2CH_3$ | H |
| 836. | $CH_3$ | $CH_3$ (S) | F | $CH_2CH_2CH_3$ | H |
| 837. | H | $CH_3$ (R) | F | $CH_2CH_2CH_3$ | H |
| 838. | $CH_3$ | $CH_3$ (R) | F | $CH_2CH_2CH_3$ | H | rac: racemic with respect to CH—R²
S: S-enantiomer with respect to CH—R²
S: R-enantiomer with respect to CH—R²
** position as indicated in formula I'

Examples of compounds according to the present invention are likewise the compounds of the formula I', their pharmacologically tolerated salts and the N-oxides thereof, wherein $R^1$, $R^2$, $R^3$, $R^4$ is given in table B and wherein the sulfonyl group is attached to the benzene ring at the β-position with respect to the dioxole ring.

The compounds I and I' according to the invention are prepared in analogy with methods known from the literature. An important approach to the compounds according to the invention is offered by the reaction of a 1-(piperazin-1-yl)-3-aminobenzene compound II with a difluoromethoxy benzenesulfonic acid derivative III as depicted in scheme 1 or with a 2,2-difluorobenzo[1,3]dioxolesulfonic acid derivative IIIa as depicted in scheme 1a.

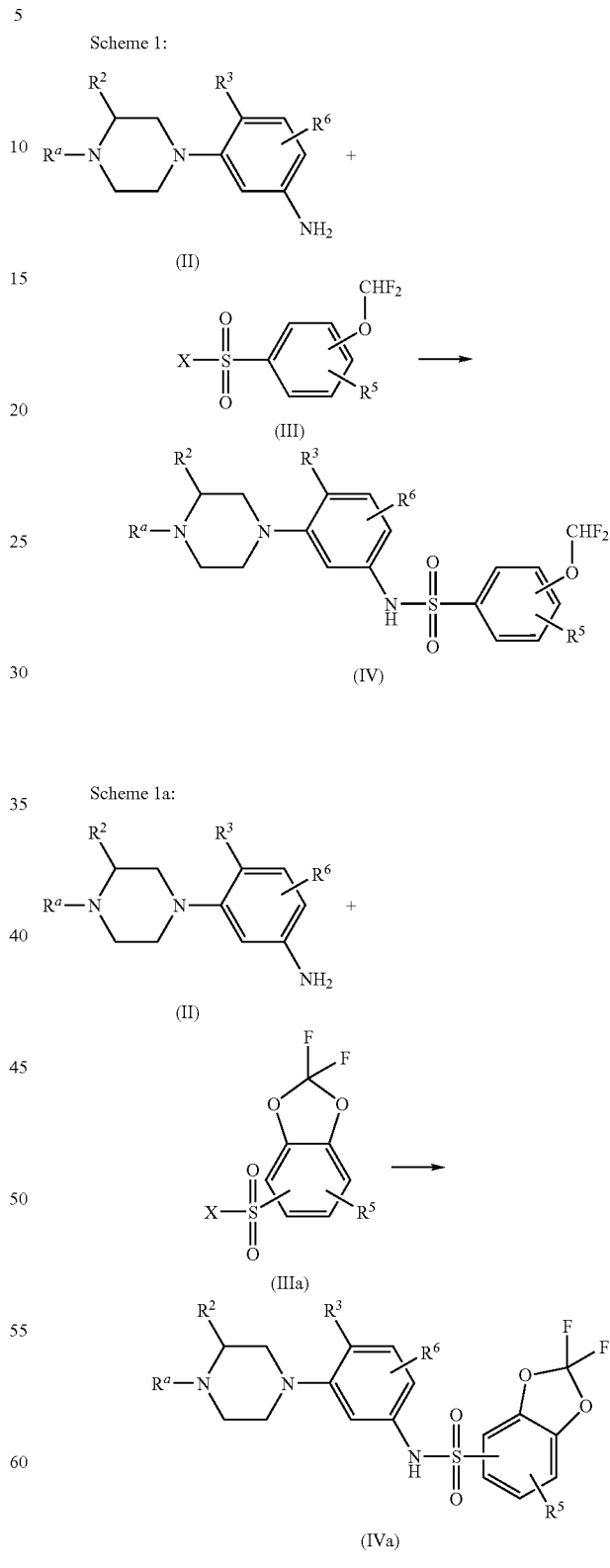

Scheme 1:

Scheme 1a:

In schemes 1 and 1a, $R^2$, $R^3$, $R^5$ and $R^6$ have the previously mentioned meanings. $R^a$ is a nitrogen protecting group or methyl Suitable N-protecting groups are described, for example, in P. J. Kocienski "Protecting Groups", 2$^{nd}$ ed., Georg Thieme Verlag, Stuttgart 2000, pp 186-237 and in the literature cited therein. Preferred examples of N-protecting groups are e.g., oxycarbonyl groups such as $C_1$-$C_6$-alkoxycarbonyl, e.g., methoxycarbonyl, ethoxycarbonyl and Boc (tert-butoxycarbonyl) and other oxycarbonyl groups such as benzyloxycarbonyl (Cbz), allyloxycarbonyl, 9-fluorenylmethoxycarbonyl (Fmoc) and 2-Trim ethylsilylethoxycarbonyl (Teoc), or 2-propenyl (allyl). X is a nucleophilically displaceable leaving group, in particular a halogen atom and, especially, chlorine or bromine.

Compounds of the formulae IV and IVa, wherein $R^a$ is a nitrogen protecting group, in particular a $C_1$-$C_6$-alkoxycarbonyl group such as methoxycarbonyl, ethoxycarbonyl and Boc (tert-butoxycarbonyl), are novel and thus form also part of the present invention.

Compounds of the formula IV, wherein $R^a$ is linear methyl correspond to compounds I, wherein $R^1$ is methyl. Compounds of the formula IVa, wherein $R^a$ is linear methyl correspond to compounds I', wherein $R^1$ is methyl.

The reaction depicted in schemes 1 and 1a takes place under the reaction conditions which are customary for preparing arylsulfonamide compounds or arylsulfonic esters, respectively, and which are described, for example, in J. March, Advanced Organic Chemistry, 3$^{rd}$ edition, John Wiley & Sons, New York, 1985 p 444 and the literature cited therein, European J. Org. Chem. 2002 (13), pp. 2094-2108, Tetrahedron 2001, 57 (27) pp. 5885-5895, Bioorganic and Medicinal Chemistry Letters, 2000, 10(8), pp. 835-838 and Synthesis 2000 (1), pp. 103-108.

The reaction customarily takes place in an inert solvent, for example in an ether, such as diethyl ether, diisopropyl ether, methyl tert-butyl ether or tetrahydrofuran, a halohydrocarbon, such as dichloromethane, an aliphatic or cycloaliphatic hydrocarbon, such as pentane, hexane or cyclohexane, or an aromatic hydrocarbon, such as toluene, xylene, cumene and the like, or in a mixture of the abovementioned solvents.

The reaction of compound II with compound III (or compound IIIa) is customarily carried out in the presence of an auxiliary base. Suitable bases are inorganic bases, such as sodium carbonate or potassium carbonate, or sodium hydrogen carbonate or potassium hydrogen carbonate, and organic bases, for example trialkylamines, such as triethylamine, or pyridine compounds, such as pyridine, lutidine and the like. The latter compounds can at the same time serve as solvents. The auxiliary base is customarily employed in at least equimolar quantities, based on the amine compound II.

The reaction of compound II with compound III or IIIa, respectively yields compound IV or IVa, respectively, which, in case $R^a$ is an N-protecting group, is deprotected to yield the compound of the general formula I or I', wherein $R^1$ is hydrogen. Deprotection of the compound IV or IVa, respectively, can be achieved by standard methods, e.g., by the methods as described in P. J. Kocienski "Protecting Groups", 2$^{nd}$ ed., Georg Thieme Verlag, Stuttgart 2000, pp 186-237 and in the literature cited therein.

Customary methods can then be used to react these compounds with an methylating agent such as methyliodide or dimethylsulfate resulting in a compound I or I', respectively, in which $R^1$ is $C_1$-$C_3$-alkyl or fluorinated $C_1$-$C_3$-alkyl. The reaction conditions which are required for this methylating reaction are disclosed, for example, in WO 02/83652, Tetrahedron 2000, 56(38) pp. 7553-7560 and Synlett. 2000 (4), pp. 475-480.

Likewise, it is possible to react the compound IV or IVa with a methylating agent such as methyliodide or dimethylsulfate to yield a compound of the formula IVc or IVd, respectively, wherein $R^a$, $R^2$, $R^3$, $R^5$ and $R^6$ are as defined above.

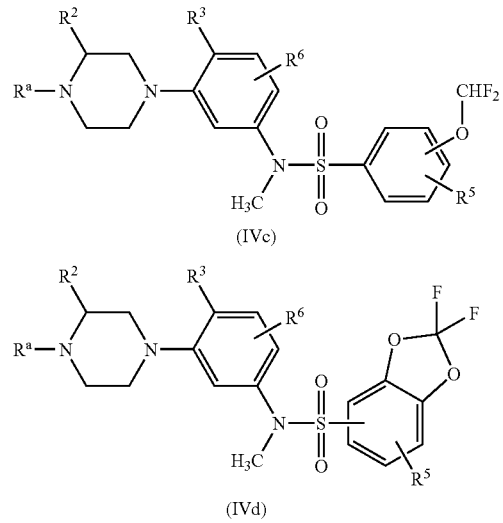

(IVc)

(IVd)

If $R^a$ in formulae IVb or IVd is an N-protecting group, compound IVc or IVd, respectively is deprotected to yield the compound of the general formula I, wherein $R^1$ is hydrogen. Deprotection of the compound IVc or IVd can be achieved by standard methods, e.g., by the methods as described in P. J. Kocienski "Protecting Groups", 2$^{nd}$ ed., Georg Thieme Verlag, Stuttgart 2000, pp 186-237 and in the literature cited therein.

The compounds of the general formula II are known per se or can be prepared in the manner shown in scheme 2.

Scheme 2:

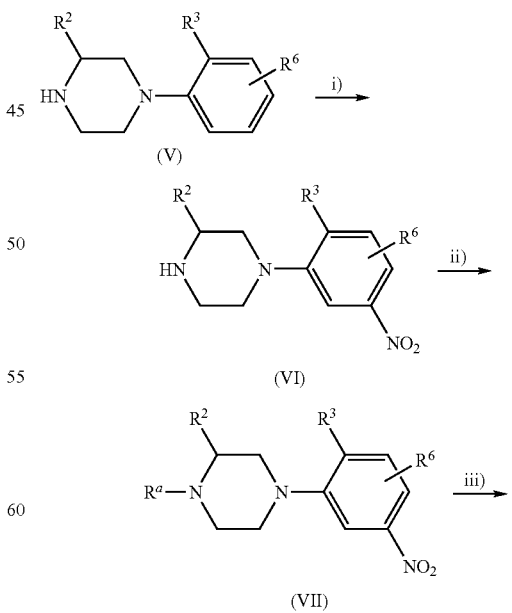

(V)

(VI)

(VII)

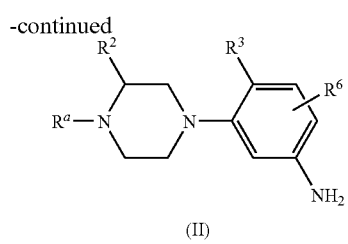

(II)

In scheme 2, $R^a$, $R^2$, $R^3$ and $R^6$ have the previously mentioned meanings.

In step i) of scheme 2, the compound V is subjected to a nitration under standard conditions thereby yielding compound VI. Reaction conditions can be taken e.g., from U.S. Pat. No. 6,599,904 or from the working examples of the present application.

In step ii) of scheme 2, the NH-group of compound VI is protected, either by a conventional N-protecting group as defined above or by introducing a methyl group via a methylating agent such as methylbromide, methyliodide or dimethylsulfate. Introduction of an N-protecting group into compound V can be achieved by standard methods, e.g., by the methods as described in P. J. Kocienski "Protecting Groups", $2^{nd}$ ed., Georg Thieme Verlag, Stuttgart 2000, pp 186-237 and in the literature cited therein. Methylation of compound VI is likewise achieved by standard methods of Organic chemistry.

In step iii), the nitro group in compound VII is reduced to the $NH_2$ group to yield compound II. The reaction conditions which are required for step b) correspond to the customary conditions for reducing aromatic nitro groups which have been described extensively in the literature (see, for example, J. March, Advanced Organic Chemistry, 3rd ed., J. Wiley & Sons, New-York, 1985, p. 1183 and the literature cited in this reference). The reduction can be achieved, for example, by reacting the nitro compound VII with a metal such as iron, zinc or tin under acidic reaction conditions, i.e., using nascent hydrogen, or using a complex hydride such as lithium aluminum hydride or sodium borohydride, preferably in the presence of transition metal compounds of nickel or cobalt such as $NiCl_2(P(phenyl)_3)_2$, or $CoCl_2$, (see Ono et al. Chem. Ind. (London), 1983 p. 480), or using $NaBH_2S_3$ (see Lalancette et al. Can. J. Chem. 49, 1971, p. 2990), with it being possible to carry out these reductions, depending on the given reagent, in substance or in a solvent or diluent. Alternatively, the reduction of VII to II can be carried out with hydrogen in the presence of a transition metal catalyst, e.g., using hydrogen in the presence of catalysts based on platinum, palladium, nickel, ruthenium or rhodium. The catalysts can contain the transition metal in elemental form or in the form of a complex compound, of a salt or of an oxide of the transition metal, with it being possible, for the purpose of modifying the activity, to use customary coligands, e.g., organic phosphine compounds, such as triphenylphosphine, tricyclohexylphosphine or tri-n-butylphosphines or phosphites. The catalyst is customarily employed in quantities of from 0.001 to 1 mol per mol of compound VI, calculated as catalyst metal. In a preferred variant, the reduction is effected using tin(II) chloride in analogy with the methods described in Bioorganic and Medicinal Chemistry Letters, 2002, 12(15), pp. 1917-1919 and J. Med. Chem. 2002, 45(21), pp. 4679-4688. The reaction of VII with tin(II) chloride is preferably carried out in an inert organic solvent, preferably an alcohol such as methanol, ethanol, isopropanol or butanol.

The compounds II, wherein $R^3$ is trifluoromethoxy, can be prepared according to the following synthetic scheme 3 from the commercially available bromo-trifluoromethoxy-nitrobenzene via Pd-catalyzed Buchwald-Hartwig coupling with e.g., a protected piperazine derivative and subsequent reduction of the nitro group to the amino group as described for step iii) in scheme 2.

Scheme 3:

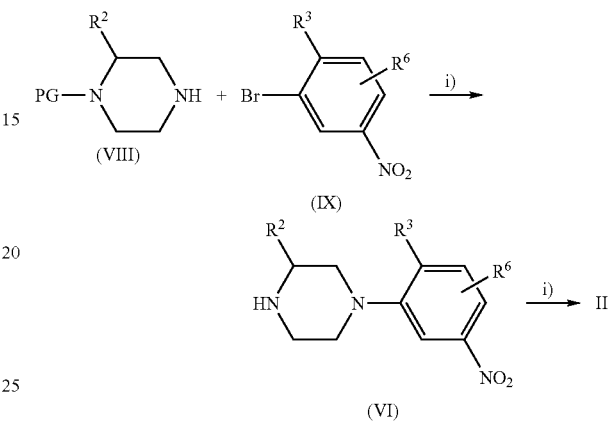

The compounds of the formula IX, wherein $R^3$ is difluoromethoxy can be prepared by reacting commercially available 2-bromo-4-nitrophenol with 2-chloro-2,2-difluoroacetophenone by analogy to the method described in J. Hu et al., J. Org. Chem., 2006, 71, 9845 to yield 2-bromo-1-difluoromethoxy-4-nitro-benzene, which is then convertied into the compound of the formula II with $R^3$ being difluoromethoxy by analogy to the methods depicted in schemes 2 and 3.

The compounds of the formula II, wherein $R^3$ is methoxy and $R^6$ is fluorine, can also be prepared according to scheme 3 from the commercially available 1-bromo-fluoro-2-methoxy-5-nitrobenzene via Pd-catalyzed Buchwald-Hartwig coupling with e.g., a protected piperazine derivative and subsequent reduction of the nitro group to the amino group as described for step iii) in scheme 2.

If not indicated otherwise, the above-described reactions are generally carried out in a solvent at temperatures between room temperature and the boiling temperature of the solvent employed. Alternatively, the activation energy which is required for the reaction can be introduced into the reaction mixture using microwaves, something which has proved to be of value, in particular, in the case of the reactions catalyzed by transition metals (with regard to reactions using microwaves, see Tetrahedron 2001, 57, p. 9199 ff. p. 9225 ff. and also, in a general manner, "Microwaves in Organic Synthesis", Andre Loupy (Ed.), Wiley-VCH 2002.

The acid addition salts of compounds I and I' are prepared in a customary manner by mixing the free base with a corresponding acid, where appropriate in solution in an organic solvent, for example acetonitrile, a lower alcohol, such as methanol, ethanol or propanol, an ether, such as diethyl ether, methyl tert-butyl ether or diisopropyl ether, a ketone, such as acetone or methyl ethyl ketone, an ester, such as ethyl acetate, mixtures thereof as well as mixtures thereof with water.

The compounds of the present invention can be a 5-$HT_6$ receptor agonist, including partial agonistic activity, or a 5-$HT_6$ receptor antagonist, including inverse agonist activity.

The compounds of formulae I and I' according to the present invention, as well as their salts and their N-oxides, have a surprisingly high affinity for $5\text{-}HT_6$ receptors. The high affinity of the compounds according to the invention for $5\text{-}HT_6$ receptors is reflected in very low in-vitro receptor binding constants ($K_i(5\text{-}HT_6)$ values) of as a rule less than 50 nM (nmol/l), preferably of less than 10 nM and, in particular of less than 5 nM. The displacement of $^3H$-LSD can, for example, be used in receptor binding studies for determining binding affinities to $5\text{-}HT_6$ receptors.

Furthermore the compounds of formulae I and I', as well as their salts and their N-oxides, are highly selective $5\text{-}HT_6$ receptor ligands which, because of their low affinity for other receptors such as dopamine receptors, adrenergic receptors, muscarinic receptors, histamine receptors, opiate receptors, in particular dopamine $D_2$, $\alpha_1$-adrenergic and histamine $H_1$ receptors, give rise to fewer side-effects than other, less selective $5\text{-}HT_6$ ligands.

For instance the $5\text{-}HT_6/D_2$, $5\text{-}HT_6/\alpha_1$-adrenergic or $5\text{-}HT_6/H_1$ selectivities of the compounds according to the present invention, i.e., the ratios $K_i(D_2)/K_i(5\text{-}HT_6)$, $K_i(\alpha_1\text{-adrenergic})/K_i(5\text{-}HT_6)$ or $K_i(H_1)/K_i(5\text{-}HT_6)$ of the receptor binding constants, is as a rule at least 25, preferably at least 50, even better at least 100.

The displacement of $[^3H]SCH23390$ or $[^{125}I]$spiperone can be used, for example, for carrying out receptor binding studies on $D_1$, $D_2$ and $D_4$ receptors.

Furthermore the compounds of the present invention because of their structural features are susceptible to display an enhanced brain penetration than other known $5\text{-}HT_6$ receptor ligands.

Because of their binding profile, the compounds of the present invention can be used for treating diseases which respond to $5\text{-}HT_6$ receptor ligands (or which are susceptible to treatment with a $5\text{-}HT_6$ receptor ligand), i.e., they are effective for treating those medical disorders or diseases in which exerting an influence on (modulating) the $5\text{-}HT_6$ receptors leads to an improvement in the clinical picture or to the disease being cured. Examples of these diseases are disorders or diseases of the central nervous system.

Disorders or diseases of the central nervous system are understood as meaning disorders which affect the spinal cord and, in particular, the brain. Within the meaning of the invention, the term "disorder" denotes disturbances and/or anomalies which are as a rule regarded as being pathological conditions or functions and which can manifest themselves in the form of particular signs, symptoms and/or malfunctions. While the treatment according to the invention can be directed toward individual disorders, i.e., anomalies or pathological conditions, it is also possible for several anomalies, which may be causatively linked to each other, to be combined into patterns, i.e., syndromes, which can be treated in accordance with the invention.

The disorders which can be treated in accordance with the invention are in particular disorders which respond to a modulation of the $5\text{-}HT_6$ receptor. They include cognitive dysfunctions, such as a deficit in memory, cognition and learning, in particular associated with Alzheimer's disease, age-related cognitive decline and mild cognitive impairment, attention deficit disorder/hyperactivity syndrome, personality disorders, such as schizophrenia, in particular cognitive deficits related with schizophrenia, affective disorders such as depression, anxiety and obsessive compulsive disorders, motion or motor disorders such as Parkinson's disease and epilepsy, migraine, sleep disorders (including disturbances of the Circadian rhythm), feeding disorders, such as anorexia and bulimia, certain gastrointestinal disorders such as Irritable Bowl Syndrome, diseases associated with neurodegeneration, such as stroke, spinal or head trauma and head injuries, such as hydrocephalus, addiction diseases including e.g., drug addiction and obesity.

The addiction diseases include psychic disorders and behavioral disturbances which are caused by the abuse of psychotropic substances, including certain pharmaceuticals, such as sedative, anxiolytica, hypnotics or narcotics (hereinafter also referred to as drug addiction), and also other addiction diseases, such as addiction to gaming (gambling; impulse control disorders not elsewhere classified). Examples of addictive substances are: opioids (e.g., morphine, heroin and codeine), cocaine; nicotine; alcohol; substances which interact with the GABA chloride channel complex, sedatives, hypnotics and tranquilizers, for example benzodiazepines; LSD; cannabinoids; psychomotor stimulants, such as 3,4-methylenedioxy-N-methylamphetamine (ecstasy); amphetamine and amphetamine-like substances such as methylphenidate and other stimulants including caffeine. Addictive substances which come particularly into consideration are opioids, cocaine, amphetamine or amphetamine-like substances, hallucinogens, NMDA-receptor antagonists such phencyclidine and related cyclidines, dextrometorphan, dextrorphan, ibogaine, ketimine and tiletamine, cannabis, nicotine and alcohol. Other addiction diseases include gaming (gambling), including problem gambling (compulsive gambling, ludomania), computer or video game addiction and internet addiction.

With regard to the treatment of addiction diseases, particular preference is given to those compounds according to the present invention which themselves do not possess any psychotropic effect. This can also be observed in a test using rats, which, after having been administered compounds which can be used in accordance with the invention, reduce their self administration of psychotropic substances, for example cocaine or alcohol.

According to another aspect of the present invention, the compounds according to the invention are suitable for treating disorders whose causes can at least partially be attributed to an anomalous activity of $5\text{-}HT_6$ receptors.

According to another aspect of the present invention, the treatment is directed, in particular, toward those disorders which can be influenced, within the sense of an expedient medicinal treatment, by the binding of preferably exogeneously administered binding partners (ligands) to $5\text{-}HT_6$ receptors.

The diseases which can be treated with the compounds according to the invention are frequently characterized by progressive development, i.e., the above-described conditions change over the course of time; as a rule, the severity increases and conditions may possibly merge into each other or other conditions may appear in addition to those which already exist.

The compounds of the present invention can be used to treat a large number of signs, symptoms and/or malfunctions which are connected with the disorders of the central nervous system and, in particular, the abovementioned conditions. These signs, symptoms and/or malfunctions include, for example, a disturbed relationship to reality, lack of insight and ability to meet customary social norms or the demands made by life, changes in temperament, changes in individual drives, such as hunger, sleep, thirst, etc., and in mood, disturbances in the ability to observe and combine, changes in personality, in particular emotional lability, hallucinations, ego-disturbances, distractedness, ambivalence, autism, depersonalization and false perceptions, delusional ideas, chanting speech, lack of synkinesia, short-step gait, flexed posture of trunk and limbs, tremor, poverty of facial expression, monotonous speech, depressions, apathy, impeded spontaneity and decisiveness, impoverished association ability, anxiety, nervous agitation, stammering, social phobia, panic disturbances, withdrawal symptoms in association with dependency, maniform syndromes, states of excitation and confusion, dysphoria, dyskinetic syndromes and tic disorders, e.g., Huntington's chorea and Gilles-de-la-Tourette's syndrome, vertigo syndromes, e.g., peripheral positional, rotational and oscillatory vertigo, melancholia, hysteria, hypochondria and the like.

Within the meaning of the invention, a treatment also includes a preventive treatment (prophylaxis), in particular as relapse prophylaxis or phase prophylaxis, as well as the treatment of acute or chronic signs, symptoms and/or malfunctions. The treatment can be orientated symptomatically, for example as the suppression of symptoms. It can be effected over a short period, be orientated over the medium term or can be a long-term treatment, for example within the context of a maintenance therapy.

The compounds according to the invention are preferentially suitable for treating diseases of the central nervous system, more preferably for treating cognitive dysfunctions and in particular, for treating cognitive dysfunctions associated with schizophrenia or with Alzheimer's disease.

According to another aspect of the invention the compounds of the present invention are particularly suitable for treating addiction diseases caused for instance by the abuse of psychotropic substances, such as pharmaceuticals, narcotics, nicotine or alcohol, including psychic disorders and behavioral disturbances related thereto. The compounds of the present invention are likewise particularly suitable for treating addiction diseases which are not caused by the abuse of psychotropic substances, such as gaming (gambling), including problem gambling (compulsive gambling, ludomania), computer or video game addiction and internet addiction. With regard to addiction diseases, the compound of the present invention can be used for the therapy during addiction and also for preventing relapse into addiction.

According to another aspect of the invention the compounds of formulae (I) and (I)', their salts and their N-oxides are particularly suitable for treating nutritional disorders, such as obesity, as well as diseases related thereto, such as cardiovascular diseases, digestive diseases, respiratory diseases, cancer or type 2 diabetes.

Within the context of the treatment, the use according to the invention of the described compounds involves a method. In this method, an effective quantity of one or more compounds, as a rule formulated in accordance with pharmaceutical and veterinary practice, is administered to the individual to be treated, preferably a mammal, in particular a human being, productive animal or domestic animal. Whether such a treatment is indicated, and in which form it is to take place, depends on the individual case and is subject to medical assessment (diagnosis) which takes into consideration signs, symptoms and/or malfunctions which are present, the risks of developing particular signs, symptoms and/or malfunctions, and other factors.

As a rule, the treatment is effected by means of single or repeated daily administration, where appropriate together, or alternating, with other active compounds or active compound-containing preparations such that a daily dose of preferably from about 0.1 to 1000 mg/kg of bodyweight, in the case of oral administration, or of from about 0.1 to 100 mg/kg of bodyweight, in the case of parenteral administration, is supplied to an individual to be treated.

The invention also relates to the production of pharmaceutical compositions for treating an individual, preferably a mammal, in particular a human being, productive animal or domestic animal. Thus, the compounds of formulae I or I', their salts and/or their N-oxides are customarily administered in the form of pharmaceutical compositions which comprise a pharmaceutically acceptable excipient together with at least one compound according to the invention and, where appropriate, other active compounds. These compositions can, for example, be administered orally, rectally, transdermally, subcutaneously, intravenously, intramuscularly or intranasally.

Examples of suitable pharmaceutical formulations are solid medicinal forms, such as powders, granules, tablets, in particular film tablets, lozenges, sachets, cachets, sugar-coated tablets, capsules, such as hard gelatin capsules and soft gelatin capsules, suppositories or vaginal medicinal forms, semisolid medicinal forms, such as ointments, creams, hydrogels, pastes or plasters, and also liquid medicinal forms, such as solutions, emulsions, in particular oil-in-water emulsions, suspensions, for example lotions, injection preparations and infusion preparations, and eyedrops and eardrops. Implanted release devices can also be used for administering inhibitors according to the invention. In addition, it is also possible to use liposomes or microspheres.

When producing the compositions, the compounds according to the invention are optionally mixed or diluted with one or more excipients. Excipients can be solid, semisolid or liquid materials which serve as vehicles, carriers or medium for the active compound.

Suitable excipients are listed in the specialist medicinal monographs. In addition, the formulations can comprise pharmaceutically acceptable carriers or customary auxiliary substances, such as glidants; wetting agents; emulsifying and suspending agents; preservatives; antioxidants; antiirritants; chelating agents; coating auxiliaries; emulsion stabilizers; film formers; gel formers; odor masking agents; taste corrigents; resin; hydrocolloids; solvents; solubilizers; neutralizing agents; diffusion accelerators; pigments; quaternary ammonium compounds; refatting and overfatting agents; raw materials for ointments, creams or oils; silicone derivatives; spreading auxiliaries; stabilizers; sterilants; suppository bases; tablet auxiliaries, such as binders, fillers, glidants, disintegrants or coatings; propellants; drying agents; opacifiers; thickeners; waxes; plasticizers and white mineral oils. A formulation in this regard is based on specialist knowledge as described, for example, in Fiedler, H. P., Lexikon der Hilfsstoffe für Pharmazie, Kosmetik und angrenzende Gebiete [Encyclopedia of auxiliary substances for pharmacy, cosmetics and related fields], $4^{th}$ edition, Aulendorf: ECV-Editio-Kantor-Verlag, 1996.

The following examples serve to explain the present invention without limiting its scope.

The compounds were either characterized via proton-NMR in $d_6$-dimethylsulfoxid or d-chloroform on a 400 MHz or 500 MHz NMR instrument (Bruker AVANCE), or by mass spectrometry, generally recorded via HPLC-MS in a fast gradient on C18-material (electrospray-ionisation (ESI) mode), or melting point.

The magnetic nuclear resonance spectral properties (NMR) refer to the chemical shifts ($\delta$) expressed in parts per million (ppm). The relative area of the shifts in the $^1$H NMR spectrum corresponds to the number of hydrogen atoms for a particular functional type in the molecule. The nature of the shift, as regards multiplicity, is indicated as singlet (s), broad singlet (s. br.), doublet (d), broad doublet (d br.), triplet (t), broad triplet (t br.), quartet (q), quintet (quint.) and multiplet (m).

I. Preparation of the Intermediate Compounds II

PREPARATION EXAMPLE 1

4-[5-(3-Difluoromethoxy-benzenesulfonylamino)-2-methoxy-phenyl]-piperazine-1-carboxylic Acid tert-butyl Ester

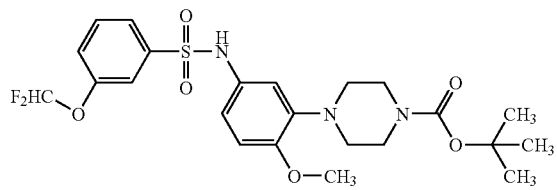

1.1 1-(2-Methoxy-5-nitro-phenyl)-piperazine 63 mL of 5 M sulphuric acid were dropwise added to 60 g of commercially available 1-(2-methoxyphenyl)-piperazine (312 mmol) within 30 minutes at 0° C., followed by the addition of 306 mL of concentrated sulphuric acid. The mixture was stirred for 90 minutes. Then 25.2 g of potassium nitrate (249.65 mmol) were added in portions within 1 h. After stirring for 3 h, another 3.16 g of potassium nitrate (31.2 mmol) were added. When the reaction was complete, the mixture was poured onto 1 kg of ice water and the pH was adjusted to pH 12 with aqueous sodium hydroxide. 300 mL of water were added, the aqueous phase was extracted three times with 300 mL of ethyl acetate each. The organic phases were combined, dried over magnesium sulfate, filtered, and the solvent was evaporated under reduced pressure to yield 48.7 g of crude product. This material was dissolved in a small amount of diethyl ether. Crystallization started upon scratching the glass surface. The residue was filtered, washed with cold diethyl ether, and dried to yield 34.2 g of the title compound.

ESI-MS:238.1 [M+H]$^+$ $^1$H-NMR (DMSO-d$_6$, 400 Hz): δ [ppm] 7.9 (d, 1H), 7.6 (s, 1H), 7.15 (d, 1H), 3.95 (s, 3H), 3.0 (m, 4H), 285 (m, 4H), 0.1 (s, 1H), 9.8-9.9 (s, broad, 2H), 7.5-7.65 (m, 2H), 7.4-7.5 (m, 2H), 7.3 (t, 1H, CHF$_2$), 6.85 (d, 1H), 6.7 (d, 1H), 6.65 (s, 1H). 3.7 (s, 3H), 3.2 (m, 4H), 3.1 (m, 4H).

1.2 4-(2-Methoxy-5-nitro-phenyl)-piperazine-1-carboxylic Acid tert-butyl Ester To a solution of 20 g of 1-(2-methoxy-5-nitro-phenyl)-piperazine (84.29 mmol) in 300 ml of tetrahydrofurane, 9.3 g of di-tert.-butyldicarbonate (88.51 mmol) were added dropwise at room temperature. After stirring for 16 h, the solvent was evaporated and the residue was dissolved in 250 mL of ethyl acetate. The solution was washed twice with 150 mL water each. The organic phase was dried over magnesium sulfate, filtered, and the solvent was evaporated under reduced pressure to yield 33.1 g of the title compound as a yellowish oil that crystallizes upon standing.

ESI-MS:338.1 [M+H]$^+$

1.3 4-(5-Amino-2-methoxy-phenyl)-piperazine-1-carboxylic Acid tert-butyl Ester 33 g of 4-(2-Methoxy-5-nitro-phenyl)-piperazine-1-carboxylic acid tert-butyl ester (97.8 mmol) were dissolved in 450 mL of methanol. 3 g of 10% Pd/C were added at room temperature under nitrogen atmosphere, and the reaction mixture was hydrogenated for 4 h. The reaction mixture was filtered over Celite, the was solvent evaporated and the remaining residue was treated with 100 mL of diisopropylether. Once crystallization started, the solvent was removed under reduced pressure and the remaining product dried thoroughly. This material was used in subsequent steps without further purification.

ESI-MS:308.4 [M+H]$^+$ $^1$H-NMR (DMSO-d$_6$, 400 Hz): δ [ppm] 7.9 (d, 1H), 7.6 (s, 1H), 7.15 (d, 1H), 3.95 (s, 3H), 3.0 (m, 4H), 285 (m, 4H), 0.1 (s, 1H), 9.8-9.9 (s, broad, 2H), 7.5-7.65 (m, 2H), 7.4-7.5 (m, 2H), 7.3 (t, 1H, CHF$_2$), 6.85 (d, 1H), 6.7 (d, 1H), 6.65 (s, 1H). 3.7 (s, 3H), 3.2 (m, 4H), 3.1 (m, 4H).

1.4 4-[5-(3-Difluoromethoxy-benzenesulfonylamino)-2-methoxy-phenyl]-piperazine-1-carboxylic Acid tert-butyl Ester 0.745 g of 4-(5-Amino-2-methoxy-phenyl)-piperazine-1-carboxylic acid tert-butyl ester (2.423 mmol) were dissolved in 35 ml of pyridine. 0.588 g of 3-(difluoromethoxy)-benzene-sulfonylchloride were added dropwise and the reaction mixture was stirred for 72 h at room temperature. The solvent was evaporated, the residue was dissolved in 40 ml dichloromethane and the organic phase was washed twice with 30 ml aqueous saturated ammonium chloride. The organic phase was dried over magnesium sulfate, filtered, and the solvent was evaporated under reduced pressure. The crude product was purified three times via silica gel chromatography using dichloromethane-methanol, and dichloromethane-ethyl acetate as eluent. 0.94 g of the title compound were isolated.

ESI-MS:514.2 [M+H]$^+$

PREPARATION EXAMPLE 2

4-{5-[(3-difluoromethoxy-benzenesulfonyl)-methyl-amino]-2-methoxy-phenyl}-piperazine-1-carboxylic Acid tert-butyl Ester

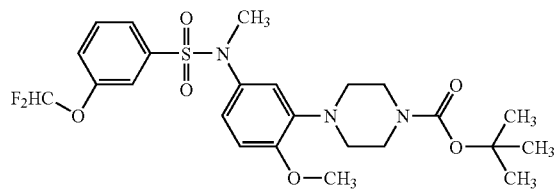

To a suspension of 0.015 g (0.374 mmol) of sodium hydride (60% in paraffin oil) in 2 mL of dimethylformamide 0.16 g of 4-[5-(3-Difluoromethoxy-benzenesulfonylamino)-2-methoxy-phenyl]-piperazine-1-carboxylic acid tert-butyl ester (0.311 mmol) from preparation example 1 were added at room temperature. After stirring for 30 minutes at 60° C., a solution of 0.053 g methyliodide (0.374 mmol) in 1 mL dimethylformamide were added dropwise. Stirring was continued for 16 h at room temperature before the solvent was evaporated. Then, 15 mL of water were added, and the aqueous phase was extracted twice with 10 mL of ethyl acetate each. The organic phases were combined, dried over magnesium sulfate, filtered, and the solvent was evaporated under reduced pressure to yield 0.156 g of crude title product which was further purified via silica gel chromatography.

ESI-MS: 528.2 [M+H]$^+$

PREPARATION EXAMPLE 3

4-[5-(3-Difluoromethoxy-benzenesulfonylamino)-2-trifluoromethoxy-phenyl]-piperazine-1-carboxylic Acid tert-butyl Ester

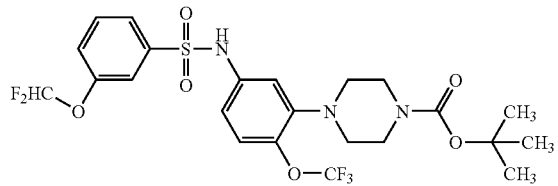

13.1 4-(5-Nitro-2-trifluoromethoxy-phenyl)-piperazine-1-carboxylic Acid tert-butyl Ester A mixture of 0.048 g palladium(II)-acetate (0.214 mmol) and 0.133 g BINAP (0.214 mmol) in 7 mL toluene was heated to 60° C., stirred for 10 min. and the obtained suspension was added dropwise to a solution of 0.51 g 2-bromo-4-nitro-1-(trifluoromethoxy)benzene (1.783 mmol), 0.343 g tert.butyl-piperazine-1-carboxylate (1.842 mmol) and 0.232 g sodium tert-butoxide (2.414 mmol) in 8 mL of toluene. The thus obtained reaction mixture was treated at 130° C. for 1.5 h in a commercial microwave oven. The organic layer was washed with water, the aqueous phase was extracted with dichloromethane and the combined organic layers were extracted with saturated aqueous sodium chloride, dried over sodium sulfate, filtered, and the solvent was evaporated under reduced pressure. The crude product was further purified via silica gel chromatography using a ISCO Companion system (eluent cyclohexane-ethyl acetate 5-25%) to yield 0.413 g of product.

ESI-MS:336.0 (−tBu) [M+H]$^+$ $^1$H-NMR (DMSO-d$_6$, 400 Hz): δ [ppm] 7.9 (d, 1H), 7.6 (s, 1H), 7.15 (d, 1H), 3.95 (s, 3H), 3.0 (m, 4H), 285 (m, 4H), 0.1 (s, 1H), 9.8-9.9 (s, broad, 2H), 7.5-7.65 (m, 2H), 7.4-7.5 (m, 2H), 7.3 (t, 1H, CHF$_2$), 6.85 (d, 1H), 6.7 (d, 1H), 6.65 (s, 1H). 3.7 (s, 3H), 3.2 (m, 4H), 3.1 (m, 4H).

3.2 4-(5-Amino-2-trifluoromethoxy-phenyl)-piperazine-1-carboxylic Acid tert-butyl Ester 0.41 g of 4-(5-Nitro-2-trifluoromethoxy-phenyl)-piperazine-1-carboxylic acid tert-butyl ester (1.055 mmol) were dissolved in 10 mL ethyl acetate and 10 mL acetic acid. 0.12 g 10% Palladium/charcoal were added and the mixture hydrogenated for 3 h at room temperature. The catalyst was filtered over Celite, washed with ethyl acetate and the combined filtrates evaporated to dryness. The residue was treated with water, the pH adjusted to 9-10 with 1 N aqueous sodium hydroxide and the aquous phase extracted twice with dichloromethane. The combined organic extracts were dried over magnesium sulfate, filtered, and the solvent evaporated under reduced pressure to yield 0.372 g of the product.

ESI-MS:362.1 [M+H]$^+$

3.3 4-[5-(3-Difluoromethoxy-benzenesulfonylamino)-2-trifluoromethoxy-phenyl]-piperazine-1-carboxylic Acid tert-butyl Ester 0.22 g of the product were obtained following the synthesis of 4-[5-(3-Difluoromethoxy-benzenesulfonylamino)-2-methoxy-phenyl]-piperazine-1-carboxylic acid tert-butyl ester. In the final purification step via silica gel chromatography, cyclohexane-ethyl acetate (10-35%) was used as eluent.

ESI-MS:512.0 (−tBu) [M+H]+

PREPARATION EXAMPLE 4

4-{5-[(2,2-Difluoro-benzo[1,3]dioxole-4-sulfonyl)-methyl-amino]-2-methoxy-phenyl}-piperazine-1-carboxylic Acid tert-butyl Ester

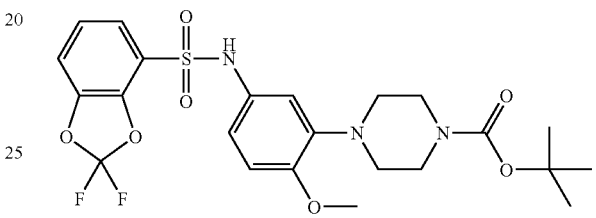

The compound was prepared as described in preparation example 1 from 4-(2-Methoxy-5-nitro-phenyl)-piperazine-1-carboxylic acid tert-butyl ester and reaction with commercially available (2,2-Difluoro-benzo[1,3]dioxole-4-sulfonyl-chloride.

ESI-MS:528.2 [M+H]$^+$

II. Preparation of the Compounds I

EXAMPLE 1

3-Difluoromethoxy-N-(4-methoxy-3-piperazin-1-yl-phenyl)-benzenesulfonamide Hydrochloride 0.17 g of 4-[5-(3-Difluoromethoxy-benzenesulfonylamino)-2-methoxy-phenyl]-piperazine-1-carboxylic acid tert-butyl ester (0.331 mmol) from preparation example 1 were treated with 1 ml of 5 N HCl in isopropanol for 3 h at 35° C. The solvent was evaporated and 5 mL of diethyl ether were added. The product started to crystallize upon scratching the glass surface. The solvent was evaporated and the solid dried thoroughly at room temperature to yield 0.125 g of title compound.

ESI-MS:414.1 [M+H]$^+$ $^1$H-NMR (DMSO-d$_6$, 400 Hz): δ [ppm] 10.1 (s, 1H), 9.8-9.9 (s, broad, 2H), 7.5-7.65 (m, 2H), 7.4-7.5 (m, 2H), 7.3 (t, 1H, CHF$_2$), 6.85 (d, 1H), 6.7 (d, 1H), 6.65 (s, 1H). 3.7 (s, 3H), 3.2 (m, 4H), 3.1 (m, 4H).

EXAMPLE 2

3-Difluoromethoxy-N-(4-methoxy-3-piperazin-1-yl-phenyl)-N-methyl-benzene-sulfonamide Hydrochloride 0.3 g (0.584 mmol) 4-{5-[(3-difluoromethoxy-benzenesulfonyl)-methyl-amino]-2-methoxy-phenyl}-piperazine-1-carboxylic acid tert-butyl ester from preparation example 2 were dissolved in 8 mL of ethanol and 0.8 mL of 5 N HCl in isopropanol were added. After stirring for 16 h at room temperature, the solvent was evaporated to yield 0.255 g of title compound.

ESI-MS:428.5 [M+H]$^+$ $^1$H-NMR (DMSO-d$_6$, 400 Hz): δ [ppm] 9.3-9.5 (s, broad, 2H), 7.7 (m, 1H), 7.55 (m, 1H), 7.4 (m, 1H), 7.3 (t, 1H, CHF$_2$), 7.2 (s, 1H), 6.9 (d, 1H), 6.7 (d, 1H), 6.5 (s, 1H), 3.8 (s, 3H), 3.0-3.2 (11H).

EXAMPLE 3

4-Difluoromethoxy-N-[4-methoxy-3-(4-methyl-piperazin-1-yl)-phenyl]-benzenesulfonamide 0.18 mL of 4-difluoromethoxybenzene sulfonyl chloride (1.13 mmol) were added to a solution of 0.25 g of (1.13 mmol) 4-methoxy-3-(4-methyl-piperazin-1-yl)-phenylamine in 10 mL of pyridine. The reaction mixture was stirred for 16 h at room temperature. The solvent was evaporated at reduced pressure. After addition of toluene and dichloromethane the mixture was again evaporated twice. The thus obtained residue was partitioned between dichloromethane and 5% aqueous ammoniumchloride. The organic phase was washed with saturated aqueous sodium chloride solution, dried over sodium sulfate, filtered, and the solvent was evaporated under reduced pressure. The obtained crude product was further purified via HPLC to yield 0.395 g of the desired title compound.

ESI-MS:428.1 [M+H]$^+$ $^1$H-NMR (CDCl$_3$, 400 Hz): δ [ppm] 7.7 (d, 2H), 7.15 (d, 2H), 6.85 (d, 1H), 6.75 (d, 1H), 6.65 (s, 1H), 6.6 (t, 1H, CHF$_2$), 6.5 (s, 1H), 3.8 (s, 3H), 3.6 (m, 2H), 3.35 (m, 2 h), 3.0-3.15 (M, 4 h), 2.85 (S, 3H).

EXAMPLE 4

2,2-Difluoro-benzo[1,3]dioxole-4-sulfonic Acid (4-methoxy-3-piperazin-1-yl-phenyl)-amide Hydrochloride The title compound was prepared by treatment of 4-{5-[(2,2-Difluoro-benzo[1,3]dioxole-4-sulfonyl)-methyl-amino]-2-methoxy-phenyl}-piperazine-1-carboxylic acid tert-butyl ester with HCl in ether and dichloromethane as solvent.

ESI-MS:428.1 [M+H]$^+$ $^1$H-NMR (MeOD, 400 Hz): δ [ppm] 7.5 (d, 1H), 7.4 (d, 1H), 7.3 (t, 1H), 7.0 (s, 1H), 6.9 (d, 1H), 6.85 (d, 1H), 3.85 (s, 3H), 3.5 (m, 4H), 3.35 (m, 4H).

EXAMPLE 5

2,2-Difluoro-benzo[1,3]dioxole-4-sulfonic Acid [4-methoxy-3-(4-methyl-piperazin-1-yl)-phenyl]-amide 285 mg of the product were obtained by reaction of 2,2-Difluoro-benzo[1,3]dioxole-4-sulfonic acid (4-methoxy-3-piperazin-1-yl-phenyl)-amide hydrochloride with formaldehyde, sodium triacetoxyborohydride and sodium sulphate in dichloromethane.

ESI-MS:442.1 [M+H]$^+$ $^1$H-NMR (CDCl$_3$, 400 Hz): δ [ppm] 7.35 (d, 1H), 7.2 (d, 1H), 7.1 (t, 1H), 6.8 (d, 1H), 6.7 (d, 1H), 6.55 (s, 1H), 3.8 (s, 3H), 2.95 (broad, 4H), 2.75 (broad, 4H), 2.5 (s, 3H).

EXAMPLE 6

3-Difluoromethoxy-N-(3-piperazin-1-yl-4-trifluoromethoxy-phenyl)-benzenesulfonamide 0.22 g 4-[5-(3-Difluoromethoxy-benzenesulfonylamino)-2-trifluoromethoxy-phenyl]-piperazine-1-carboxylic acid tert-butyl ester (0.388 mmol) were dissolved in 5 ml dichloromethane. 1.5 mL 6 N hydrochlorid acid in isopropanol were added and the reaction mixture was stirred at room temperature for 2.5 h. The solvents were evaporated, the residue was dissolved in water and the pH was adjusted to 8-9 with 1 N aqueous solution of sodium hydroxide. Thereby a white suspension formed, which was extracted once with a mixture of ethyl acetate and dichloromethane. The still existent suspensions were filtered, and the combined organic filtrates were dried over sodium sulfate, filtered, and the solvent was evaporated under reduced pressure to yield 0.140 g of the desired product.

ESI-MS:468.1 [M+H]$^+$ $^1$H-NMR (DMSO-d$_6$, 400 Hz): δ [ppm] 7.6 (m, 2H), 7.5 (s, 1H), 7.4 (d, 1H), 7.3 (t, 1H, CHF$_2$), 7.1 (d, 1H), 6.75 (s, 1H), 6.7 (d, 1H), 2.8 (m, broad, 8H).

EXAMPLE 7

2-Difluoromethoxy-N-(3-piperazin-1-yl-4-difluoromethoxy-phenyl)-benzenesulfonamide Trifluoroacetate The compound was prepared starting from commercially available 2-bromo-4-nitrophenol, which was reacted with 2-chloro-2,2-difluoroacetophenone (J. Hu et al., J. Org. Chem., 2006, 71, 9845) to yield 2-bromo-1-difluoromethoxy-4-nitro-benzene. Subsequent Buchwald-Hartwig coupling of 2-bromo-1-difluoromethoxy-4-nitro-benzene with tert.butyloxycarbonyl-piperazine by analogy to preparation example 3.1, reduction of the nitro group to the corresponding aniline by analogy to preparation example 3.2, subsequent coupling with commercially available 2-difluoromethoxybenzene-sulfonylchloride by analogy to preparation example 1.4, and final deprotection under acidic conditions by analogy to example 1 yielded the title compound.

ESI-MS:450.1 [M+H]$^+$ $^1$H-NMR (DMSO-d$_6$, 400 Hz): δ [ppm] 10.4 (s, 1H), 8.7 (s, broad, 2H), 7.9 (d, 1H), 7.7 (t, 1H), 7.4 (m, 2H), 7.3 (t, 1H), 7.0 (t, 1H), 7.0 (d, 1H), 6.8 (s, 1H), 6.75 (d, 1H), 3.2 (broad, 4H), 3.0 (broad, 4H).

EXAMPLE 8

5-Difluoromethoxy-2-methoxy-N-(4-methoxy-3-piperazin-1-yl-phenyl)-benzene-sulfonamide Hydrochloride The compound was prepared as described for Example 1 by reaction of 4-(5-amino-2-methoxy-phenyl)-piperazine-1-carboxylic acid tert-butyl ester with commercially available 5-difluoromethoxy-2-methoxybenzenesulfonylchloride followed by deprotection under acidic conditions.

ESI-MS:444.1 [M+H]$^+$

EXAMPLE 9

3-Difluoromethoxy-N-(3-fluoro-4-methoxy-5-piperazin-1-yl-phenyl)-benzenesulfonamide Hydrochloride The compound was prepared by analogy to Example 7, starting from commercially available 1-bromo-3-fluoro-2-methoxy-5-nitrobenzene, which was reacted with tert.butyloxycarbonyl-piperazine by analogy to preparation example 3.1 top yield 1-(N-boc-piperazin-4-yl)-3-fluoro-2-methoxy-5-nitrobenzene. Reduction of the nitro group to the corresponding aniline by analogy to preparation example 3.2, subsequent coupling with commercially available 3-difluoromethoxybenzenesulfonylchloride by analogy to preparation example 1.4, and final deprotection of the tert.-butoxycarbonyl group under acidic conditions by analogy to example 1 yielded the title compound.

ESI-MS:432.1 [M+H]$^+$ $^1$H-NMR (DMSO-d$_6$, 400 Hz): δ [ppm] 10.6 (s, 1H), 9.6 (s, broad, 2H), 7.7 (m, 2H), 7.5 (s, 1H), 7.4 (d, 1H), 7.3 (s, 1H), 6.7 (d, 1H), 6.6 (s, 1H), 3.7 (s, 3H), 3.2 (s, broad, 8H).

EXAMPLE 10

2,2-Difluoro-benzo[1,3]dioxole-4-sulfonic acid (3-fluoro-4-methoxy-5-piperazin-1-yl-phenyl)-amide Hydrochloride The compound was prepared as described for Example 9 using commercially available 2,2-difluorobenzo[1,3]dioxole-4-sulfonyl chloride instead of 3-difluoromethoxybenzenesulfonylchloride.

ESI-MS:446.1 [M+H]$^+$ $^1$H-NMR (DMSO-d$_6$, 400 Hz): δ [ppm] 10.8 (s, broad, 1H), 8.7 (s, broad, 2H), 7.7 (d, 1H), 7.5 (d, 1H), 7.4 (m, 1H), 6.6 (d, 1H), 6.5 (s 1H), 3.75 (s, 3H), 3.3 (s, broad, 4H), 3.1 (s, broad, 4H).

EXAMPLE 11

3-Difluoromethoxy-N-[4-(2-fluoroethoxy)-3-piperazin-1-yl-phenyl]-benzenesulfonamide Hydrochloride The compound was prepared by analogy to Example 9, starting from commercially available 2-bromo-1-(2-fluoroethoxy)-4-nitrobenzene, which was reacted with tert.butyloxycarbonyl-piperazine. Subsequent reduction of the nitro group to the corresponding aniline compound 1-(N-boc-piperazin-4-yl)-2-(2-fluoroethoxy)-5-aminobenzene. Subsequent coupling of the aniline with commercially available 3-difluoromethoxy benzene sulfonylchloride, and final deprotection of the tert.-butoxycarbonyl group under acidic conditions yielded the title compound.

ESI-MS:446.2 [M+H]$^+$ $^1$H-NMR (DMSO-d$_6$, 400 Hz): δ [ppm] 10.1 (s, broad, 1H), 8.6 (s, broad, 2H), 7.6 (m, 1H), 7.55 (m, 1H), 7.4 (s, 1H), 7.3 (s, 1H), 6.7 (d, 1H), 6.6 (m, 1H), 4.8 (m, 1H), 4.7 (m, 1H), 4.2 (m, 1H), 4.1 (m, 1H), 3.2 (s, broad, 4H), 3.1 (s, broad, 4H).

EXAMPLE 12

2,2-Difluoro-benzo[1,3]dioxole-4-sulfonic acid (4-(2-fluoroethoxy)-5-piperazin-1-yl-phenyl)-amide Hydrochloride The compound was prepared as described for Example 9 using commercially available 2,2-Difluoro-benzo[1,3]dioxole-4-sulfonyl chloride and 1-(N-boc-piperazin-4-yl)-2-(2-fluoroethoxy)-5-aminobenzene from Example 11.

ESI-MS:460.2 [M+H]$^+$ $^1$H-NMR (DMSO-d$_6$, 400 Hz): δ [ppm] 10.4 (s, 1H), 8.6 (s, broad, 2H), 7.7 (d, 1H), 7.44 (d, 1H), 7.36 (m, 1H), 6.9 (d, 1H), 6.7 (s, 1H), 6.6 (d, 1H), 4.8 (m, 1H), 4.7 (m, 1H), 4.2 (m, 1H), 4.1 (m, 1H), 3.2 (s, broad, 4H), 3.1 (s, broad, 4H).

EXAMPLE 13

3-Difluoromethoxy-4-methoxy-N-(4-methoxy-3-piperazin-1-yl-phenyl)-benzenesulfonamide Hydrochloride The compound was prepared as described for Example 1 by reaction of 4-(5-amino-2-methoxy-phenyl)-piperazine-1-carboxylic acid tert-butyl ester and commercially available 3-difluoromethoxy-4-methoxy benzene sulfonylchloride, followed by deprotection under acidic conditions.

ESI-MS:444.1 [M+H]$^+$ $^1$H-NMR (DMSO-d$_6$, 400 Hz): δ [ppm] 9.9 (s, 1H), 9.1 (s, broad, 2H), 7.6 (d, 1H), 7.5 (s, 1H), 7.3 (d, 1H), 7.1 (s, 1H), 6.8 (d, 1H), 6.7 (m, 2H), 3.9 (s, 3H), 3.7 (s, 3H), 3.2 (s, broad, 4H), 3.1 (s, broad, 4H).

EXAMPLE 14

2-Difluoromethoxy-N-(4-methoxy-3-piperazin-1-yl-phenyl)-benzenesulfonamide Trifluoroacetate The compound was prepared as described for Example 1 by reaction of 4-(5-amino-2-methoxy-phenyl)-piperazine-1-carboxylic acid tert-butyl ester with commercially available 2-difluoromethoxy benzene sulfonylchloride followed by deprotection under acidic conditions.

ESI-MS:414.1 [M+H]$^+$ $^1$H-NMR (DMSO-d$_6$, 400 Hz): δ [ppm] 10.0 (s, 1H), 8.7 (s, broad, 2H), 7.8 (d, 1H), 7.65 (t, 1H), 7.3-7.4 (m, 2H), 7.3 (s, 1H), 6.8 (d, 1H), 6.7 (m, 2H), 3.7 (s, 3H), 3.2 (s, broad, 4H), 3.0 (s, broad, 4H).

EXAMPLE 15

4-Difluoromethoxy-N-(4-methoxy-3-piperazin-1-yl-phenyl)-benzenesulfonamide Hydrochloride The compound was prepared as described for Example 1 by reaction of 4-(5-amino-2-methoxy-phenyl)-piperazine-1-carboxylic acid tert-butyl ester with commercially available 4-difluoromethoxy benzene sulfonylchloride followed by deprotection.

ESI-MS:414.1 [M+H]$^+$ $^1$H-NMR (DMSO-d$_6$, 400 Hz): δ [ppm] 10.0 (s, 1H), 8.95 (s, broad, 2H), 7.75 (d, 2H), 7.4 (m, 1H), 7.3 (d, 2H), 6.85 (d, 1H), 6.65 (m, 2H), 3.7 (s, 3H), 3.2 (s, broad, 4H), 3.05 (s, broad, 4H).

EXAMPLE 16

3-Difluoromethoxy-N-ethyl-N-[4-methoxy-3-(4-methyl-piperazin-1-yl)-phenyl]-benzenesulfonamide Hydrochloride The compound was prepared by analogy to the methods described for Preparation Example 2 and Examples 1 and 5 from 4-{5-[(3-difluoromethoxybenzenesulfonyl)-amino]-2-methoxyphenyl}-piperazine-1-carboxylic acid tert-butyl ester, which was reacted with sodium hydride and ethylbromide to yield 4-{5-[(3-difluoromethoxy-benzenesulfonyl)-ethyl-amino]-2-methoxy-phenyl}-piperazine-1-carboxylic acid tert-butyl ester, which was deprotected and subsequently subjected to reductive amination with aqueous formaldehyde and sodium triacetoxyborohydride as described for example 5 to yield the title compound.

ESI-MS:456.2 [M+H]$^+$ $^1$H-NMR (DMSO-d$_6$, 400 Hz): δ [ppm] 11.3 (s, broad, 1H), 7.7 (m, 1H), 7.55 (m, 1H), 7.45 (m, 2H), 7.3 (s, 1H), 6.9 (d, 1H), 6.7 (d, 1H), 6.4 (s, 1H), 3.7 (s, 3H), 3.55 (m, 2H), 3.4 (m, 2H), 3.35 (m, 2H), 3.15 (m, 2H), 2.9 (m, 2H), 2.75 (d, 3H), 0.95 (t, 3H).

EXAMPLE 17

3-Difluoromethoxy-N-(3-fluoropropyl)-N-(4-methoxy-3-piperazin-1-yl-phenyl)-benzenesulfonamide Hydrochloride The compound was prepared by analogy to the methods described for Preparation Example 2 and Example 1 from 4-{5-[(3-difluoromethoxybenzenesulfonyl)-amino]-2-methoxy-phenyl}-piperazine-1-carboxylic acid tert-butyl ester, which was reacted with sodium hydride and 3-fluoro-1-bromopropane to yield 4-{5-[(3-difluoromethoxy-benzenesulfonyl)-(3-fluoropropyl)amino]-2-methoxy-phenyl}-piperazine-1-carboxylic acid tert-butyl ester, which was deprotected to yield the title compound.

ESI-MS:474.1 [M+H]$^+$ $^1$H-NMR (DMSO-d$_6$, 400 Hz): δ [ppm] 9.3 (s, broad, 2H), 7.7 (t, 1H), 7.5 (d, 1H), 7.45 (d, 1H), 7.4 (m, 1H), 7.3 (s, 1H), 6.9 (d, 1H), 6.7 (d, 1H), 6.4 (s, 1H), 4.5 (t, 1H), 4.4 (t, 1H), 3.7 (s, 3H), 3.65 (t, 2H), 3.15 (s, broad, 4H), 3.05 (s, broad, 4H), 1.75 (m, 1H), 1.7 (m, 1H).

EXAMPLE 18

3-Difluoromethoxy-N-(4-methoxy-3-piperazin-1-yl-phenyl)-N-propyl-benzene-sulfonamide Hydrochloride The compound was prepared by analogy to the methods described for Preparation Example 2 and Example 1 from 4-{5-[(3-difluoromethoxybenzenesulfonyl)-amino]-2-methoxy-phenyl}-piperazine-1-carboxylic acid tert-butyl ester, which was reacted with sodium hydride and 1-bromopropane to yield 4-{5-[(3-difluoromethoxy-benzenesulfonyl)-propylamino]-2-methoxy-phenyl}-piperazine-1-carboxylic acid tert-butyl ester, which was deprotected to yield the title compound.

ESI-MS:456.1 [M+H]$^+$ $^1$H-NMR (DMSO-d$_6$, 400 Hz): δ [ppm] 9.4 (s, broad, 2H), 7.7 (t, 1H), 7.5 (d, 1H), 7.45 (d, 1H), 7.4 (m, 1H), 7.3 (s, 1H), 6.9 (d, 1H), 6.7 (d, 1H), 6.4 (s, 1H), 3.7 (s, 3H), 3.45 (m, 2H), 3.15 (m, 4H), 3.05 (m, 4H), 1.3 (m, 2H), 0.8 (t, 3H).

EXAMPLE 19

N-(2-Chloro-4-methoxy-5-piperazin-1-yl-phenyl)-3-difluoromethoxy-benzene-sulfonamide Trifluoroacetate The compound was prepared by reaction of N-(4-methoxy-5-piperazin-1-yl-phenyl)-3-difluoromethoxybenzene-sulfonamide hydrochloride with 3 equivalents of iodine monochloride.

ESI-MS:448.1 [M+H]$^+$ $^1$H-NMR (DMSO-d$_6$, 400 Hz): δ [ppm] 10.0 (s, 1H), 9.0 (s, broad, 2H), 7.6 (t, 1H), 7.5 (d, 1H), 7.45 (d, 1H), 7.4 (s, 1H), 7.3 (m, 1H), 6.95 (s, 1H), 6.6 (s, 1H), 3.8 (s, 3H), 3.2 (broad, 4H), 3.0 (broad, 4H).

EXAMPLE 20

3-Difluoromethoxy-N-[3-(4-methyl-piperazin-1-yl)-4-trifluoromethoxy-phenyl]-benzenesulfonamide Hydrochloride The compound was prepared by reaction of 3-difluoromethoxy-N-[3-(piperazin-1-yl)-4-trifluoromethoxyphenyl]-benzenesulfonamide (compound of Example 6) with aqueous formaldehyde and sodium triacetoxyborohydride as described for Example 5.

ESI-MS:482.1 [M+H]$^+$ $^1$H-NMR (DMSO-d$_6$, 400 Hz): δ [ppm] 11.2 (broad, 1H), 10.8 (broad, 1H), 7.65 (m, 2H), 7.5 (s, 1H), 7.45 (d, 1H), 7.3 (s, 1H), 7.2 (m, 1H), 6.9 (s, 1H), 6.85 (d, 1H), 3.0-3.4 (broad, 8H), 2.8 (s, 3H).

EXAMPLE 21

2,2-Difluoro-benzo[1,3]dioxole-4-sulfonic acid [4-methoxy-3-(4-methyl-piperazin-1-yl)-phenyl]-methyl-amide Hydrochloride The compound was prepared by reaction of 2,2-difluoro-benzo[1,3]dioxole-4-sulfonic acid [4-methoxy-3-(4-piperazin-1-yl)-phenyl]-methyl-amide hydrochloride (compound of example 23) with aqueous formaldehyde and sodium triacetoxyborohydride as described for Example 5.

ESI-MS:456.1 [M+H]$^+$ $^1$H-NMR (DMSO-d$_6$, 400 Hz): δ [ppm] 11.2 (broad, 1H), 7.8 (d, 1H), 7.4 (t, 1H), 7.3 (d, 1H), 6.9 (d, 1H), 6.8 (d, 1H), 6.6 (s, 1H), 3.7 (s, 3H), 3.2 (s, 3H), 3.1-3.5 (broad, 8H), 2.75 (s, 3H).

EXAMPLE 22

2,2-Difluoro-benzo[1,3]dioxole-4-sulfonic acid ethyl-(4-methoxy-3-piperazin-1-yl-phenyl)-amide Hydrochloride The compound was prepared by reaction of 4-{5-[(2,2-difluoro-benzo[1,3]dioxole-4-sulfonyl)-methyl-amino]-2-methoxy-phenyl}-piperazine-1-carboxylic acid tert-butyl ester with sodium hydride and ethylbromide, and subsequent deprotection of the tert.butoxycarbonyl group with hydrochlorid acid in isopropanol.

ESI-MS:456.2 [M+H]$^+$ $^1$H-NMR (DMSO-d$_6$, 400 Hz): δ [ppm] 9.5 (s, broad, 2H), 7.75 (d, 1H), 7.4 (t, 1H), 7.3 (d, 1H), 6.9 (d, 1H), 6.7 (d, 1H), 6.5 (s, 1H), 3.8 (s, 3H), 3.65 (m, 2H), 3.15 (broad, 4H), 3.05 (broad, 4H), 1.0 (t, 3H).

EXAMPLE 23

2,2-Difluoro-benzo[1,3]dioxole-4-sulfonic acid methyl-(4-methoxy-3-piperazin-1-yl-phenyl)-amide Hydrochloride The compound was prepared by reaction of 4-{5-[(2,2-difluorobenzo[1,3]dioxole-4-sulfonyl)-methyl-amino]-2-methoxy-phenyl}-piperazine-1-carboxylic acid tert-butyl ester with sodium hydride and methyliodide by analogy to Preparation Example 3, and subsequent deprotection of the tert.butoxycarbonyl group with hydrochloric acid in isopropanol.
ESI-MS:442.2 [M+H]$^+$
$^1$H-NMR (DMSO-d$_6$, 400 Hz): δ [ppm] 9.5 (s, broad, 2H), 7.75 (d, 1H), 7.4 (t, 1H), 7.3 (d, 1H), 6.9 (d, 1H), 6.65 (d, 1H), 6.6 (s, 1H), 3.8 (s, 3H), 3.2 (s, 3H), 3.15 (broad, 4H), 3.1 (broad, 4H).

EXAMPLE 24

3-Difluoromethoxy-N-[4-methoxy-3-(4-methyl-piperazin-1-yl)-phenyl]-N-methyl-benzenesulfonamide Hydrochloride The compound was prepared by reaction of 3-difluoromethoxy-N-[4-methoxy-3-(piperazin-1-yl)-phenyl]-N-methyl-benzenesulfonamide hydrochloride (compound of example 2) with aqueous formaldehyde and sodium triacetoxyborohydride as described for example 5.
ESI-MS:442.2 [M+H]$^+$
$^1$H-NMR (DMSO-d$_6$, 400 Hz): δ [ppm] 11.3 (s, broad, 1H), 7.7 (t, 1H), 7.6 (d, 1H), 7.4 (m, 2H), 7.25 (m, 1H), 6.9 (d, 1H), 6.7 (d, 1H), 6.5 (s, 1H), 3.8 (s, 3H), 3.3-3.5 (m, 4H), 3.1-3.2 (m, 2H), 3.1 (s, 3H), 2.9 (m, 2H), 2.75 (d, 3H).

EXAMPLE 25

3-Difluoromethoxy-N-[4-methoxy-3-(4-methyl-piperazin-1-yl)-phenyl]-benzenesulfonamide The compound was prepared by reaction of 3-difluoromethoxy-N-[4-methoxy-3-(piperazin-1-yl)-phenyl]-benzenesulfonamide hydrochloride (compound of example 1) with aqueous formaldehyde and sodium triacetoxyborohydride as described for example 5.
ESI-MS:428.1 [M+H]$^+$
$^1$H-NMR (DMSO-d$_6$, 400 Hz): δ [ppm] 9.9 (s, broad, 1H), 7.6 (m, 1H), 7.55 (m, 1H), 7.45 (m, 2H), 7.3 (m, 1H), 6.8 (d, 1H), 6.65 (d, 1H), 6.5 (s, 1H), 3.7 (s, 3H), 2.8 (broad, 4H), 2.4 (broad, 4H), 2.2 (s, 3H).

EXAMPLE 26

3-Difluoromethoxy-N-(4-fluoro-3-piperazin-1-yl-phenyl)-benzenesulfonamide Hydrochloride The compound was prepared by analogy to Example 9, starting from commercially available 2-bromo-1-fluoro-4-nitrobenzene, which was reacted with tert.butyl-oxycarbonyl-piperazine. Subsequent reduction of the nitro group to the corresponding aniline compound 1-(N-boc-piperazin-4-yl)-2-fluoro-5-aminobenzene. Subsequent coupling of the aniline with commercially available 3-difluoromethoxybenzene sulfonylchloride, and final deprotection of the tert.-butoxycarbonyl group under acidic conditions yielded the title compound.
ESI-MS:402.1 [M+H]$^+$
$^1$H-NMR (DMSO-d$_6$, 400 Hz): δ [ppm] 10.4 (s, 1H), 9.3 (s, broad, 2H), 7.6 (m, 2H), 7.5 (m, 2H), 7.3 (m, 1H), 7.1 (m, 1H), 6.8 (d, 1H), 6.7 (d, 1H), 3.2 (s, broad, 4H), 3.1 (s, broad, 4H).

EXAMPLE 27

2,2-Difluoro-benzo[1,3]dioxole-4-sulfonic acid (4-fluoro-3-piperazin-1-yl-phenyl)-amide Hydrochloride The compound was prepared by analogy to Example 26 using commercially available 2,2-difluoro-benzo[1,3]dioxole-4-sulfonylchloride instead of 3-difluoromethoxybenzene sulfonylchloride.
ESI-MS:416.1 [M+H]$^+$
$^1$H-NMR (DMSO-d$_6$, 400 Hz): δ [ppm] 10.7 (s, 1H), 8.7 (s, broad, 2H), 7.7 (d, 1H), 7.5 (d, 1H), 7.4 (d, 1H), 7.1 (m, 1H), 6.8 (d, 1H), 6.7 (d, 1H), 3.3 (s, broad, 4H), 3.1 (s, broad, 4H).

EXAMPLE 28

3-Difluoromethoxy-N-(3-piperazin-1-yl-phenyl)-benzenesulfonamide Hydrochloride The compound was prepared as described for Example 1 by reaction of 4-(5-aminophenyl)-piperazine-1-carboxylic acid tert-butyl ester with commercially available 3-difluoromethoxybenzene sulfonylchloride followed by deprotection under acidic conditions.
ESI-MS:384.2 [M+H]$^+$
$^1$H-NMR (DMSO-d$_6$, 400 Hz): δ [ppm] 10.3 (s, 1H), 9.1 (s, broad, 2H), 7.6 (m, 2H), 7.5 (s, 1H), 7.4 (d, 1H), 7.3 (m, 1H), 7.1 (m, 1H), 6.7 (m, 2H), 6.6 (d, 1H), 3.24 (s, broad, 4H), 3.18 (s, broad, 4H).

EXAMPLE 29

2,2-Difluoro-benzo[1,3]dioxole-4-sulfonic acid (3-piperazin-1-yl-phenyl)-amide Hydrochloride The compound was prepared as described for Example 28 by reaction of 4-(5-aminophenyl)-piperazine-1-carboxylic acid tert-butyl ester with commercially available 2,2-Difluorobenzo[1,3]dioxole-4-sulfonyl chloride followed by deprotection under acidic conditions.
ESI-MS:398.1 [M+H]$^+$
$^1$H-NMR (DMSO-d$_6$, 400 Hz): δ [ppm] 10.7 (s, 1H), 9.0 (s, broad, 2H), 7.7 (d, 1H), 7.5 (d, 1H), 7.4 (m, 1H), 7.1 (m, 1H), 6.7 (m, 2H), 6.6 (d, 1H), 3.2 (broad, 8H).

EXAMPLE 30

2-Difluoromethoxy-N-(3-piperazin-1-yl-phenyl)-benzenesulfonamide Trifluoroacetate The compound was prepared as described for Example 28 by reaction of 4-(5-aminophenyl)-piperazine-1-carboxylic acid tert-butyl ester with commercially available 2-difluoromethoxybenzenesulfonyl chloride followed by deprotection under acidic conditions.
ESI-MS:384.1 [M+H]$^+$
$^1$H-NMR (DMSO-d$_6$, 400 Hz): δ [ppm] 7.9 (d, 1H), 7.6 (m, 1H), 7.3 (m, 2H), 7.26 (m, 1H), 6.9 (m, 1H), 6.55 (s, 1H), 6.45 (m, 2H), 2.9 (m, 4H), 2.8 (m, 4H).

EXAMPLE 31

3-Difluoromethoxy-4-methoxy-N-(3-piperazin-1-yl-phenyl)-benzenesulfonamide Trifluoroacetate The compound was prepared as described for Example 28 by reaction of 4-(5-aminophenyl)-piperazine-1-carboxylic acid tert-butyl ester with commercially available 3-Difluoromethoxy-4-methoxyphenylsulfonyl chloride followed by deprotection under acidic conditions.

ESI-MS:414.1 [M+H]$^+$ $^1$H-NMR (DMSO-d$_6$, 400 Hz): δ [ppm] 7.6 (d, 1H), 7.5 (s, 1H), 7.25 (m, 1H), 7.1 (m, 1H), 6.9 (m, 1H), 6.55 (s, 1H), 6.4 (m, 2H), 3.9 (s, 3H), 2.9 (s, broad, 4H), 2.75 (s, broad, 4H).

III. Biological Investigations

Displacement of radioligands binding to the following cloned human receptors

1. Preparation of Membranes by Ultrasonic Treatment and Differential Centrifugation Cells from stable clonal cell lines expressing the corresponding receptor (5-HT$_6$, α$_1$-adrenergic, dopamine D$_2$ or histamine H$_1$ receptors) were washed with PBS (w/o Ca$^{++}$, Mg$^{++}$) and harvested in PBS with 0.02% EDTA. The cells were collected by centrifugation at 500 g for 10 min. at 4° C., washed with PBS and centrifuged (500 g, 10 min. 4° C.). The pellets were stored at −80° C. until use. F or membrane preparation, the thawed cell pellet was resuspended in ice-cold sucrose buffer (0.25 M sucrose, 10 mM Hepes (pH 7.4), 1 mM Phenylmethylsulfonyl fluoride (PMSF) in DMSO, 5 µg/ml Pepstatin-A, 3 mM EDTA, 0.025% Bacitracin) and homogenized with a Branson Sonifier W-250 (Settings: Timer 4; Output Control 3; Duty Cycle constant; 2 to 3 cycles). Cell disruption was checked with the aid of a microscope. Remaining unbroken cells were pelleted at 1.000 g for 10 min. at 4° C. The sucrose buffer supernatant was then centrifuged at 60.000 g for 1 h at 4° C. (Beckman Ultrazentrifuge XL 80). The pellet was resuspended in 30 ml ice-cold Tris buffer (20 mM TRIS (pH 7.4), 5 µg/ml Pepstatin A, 0.1 mM PMSF, 3 mM EDTA) by pipetting through a 10 ml serological pipet and centrifuged for 1 h at 4° C. at 60.000 g. A final resuspension was performed in a small volume of ice-cold Tris buffer (see above) by pressing through a serological pipet followed by ultrasonic treatment with a Branson Sonifier W-250 (Settings: Timer 1; Output Control 3; Duty Cycle constant; 1 cycle). Protein concentration was determined (BCA-Kit; Pierce) and aliquots stored at −80° C. or in liquid nitrogen for long-term storage.

2. Receptor Binding Experiments

All receptor binding experiments were carried out in the corresponding assay buffer in a total volume of 200 µl in the presence of various concentrations of test compound (10$^{-5}$ M to 10$^{-9}$ M, tenfold serial dilution, duplicate determinations). The assays were terminated by filtration on polyethylenimine (PEI 0.1% or 0.3%) presoaked Packard Unifilter Plates (GF/C or GF/B) with a Tomtec Machill U 96 well-plate harvester. After the plates had been dried for 2 h at 55° C. in a drying chamber scin tillation cocktail (BetaPlate Scint; PerkinElmer) was added. Radioactivity was measured in a Microbeta Trilux two hours after the addition of the scintillation mixture. Data derived from liquid scintillation counting were analysed by iterative non-linear regression analysis with the use of the Statistical Analysis System (SAS): a program similar to "LIGAND" as described by Munson and Rodbard (Analytical Biochemistry 107, 220-239 (1980).

a) 5-HT$_6$ Receptor Binding Assay

HEK293 cells stably expressing the h-5-HT$_6$ receptor (NCBI Reference Sequence XM 001435) were cultured in RPMI1640 medium supplemented with 25 mM HEPES, 10% fetal calf serum and 1-2 mM glutamine. The membrane preparation was performed as described in section 1. For these membranes a K$_D$ of 1.95 nM for [$^3$H]-LSD (Lysergic Acid Diethylamide; Amersham, TRK1038) was determined by means of saturation binding experiments. On the day of the assay, the membranes were thawed, diluted in assay buffer (50 mM Tris-HCl, 5 mM CaCl$_2$, 0.1% ascorbic acid, 10 µM pargyline, pH 7.4) to a concentration of 8 µg protein/assay and homogenized by gentle vortexing For inhibition studies, 1 nM [$^3$H]-Lysergic Acid Diethylamide was incubated in the presence of various concentrations of test compound in assay buffer. Non-specific binding was defined with 1 µM methiothepin. The binding reaction was carried out for 3.5 h at room temperature. During the incubation, the plates were shaken on a plate shaker at 100 rpm and terminated by filtration on Packard Unifilter GF/C (0.1% PEI) plates, followed by 2 wash cycles with ice-cold 50 mM Tris-HCl, 5 mM CaCl$_2$.

a) Dopamine D$_2$ Receptor Binding Assay

HEK293 cells stably expressing the dopamine D$_2$ receptor (NCBI Reference Sequence NM_000795) were cultured in RPMI1640 medium supplemented with 25 mM HEPES, 10% fetal calf serum and 1-2 mM glutamine. The membrane preparation was performed as described in section 1. For these membranes a K$_D$ of 0.22 nM for [$^{125}$I]-iodospiperone (PerkinElmer Life Sciences, NEX284) was determined by means of saturation binding experiments. On the day of the assay, the membranes were thawed, diluted in assay buffer (50 mM Tris-HCl, 120 mM NaCl, 5 mM MgCl$_2$, 5 mM KCl, 1.5 mM CaCl$_2$, pH 7.4) to a concentration of 15 µg protein/assay and homogenized by gentle vortexing. For inhibition studies, 0.01 nM [$^{125}$I]-iodospiperone (PerkinElmer Life Sciences, NEX284) was incubated in the presence of various concentrations of test compound in assay buffer. Non-specific binding was defined with 1 µM haloperidol. The binding reaction was carried out for 1 h at room temperature and terminated by filtration on Packard Unifilter GF/B (0.1% PEI) plates, followed by 6 wash cycles with an ice-cold 7% polyethylenglycol solution.

b) α$_1$-Adrenergic Receptor Binding Assay

CHO-K$_1$ cells stably expressing the α$_1$-adrenergic receptor (NCBI Reference Sequence NM_033303) were cultured in RPMI1640 medium supplemented with 25 mM HEPES, 10% fetal calf serum and 1-2 mM glutamine. The membrane preparation was performed as described in section 1. For these membranes a K$_D$ of 0.12 nM for [$^3$H]-prazosine (PerkinElmer Life Sciences, NET823) was determined by means of saturation binding experiments. On the day of the assay, the membranes were thawed, diluted in assay buffer (50 mM Tris-HCl, pH 7.4) to a concentration of 4 µg protein/assay and homogenized by gentle vortexing. For inhibition studies, 0.1 nM [$^3$H]-prazosine (PerkinElmer Life Sciences, NET823) was incubated in the presence of various concentrations of test compound in assay buffer. Non-specific binding was defined with 1 µM phentolamine. The binding reaction was carried out for 1 h at room temperature and terminated by filtration on Packard Unifilter GF/C (0.1% PEI) plates, followed by 3 wash cycles with ice-cold assay buffer.

c) H$_1$ Receptor Binding Assay

CHO-K$_1$ cells stably expressing the histamine H$_1$ receptor (Euroscreen-ES-390-C, NCBI Reference Sequence NM_000861) were cultured in RPMI1640 medium supplemented with 25 mM HEPES, 10% fetal calf serum and 1-2 mM glutamine. The membrane preparation was performed as described in section 1. For these membranes a K$_D$ of 0.83 nM for [$^3$H]-pyrilamine (PerkinElmer Life Sciences, NET594) was determined by means of saturation binding experiments.

On the day of the assay, the membranes were thawed, diluted in assay buffer (50 mM $Na_2HPO_4$, 50 mM $KH_2PO_4$, pH 7.4) to a concentration of 6 μg protein/assay and homogenized by gentle vortexing. For inhibition studies, 1 nM [$^3$H]-pyrilamine (PerkinElmer Life Sciences, NET594) was incubated in the presence of various concentrations of test compound in assay buffer. Non-specific binding was defined with 1 μM pyrilamine. The binding reaction was carried out for 50 minutes at room temperature and terminated by filtration on Packard Unifilter GF/C (0.3% PEI) plates, followed by 2 wash cycles with ice-cold assay buffer.

3. Data Analysis

Data derived from liquid scintillation counting were analyzed by iterative non-linear regression analysis with the use of the Statistical Analysis System (SAS): a program similar to "LIGAND" as described by Munson and Rodbard (Anal. Biochem. 1980, 107, 220-239). Fitting was performed according to formulae described by Feldman (Anal. Biochem. 1972, 48, 317-338). $IC_{50}$, nH and $K_i$ values were expressed as geometrical mean. For receptors with a low affinity for the test compound, where the highest tested compound concentration inhibited less than 30% of specific radioligand binding, $K_i$-values were determined according to the equation of Cheng and Prusoff (Biochem. Pharmacol. 1973, 22, 2099-2108) and expressed as greater than (>).

The results of the receptor binding studies are expressed as receptor binding constants $K_i$(5-$HT_6$), $K_i$($D_2$), $K_i$($\alpha_1$-adrenergic) and $K_i$($H_1$), respectively, as described herein before, and given in table I.

In these tests, the compounds according to the invention exhibit very good affinities for the 5-$HT_6$ receptor ($K_i$<250 nM or <50 nM or <20 nM and frequently <10 nM). Furthermore those compounds bind selectively to the 5-$HT_6$ receptor, as compared to the affinity for the $D_2$, the $\alpha_1$-adrenergic or the $H_1$ receptors. These compounds exhibit little affinities for the $D_2$, $\alpha_1$-adrenergic or $H_1$ receptors ($K_i$>250 nM or >1000 nM and frequently >10000 nM).

Example 1: Ki (5$HT_6$)<10 nM.
Example 2: Ki (5$HT_6$)<20 nM.
Example 3: Ki (5$HT_6$)<20 nM.
Example 4: Ki(5$HT_6$)<10 nM.
Example 6: Ki(5$HT_6$)<20 nM.
Example 7: Ki(5$HT_6$)<50 nM
Example 8: Ki(5$HT_6$)<10 nM
Example 9: Ki(5$HT_6$)<50 nM
Example 10: Ki(5$HT_6$)<10 nM
Example 11: Ki(5$HT_6$)<10 nM
Example 12: Ki(5$HT_6$)<50 nM
Example 13: Ki(5$HT_6$)<10 nM
Example 14: Ki(5$HT_6$)<10 nM
Example 15: Ki(5$HT_6$)<50 nM
Example 16: Ki(5$HT_6$)<10 nM
Example 17: Ki(5$HT_6$)<50 nM
Example 18: Ki(5$HT_6$)<50 nM
Example 19: Ki(5$HT_6$)<50 nM
Example 20: Ki(5$HT_6$)<10 nM
Example 21: Ki(5$HT_6$)<50 nM
Example 22: Ki(5$HT_6$)<50 nM
Example 23: Ki(5$HT_6$)<50 nM
Example 24: Ki(5$HT_6$)<10 nM
Example 25: Ki(5$HT_6$)<10 nM
Example 26: Ki(5$HT_6$)<50 nM
Example 27: Ki(5$HT_6$)<50 nM
Example 28: Ki(5$HT_6$)<50 nM
Example 29: Ki(5$HT_6$)<10 nM
Example 30: Ki(5$HT_6$)<10 nM
Example 31: Ki(5$HT_6$)<50 nM 3. Determination of the Metabolic Stability The metabolic stability of the compounds of the invention was determined in the following assay by analyzing the microsomal half-life. The test substances are incubated in a concentration of 0.5 μM as follows:

0.5 μM test substance is preincubated together with liver microsomes of various species (0.25 mg of protein/ml) in 0.05M potassium phosphate buffer pH 7.4 in microtiter plates at 37° C. for 5 min. The reaction is started by adding NADPH (1 mg/mL). Aliquots are taken after 0, 5, 10, 15, 20 and 30 min, and the reaction is stopped with the same volume of acetonitrile and cooled down. The remaining test compound concentrations are being determined by liquid chromatography—mass spectrometry analysis. Intrinsic clearance values are calculated using the elimination rate constant of test compound depletion.

We claim:

1. Benzenesulfonanilide compounds of formulae I and I':

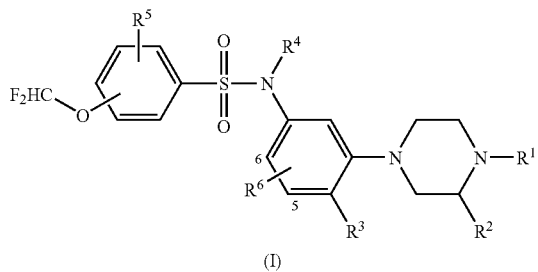

(I)

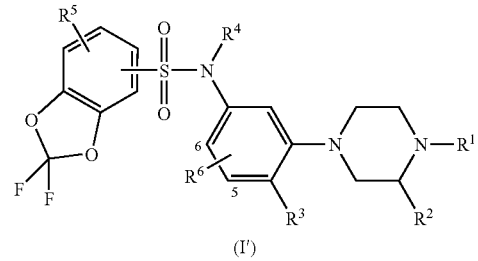

(I')

wherein
$R^1$ is hydrogen or methyl;
$R^2$ is hydrogen or methyl;
$R^3$ hydrogen, fluorine, $C_1$-$C_2$ alkoxy or fluorinated $C_1$-$C_2$ alkoxy;
$R^4$ is hydrogen or $C_1$-$C_4$ alkyl or fluorinated $C_1$-$C_4$ alkyl;
$R^5$ is hydrogen, fluorine, $C_1$-$C_2$ alkyl, fluorinated $C_1$-$C_2$ alkyl, $C_1$-$C_2$ alkoxy or fluorinated $C_1$-$C_2$ alkoxy; and
$R^6$ is hydrogen, fluorine or chlorine;
and physiologically tolerated acid addition salts and the N-oxides thereof.

2. The compounds as claimed in claim 1, wherein $R^1$ is hydrogen.

3. The compounds as claimed in claim 1, wherein $R^2$ is hydrogen.

4. The compounds as claimed in claims 1 or 2, wherein $R^2$ is methyl.

5. The compounds as claimed in claim 4, wherein the carbon atom that carries $R^2$ has S-configuration.

6. The compounds as claimed in claim 4, wherein the carbon atom that carries $R^2$ has R-configuration.

7. The compounds as claimed in claim 1, wherein $R^3$ is methoxy.

8. The compounds as claimed in claim 1, wherein $R^3$ is hydrogen or fluorine.

9. The compounds as claimed in claim 1, wherein $R^4$ is hydrogen or $C_1$-$C_2$ alkyl.

10. The compounds as claimed in claim 9, wherein $R^4$ is hydrogen.

11. The compounds as claimed in claim 1, wherein $R^5$ is hydrogen.

12. The compounds as claimed in claim 1, wherein $R^5$ is methoxy or difluoromethoxy.

13. The compounds as claimed in claim 1, wherein $R^6$ is hydrogen.

14. The compounds as claimed in claim 1, wherein $R^5$ and $R^6$ are hydrogen, $R^3$ is selected from the group consisting of $C_1$-$C_2$ alkoxy and fluorinated $C_1$-$C_2$ alkoxy and $R^4$ is selected from the group consisting of hydrogen or $C_1$-$C_2$ alkyl.

15. The compounds as claimed in claim 1, wherein one or more of the following provisos a), b), c) or d) are met:
   a) $R^5$ is selected from the group consisting of fluorine, $C_1$-$C_2$ alkyl fluorinated $C_1$-$C_2$ alkyl, $C_1$-$C_2$ alkoxy or fluorinated $C_1$-$C_2$ alkoxy;
   b) $R^6$ is fluorine or chlorine;
   c) $R^3$ is hydrogen or fluorine; and/or
   d) $R^4$ is $C_3$-$C_4$-alkyl or fluorinated $C_1$-$C_4$-alkyl;

16. The compounds as claimed in claim 15, wherein $R^6$ is fluorine or chlorine, which is located in the 6-position of the benzene ring.

17. The compounds as claimed in claim 15, wherein $R^6$ is fluorine or chlorine, which is located in the 5-position of the benzene ring.

18. The compounds as claimed in any of claims 15, 16 or 17, wherein $R^3$ is hydrogen.

19. The compounds as claimed in any of claims 15, 16 or 17, wherein $R^5$ is methoxy.

20. The compounds as claimed in claim 15, wherein $R^3$ is hydrogen.

21. The compounds as claimed in claim 1, wherein the $OCHF_2$-radical in formula I is located on the benzene ring in the ortho-position with respect to the sulfonyl group.

22. The compounds as claimed in claim 1, wherein the $OCHF_2$-radical in formula I is located on the benzene ring in the meta-position with respect to the sulfonyl group.

23. The compounds as claimed in claim 1, wherein the $OCHF_2$-radical in formula I is located on the benzene ring in the para-position with respect to the sulfonyl group.

24. A pharmaceutical composition comprising at least one compound as claimed in claim 1, optionally together with at least one physiologically acceptable carrier or auxiliary substance.

25. A method for treating a medical disorder selected from diseases of the central nervous system, addiction diseases or obesity, said method comprising administering an effective amount of at least one compound as claimed in any of claims 1 to 23 to a subject in need thereof.

26. The method as claimed in claim 25, wherein the medical disorder is a disease of the central nervous system.

27. The method as claimed in claim 26, for treating cognitive dysfunctions.

28. The method as claimed in claim 26, for treating cognitive dysfunctions associated with Alzheimer's disease.

29. The method as claimed in claim 26, for treating cognitive dysfunctions associated with schizophrenia.

30. The method as claimed in claim 25, wherein the medical disorder is an addiction disease.

31. The method as claimed in claim 25, wherein the medical disorder is obesity.

* * * * *

UNITED STATES PATENT AND TRADEMARK OFFICE
CERTIFICATE OF CORRECTION

| | | |
|---|---|---|
| PATENT NO. | : 7,790,727 B2 | Page 1 of 1 |
| APPLICATION NO. | : 12/262455 | |
| DATED | : September 7, 2010 | |
| INVENTOR(S) | : Wilfried M. Braje et al. | |

It is certified that error appears in the above-identified patent and that said Letters Patent is hereby corrected as shown below:

Col. 56, delete claims 25-31, lines 16-32.

Signed and Sealed this
Tenth Day of January, 2012

David J. Kappos
*Director of the United States Patent and Trademark Office*

UNITED STATES PATENT AND TRADEMARK OFFICE
CERTIFICATE OF CORRECTION

PATENT NO.        : 7,790,727 B2
APPLICATION NO.   : 12/262455
DATED             : September 7, 2010
INVENTOR(S)       : Wilfried M. Braje et al.

It is certified that error appears in the above-identified patent and that said Letters Patent is hereby corrected as shown below:

Delete the title page and substitute therefore the attached title page showing the corrected number of claims in patent.

Col. 56, lines 16-32, delete claims 25-31.

This certificate supersedes the Certificate of Correction issued January 10, 2012.

Signed and Sealed this
Fourteenth Day of February, 2012

David J. Kappos
*Director of the United States Patent and Trademark Office*

United States Patent
Braje et al.

(10) Patent No.: US 7,790,727 B2
(45) Date of Patent: Sep. 7, 2010

(54) BENZENESULFONANILIDE COMPOUNDS SUITABLE FOR TREATING DISORDERS THAT RESPOND TO MODULATION OF THE SEROTONIN 5-HT6 RECEPTOR

(75) Inventors: Wilfried Martin Braje, Rinteln (DE); Sean Colm Turner, Mannheim (DE); Andreas Haupt, Schwetzingen (DE); Udo Lange, Berlin (DE); Karla Drescher, Dossenheim (DE); Karsten Wicke, Altrip (DE); Liliane Unger, Ludwigshafen (DE); Mario Mezler, Forst a.d.W. (DE); Wolfgang Wernet, Neustadt a.d.W. (DE); Matthias Mayrer, Biblis (DE); Ana Jongen-Relo, Hochdorf-Assenheim (DE); Anton Bespalov, Schifferstadt (DE); Min Zhang, Gurnee, IL (US)

(73) Assignee: Abbott GmbH & Co. KG, Wiesbaden (DE)

( * ) Notice: Subject to any disclaimer, the term of this patent is extended or adjusted under 35 U.S.C. 154(b) by 0 days.

(21) Appl. No.: 12/262,455

(22) Filed: Oct. 31, 2008

(65) Prior Publication Data
US 2009/0131452 A1   May 21, 2009

Related U.S. Application Data

(60) Provisional application No. 61/001,656, filed on Nov. 2, 2007.

(51) Int. Cl.
| A61K 31/495 | (2006.01) |
| A61K 31/496 | (2006.01) |
| C07D 295/135 | (2006.01) |
| C07D 317/62 | (2006.01) |

(52) U.S. Cl. ............... 514/254.11; 514/255.03; 544/377; 544/395

(58) Field of Classification Search ............... None
See application file for complete search history.

(56) References Cited

U.S. PATENT DOCUMENTS

| 7,381,728 B2 * | 6/2008 | Dean et al. ............ 514/255.03 |
| 2003/0069233 A1 | 4/2003 | Bromidge |

FOREIGN PATENT DOCUMENTS

| WO | 98/27081 | * | 6/1998 |
| WO | 0012073 A1 | | 3/2000 |
| WO | 0012623 A3 | | 3/2000 |
| WO | 0208179 A1 | | 1/2002 |

OTHER PUBLICATIONS

Robichaud et al. Annual Reports in Medicinal Chemistry, vol. 36, p. 11-20 (2000).*
Rogers et al. Psychopharmacology, vol. 158, p 114-119 (2001).*
Ballaz et al., Analysis of 5-HT6 and HT7 Receptor Gene Expression in Rats Showing Differences in Novelty-Seeking Behavior, Neuroscience, 2007, pp. 428-438, Elsevier Ltd. on behalf of IBRO.

* cited by examiner

*Primary Examiner*—Emily Bernhardt
(74) *Attorney, Agent, or Firm*—Lisa V. Mueller; Polsinelli Shughart PC

(57) ABSTRACT

The present invention relates to novel benzenesulfonanilide compounds of the formulae I and I' and physiologically tolerated acid addition salts and the N-oxides thereof. The compounds possess valuable therapeutic properties and are particularly suitable for treating diseases that respond to modulation of the serotonin 5-$HT_6$ receptor.

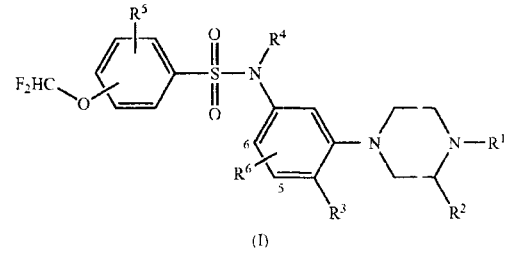

(I)

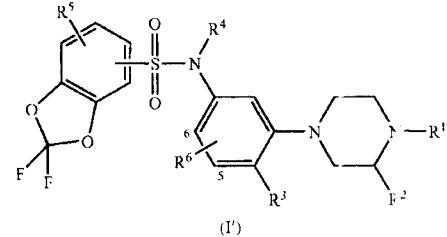

(I')

wherein
$R^1$ is hydrogen or methyl
$R^2$ is hydrogen or methyl
$R^3$ hydrogen, fluorine $C_1$-$C_2$ alkoxy or fluorinated $C_1$-$C_2$ alkoxy;
$R^4$ is hydrogen, $C_1$-$C_4$ alkyl or fluorinated $C_1$-$C_4$ alkyl;
$R^5$ is hydrogen, fluorine, $C_1$-$C_2$ alkyl, fluorinated $C_1$-$C_2$ alkyl, $C_1$-$C_2$ alkoxy or fluorinated $C_1$-$C_2$ alkoxy; and
$R^6$ is hydrogen, fluorine or chlorine.

24 Claims, No Drawings